United States Patent
Ramamurthy et al.

(10) Patent No.: US 9,188,673 B2
(45) Date of Patent: Nov. 17, 2015

(54) SYSTEMS AND METHODS FOR ULTRASOUND IMAGING

(75) Inventors: Bhaskar Ramamurthy, Los Altos, CA (US); Timothy J. Davies, Calgary (CA)

(73) Assignee: InnerVision Medical Technologies Inc., Calgary (CA)

( * ) Notice: Subject to any disclaimer, the term of this patent is extended or adjusted under 35 U.S.C. 154(b) by 365 days.

(21) Appl. No.: 13/569,081

(22) Filed: Aug. 7, 2012

(65) Prior Publication Data

US 2013/0077441 A1    Mar. 28, 2013

Related U.S. Application Data

(63) Continuation of application No. 12/950,341, filed on Nov. 19, 2010, now Pat. No. 8,234,923, which is a continuation-in-part of application No. 11/385,482, filed on Mar. 20, 2006, now Pat. No. 7,862,508, which is a continuation-in-part of application No. 11/314,139, filed on Dec. 21, 2005, now Pat. No. 7,819,805, which is a continuation-in-part of application No. 10/945,459, filed on Sep. 20, 2004, now Pat. No. 7,850,611.

(51) Int. Cl.
  *G01S 15/89*  (2006.01)
  *A61B 8/08*   (2006.01)
  *G01S 7/52*   (2006.01)

(52) U.S. Cl.
  CPC . *G01S 15/89* (2013.01); *A61B 8/08* (2013.01); *G01S 7/5209* (2013.01); *G01S 7/52049* (2013.01); *G01S 15/8977* (2013.01); *G01S 15/8995* (2013.01); *G01S 15/8993* (2013.01)

(58) Field of Classification Search
  CPC ... A61B 8/08; G01S 7/52049; G01S 15/8977; G01S 15/8993; G01S 7/5209; G01S 15/89; G01S 15/8995
  USPC ............... 73/606, 618, 628; 600/443, 447
  See application file for complete search history.

(56) References Cited

U.S. PATENT DOCUMENTS

| | | | |
|---|---|---|---|
| 3,895,381 | A | 7/1975 | Kock |
| 4,072,922 | A | 2/1978 | Taner et al. |
| 4,105,018 | A | 8/1978 | Greenleaf et al. |
| 4,259,733 | A | 3/1981 | Taner et al. |

(Continued)

FOREIGN PATENT DOCUMENTS

| | | | |
|---|---|---|---|
| EP | 0812005 | A2 | 12/1997 |
| FR | 2851662 | A1 | 8/2004 |

(Continued)

OTHER PUBLICATIONS

"International Search Report" for PCT/IB2005/003147, filed Aug. 3, 2005.

(Continued)

*Primary Examiner* — J M Saint Surin
(74) *Attorney, Agent, or Firm* — Snell & Wilmer L.L.P.

(57) ABSTRACT

An ultrasound imaging method transmits ultrasound into a medium from a source and receives and samples signals resulting from interaction of the ultrasound with the medium for each of a plurality of sources. The sampled signals are stored. Criteria are applied to select subsets of the stored sampled signals. In some embodiments the criteria relate to locations of a source and/or receiving element corresponding to a sampled signal. Images are generated from the subsets.

13 Claims, 47 Drawing Sheets

(56) References Cited

U.S. PATENT DOCUMENTS

| | | | |
|---|---|---|---|
| 4,325,257 A | 4/1982 | Kino et al. | |
| 4,452,084 A | 6/1984 | Taenzer | |
| 4,539,847 A | 9/1985 | Paap | |
| 4,566,459 A | 1/1986 | Umemura et al. | |
| 4,567,768 A | 2/1986 | Satoh et al. | |
| 4,662,222 A | 5/1987 | Johnson | |
| 4,669,482 A | 6/1987 | Ophir | |
| 4,671,115 A * | 6/1987 | Ogawa et al. | 73/626 |
| 4,781,199 A | 11/1988 | Hirama et al. | |
| 4,817,434 A | 4/1989 | Anderson | |
| 5,111,823 A * | 5/1992 | Cohen | 600/443 |
| 5,141,738 A | 8/1992 | Rasor et al. | |
| 5,161,536 A | 11/1992 | Vilkomerson et al. | |
| 5,197,475 A | 3/1993 | Antich et al. | |
| 5,226,019 A | 7/1993 | Bahorich | |
| 5,269,309 A | 12/1993 | Fort et al. | |
| 5,278,757 A | 1/1994 | Hoctor et al. | |
| 5,293,871 A | 3/1994 | Reinstein et al. | |
| 5,299,576 A | 4/1994 | Shiba | |
| 5,345,426 A | 9/1994 | Lipschutz | |
| 5,465,722 A | 11/1995 | Fort et al. | |
| 5,526,815 A | 6/1996 | Granz et al. | |
| 5,544,659 A | 8/1996 | Banjanin | |
| 5,558,092 A | 9/1996 | Unger et al. | |
| 5,568,812 A | 10/1996 | Murashita et al. | |
| 5,570,691 A | 11/1996 | Wright et al. | |
| 5,581,517 A | 12/1996 | Gee et al. | |
| 5,628,320 A | 5/1997 | Teo | |
| 5,673,697 A | 10/1997 | Bryan et al. | |
| 5,720,291 A | 2/1998 | Schwartz | |
| 5,784,334 A | 7/1998 | Sena et al. | |
| 5,785,654 A | 7/1998 | Iinuma et al. | |
| 5,838,564 A | 11/1998 | Bahorich et al. | |
| 5,850,622 A | 12/1998 | Vassiliou et al. | |
| 5,862,100 A | 1/1999 | VerWest | |
| 5,870,691 A | 2/1999 | Partyka et al. | |
| 5,892,732 A | 4/1999 | Gersztenkorn | |
| 5,920,285 A | 7/1999 | Benjamin | |
| 5,930,730 A | 7/1999 | Marfurt et al. | |
| 5,940,778 A | 8/1999 | Marfurt et al. | |
| 5,969,661 A | 10/1999 | Benjamin | |
| 5,999,836 A | 12/1999 | Nelson et al. | |
| 6,007,499 A | 12/1999 | Martin et al. | |
| 6,049,509 A | 4/2000 | Sonneland et al. | |
| 6,050,943 A | 4/2000 | Slayton et al. | |
| 6,058,074 A | 5/2000 | Swan et al. | |
| 6,092,026 A | 7/2000 | Bahorich et al. | |
| 6,135,960 A | 10/2000 | Holmberg | |
| 6,138,075 A | 10/2000 | Yost | |
| 6,166,384 A | 12/2000 | Dentinger et al. | |
| 6,174,286 B1 | 1/2001 | Ramamurthy et al. | |
| 6,210,335 B1 | 4/2001 | Miller | |
| 6,213,958 B1 | 4/2001 | Winder | |
| 6,231,511 B1 | 5/2001 | Bae | |
| 6,238,342 B1 | 5/2001 | Feleppa et al. | |
| 6,251,073 B1 | 6/2001 | Imran et al. | |
| 6,264,609 B1 | 7/2001 | Herrington et al. | |
| 6,278,949 B1 | 8/2001 | Alam | |
| 6,289,230 B1 | 9/2001 | Chaiken et al. | |
| 6,309,356 B1 | 10/2001 | Ustuner et al. | |
| 6,363,033 B1 | 3/2002 | Cole et al. | |
| 6,374,185 B1 | 4/2002 | Taner et al. | |
| 6,416,477 B1 * | 7/2002 | Jago | 600/447 |
| 6,436,046 B1 | 8/2002 | Napolitano et al. | |
| 6,464,638 B1 * | 10/2002 | Adams et al. | 600/443 |
| 6,475,150 B2 | 11/2002 | Haddad | |
| 6,480,790 B1 | 11/2002 | Calvert et al. | |
| 6,487,502 B1 | 11/2002 | Taner | |
| 6,499,536 B1 | 12/2002 | Ellingsen | |
| 6,508,768 B1 | 1/2003 | Hall et al. | |
| 6,526,163 B1 | 2/2003 | Halmann et al. | |
| 6,547,732 B2 | 4/2003 | Jago | |
| 6,551,246 B1 | 4/2003 | Ustuner et al. | |
| 6,585,647 B1 | 7/2003 | Winder | |
| 6,668,654 B2 | 12/2003 | Dubois et al. | |
| 6,672,165 B2 | 1/2004 | Rather et al. | |
| 6,681,185 B1 | 1/2004 | Young et al. | |
| 6,692,450 B1 | 2/2004 | Coleman | |
| 6,719,693 B2 | 4/2004 | Richard | |
| 6,755,787 B2 | 6/2004 | Hossack et al. | |
| 6,847,737 B1 | 1/2005 | Kouri et al. | |
| 6,866,632 B1 | 3/2005 | Chou et al. | |
| 7,011,632 B2 * | 3/2006 | Steinbacher et al. | 600/437 |
| 7,087,020 B2 | 8/2006 | Chou et al. | |
| 7,104,956 B1 | 9/2006 | Christopher | |
| 7,283,652 B2 | 10/2007 | Mendonca et al. | |
| 7,285,094 B2 | 10/2007 | Nohara et al. | |
| 7,448,998 B2 | 11/2008 | Robinson | |
| 7,510,529 B2 | 3/2009 | Chou et al. | |
| 7,682,311 B2 | 3/2010 | Simopoulos et al. | |
| 7,822,250 B2 | 10/2010 | Yao et al. | |
| 7,914,454 B2 | 3/2011 | Weber et al. | |
| 7,963,919 B2 | 6/2011 | Proulx et al. | |
| 8,234,923 B2 | 8/2012 | Ramamurthy et al. | |
| 8,430,819 B2 * | 4/2013 | Miller | 600/447 |
| 2002/0065466 A1 | 5/2002 | Rather et al. | |
| 2004/0054283 A1 | 3/2004 | Corey et al. | |
| 2004/0236217 A1 | 11/2004 | Cerwin et al. | |
| 2005/0131300 A1 | 6/2005 | Bakircioglu et al. | |
| 2005/0215883 A1 | 9/2005 | Hundley et al. | |
| 2008/0114250 A1 | 5/2008 | Urbano et al. | |
| 2013/0083628 A1 * | 4/2013 | Qiao et al. | 367/87 |
| 2013/0172743 A1 * | 7/2013 | Brewer et al. | 600/440 |
| 2014/0058266 A1 * | 2/2014 | Call et al. | 600/448 |

FOREIGN PATENT DOCUMENTS

| | | |
|---|---|---|
| JP | 07-051266 A | 2/1995 |
| JP | 9201361 A | 8/1997 |
| JP | 11-089833 A | 4/1999 |
| JP | 2004-215987 A | 8/2004 |
| JP | 2004-525715 A | 8/2004 |
| JP | 2004337457 A | 12/2004 |
| JP | 2005-526539 A | 9/2005 |
| WO | WO-9312444 A2 | 6/1993 |
| WO | WO-0043809 A1 | 7/2000 |
| WO | WO-02084594 A2 | 10/2002 |
| WO | WO-2005009245 A1 | 2/2005 |

OTHER PUBLICATIONS

Pederson, M. J. et al., "Preliminary In-Vivo Evaluation of Convex Array Synthetic Aperture Imaging", SPIE 2004.

Franklin, M. A. et al., "Parallel Implementations of an Ultrasonic Image Generation Algorithm Using MPI", Parallel and Distributed Computing and Systems, Nov. 3-6, 1999.

Smith, S. W. et al., "High-Speed Ultrasound Volumetric Imaging System—Part I: Transducer Design and Beam Steering", IEEE Transactions on Ultrasonics, Ferroelectrics, and Frequency Control, vol. 38. No. 2, Mar. 1991.

Cheeseman, P. et al., "Super-Resolved Surface Reconstruction from Multiple Images", NASA Ames Research Center, Dec. 14, 1994.

Jensen, J. A. et al., "Experimental Ultrasound System for Real-Time Synthetic Imaging", IEEE International Ultrasonics Symposium, Lake Tahoe, 1999.

Pi, Y. et al., "A SAR Parallel Processing Algorithm and its Implementation", FIEOS 2002 Conference Proceedings, 2002.

Bailey, D., "Image Resolution Improvement from Multiple Images", Massey University, available online at www.poly.edu/Podium/eef2001.cfm, Nov. 2001.

Broadstone, S. R. et al., "An Approach to Real-Time Reflection Tomography Using the Complete Dataset", IEEE, 1986 Ultrasonics symposium.

Frazier, C. H. et al., "Synthetic Aperture Techniques with a Virtual Source Element", IEEE Transactions on Ultrasonics, vol. 45, No. 1, Jan. 1998.

Peterson, D. K., et al., "Real-Time Digital Image Reconstruction: A Description of Imaging Hardware and an Analysis of Quantization Errors", IEEE Transactions on Sonics and Ultrasonics, vol. SU-31, No. 4, Jul. 1984.

(56) References Cited

OTHER PUBLICATIONS

Corl, P. D. et al., "A Digital Synthetic Focus Acoustic Imaging System for NDE", IEEE Ultrasonics Symposium Proceedings, 1978.
Nikolov, S. I. et al., "Three-Dimensional Real-Time Synthetic Aperture Imaging Using a Rotating Phased Array Transducer", IEEE International Ultrasonics Symposium, 2002.
Franklin, M. A. et al., "Parallel Implementations of 3D Synthetic-Focus Ultrasonic Image Generation Using MPI", Proceedings of the Lasted International Conference, Parallel and Distributed Computing and Systems, vol. I, Nov. 6-9, 2000.
Beetner, D. G. et al., "Generation of Synthetic-Focus Images from Pulse-Echo Ultrasound Using Difference Equations", IEEE Transactions on Medical Imaging, vol. 15, No. 5, pp. 665-672, Oct. 1996.
Richard, W. D. et al., "Real-Time Ultrasonic Scan Conversion via Linear Interpolation of Oversampled Vectors", Ultrasonic Imaging 16, 109-123, 1994.
"An Introduction to the Sampling Theorem", National Semiconductor Application Note 236, Jan. 1980.
Gray, S. H., "The Bleeding Edge of Seismic Imaging", CSEG Recorder, Dec. 2003.
Glaser, S. D. et al., "Imaging of Rock Fractures with Low-Frequency Ultrasonic Reflection/Diffraction", American Society for Testing Materials, Geotechnical Testing Journal, vol. 21, No. 4, Dec. 1998.
Gray, S. H., "Nuts and Bolts of Beam Migration", CSEG National Convention 2004.
Haun, M. A. et al., "Adaptive Focusing Through Layered Media Using the Geophysical 'Time Migration' Concept", Proc. Intl. Ultrasonics Symposium, Munich, Germany, Oct. 8-11, 2002.
Papanicolaou, G., Interferometric Imaging in Clutter II, ARO/DARPA MURI, Aug. 15, 2003.
Jensen, J. A., "Ultrasound Imaging and its Modeling", 84 Imaging of Complex Media with Acoustic and Seismic Waves, 2002.
Von Ramm, O. T. et al., "High Speed Ultrasound Volumetric Imaging System—Part II: Parallel Processing and Image Display", IEEE Transactions on Ultrasonics, Ferroelectrics, and Frequency Control, vol. 38, No. 2, Mar. 1991.
Greivenkamp, J. E., "Sub-Nyquist interferometry", vol. 26, No. 24, Applied Optics, Rochester, New York, Dec. 15, 1997.
Lyons, R. G., Understanding Digital Signal Processing, 2nd ed. (2004), Section 2.3.
Richard, W. D. "A Scalable Architecture for Real-Time Synthetic-Focus Imaging", Ultrasonic Imaging 25, 2003.
Improved Resolution in Infrared Imaging Using Randomly Shifted Images, available online at http://www.ph.tn.tudelft.nl/.about.cris/MastersProject.html, Nov. 1998.
Uden, R. C. et al., "Neural Network Training for Reservoir Characterizations of Litho Facies", Rock Solid Images, EAGE 65th Conference & Exhibition, Jun. 2003.
Brown, A. E., "Rationale and Summary of Methods for Determining Ultrasonic Properties of Materials at Lawrence Livermore National Laboratory", Lawrence Livermore National Laboratory, Apr. 25, 1997.
"Biomedical Imaging and Emerging Technologies: Practical Manual", School of Biophysical Sciences and Electrical Engineering, 2003 Edition.
Michailovich, O. et al., "Phase Unwrapping for 2-D Blind Deconvolution of Ultrasound Images", IEEE Transactions on Medical Imaging, vol. 23, No. 1, Jan. 2004.
Bahorich, M. et al., "Amplitude Responses Image Reservoir", Hart's E & P, Jan. 2002.
"EMERGE Theory", EMERGE, Jul. 1988.
Partyka, G., et al., "Interpretational Applications of Spectral Decomposition", Amoco Production Company, Leading Edge, vol. 18. No. 3, Mar. 1999.
Fang, Z. et al., "Computer-Aided Characterization for Effective Mechanical Properties of Porous Tissue Scaffolds", Department of Mechanical Engineering, Drexel University, Elsevier Ltd., 2004.
Taner, M. T., "Kohonen's Self Organizing Networks with 'Conscience'", Rock Solid Images, Nov. 1997.
Kutay, M. A. et al., "Breast Tissue Characterization Based on Modeling of Ultrasonic Echoes Using the Power-Law Shot Noise Model", Elsevier Preprint, Aug. 17, 2001.
Clapp, R. G. et al., "Iterative Resolution Estimation in Kirchhoff Imaging", Stanford Exploration Project, Report 102, Oct. 25, 1999.
Noo, F. et al., "A Two-Step Hilbert Transform Method for 2D Image Reconstruction", Phys. Med. Biol. 49, 2004.
Harvey, E. L. et al., "Techniques, for Volume Interpretation of Seismic Attributes", Expanded Abstracts, 2000.
Crain, E. R., "The New Role of Petrophysics in Geophysical Interpretation", CSEG Recorder, Sep. 2003.
"Table 1: Seismic Attributes Categories and Analysis Methods", Explorer, Jan. 2005 (web article).
Luo, Y. et al., "Generalized Hilbert Transform and its Applications in Geophysics", The Leading Edge, vol. 22, No. 3, Mar. 2003.
"Seismic Analysis", Web Article, Jan. 2006.
Spaendonck, R. L. C. et al., "Local Hilbert Transformation for Seismic Attributes", EAGE 64th Conference & Technology Exhibition, May 27-30, 2002.
Cambois, G. "Can P-Wave AVO Be Quantitative?", The Leading Edge, vol. 19, No. 11, Nov. 2000.
Bonner, B. P. et al., "Ultrasonic Characterization of Synthetic Soils for Application to Near Surface Geophysics", Presented at SAGEEP Meeting, 1999.
Sayed, A. Y., "In Sity Compressional Wave Velocity Across AN Exposed Brittle Fault Zone", 2001.
Barnes, A. E., "Seismic Attributes in Your Facies", CSEG Recorder, Sep. 2001.
Cambois, G., "AVO Processing: Myths and Reality", CSEG Recorder, Mar. 2001.
Burianyk, M. et al., "Amplitude-Vs-Offset and Seismic Rock Property Analysis: A Primer", CSEG Recorder, Nov. 2000.
Stark, T.J., "Unwrapping Instantaneous Phase to Generate a Relative Geologic Time Volume", SEG Expanded Abstract, 2003.
Taner, M. T., "Attributes Revisited" Rock Solid Images, 1992 (Revised Sep. 2000).
Russell, B. H. et al., "The AVO Modelling Volume", CREWES Consortium meeting, 2000.
"Announcements", The Leading Edge, pp. 445-446, Apr. 2001.
Ester, M. et al., "Knowledge Discovery in Spatial Databases", Invited Paper at 23rd German Conference on Artificial Intelligence (KI' '99), Bonn, Germany, 1999.
Amin, V.R. et al., "Application of Neural Network to Ultrasound Tissue Characterization Using Backscattered Signal Parameters," vol. 2, Nuclear Science Symposium and Medical Imaging Conference, Oct. 25-31, 1992, Conference Record of the 1922 IEEE.

\* cited by examiner

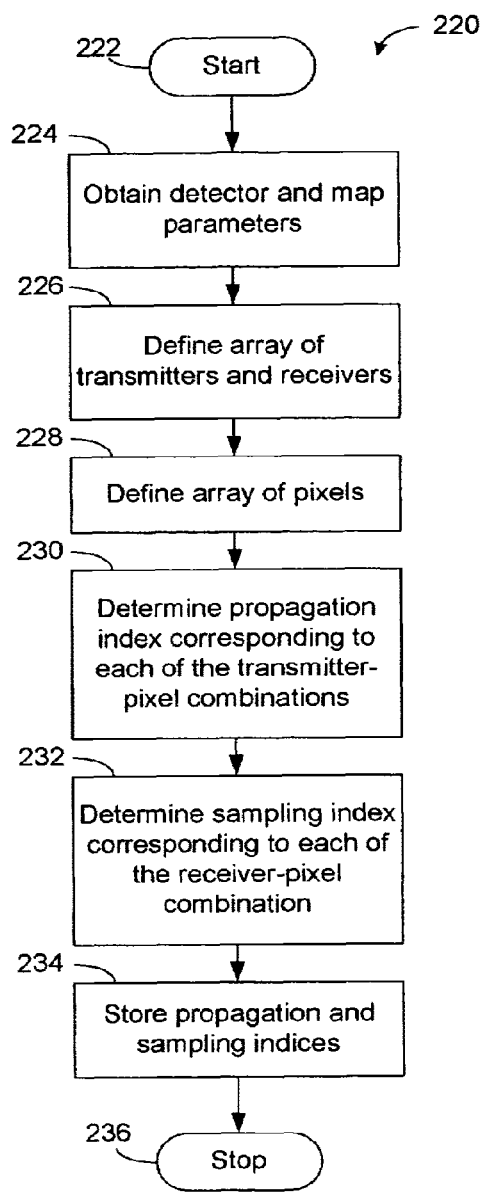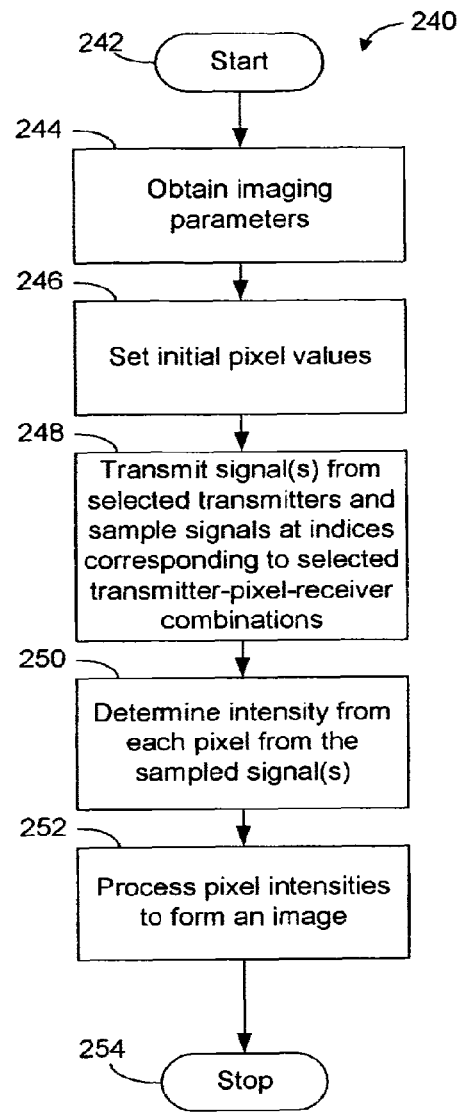
Fig. 7
Fig. 8

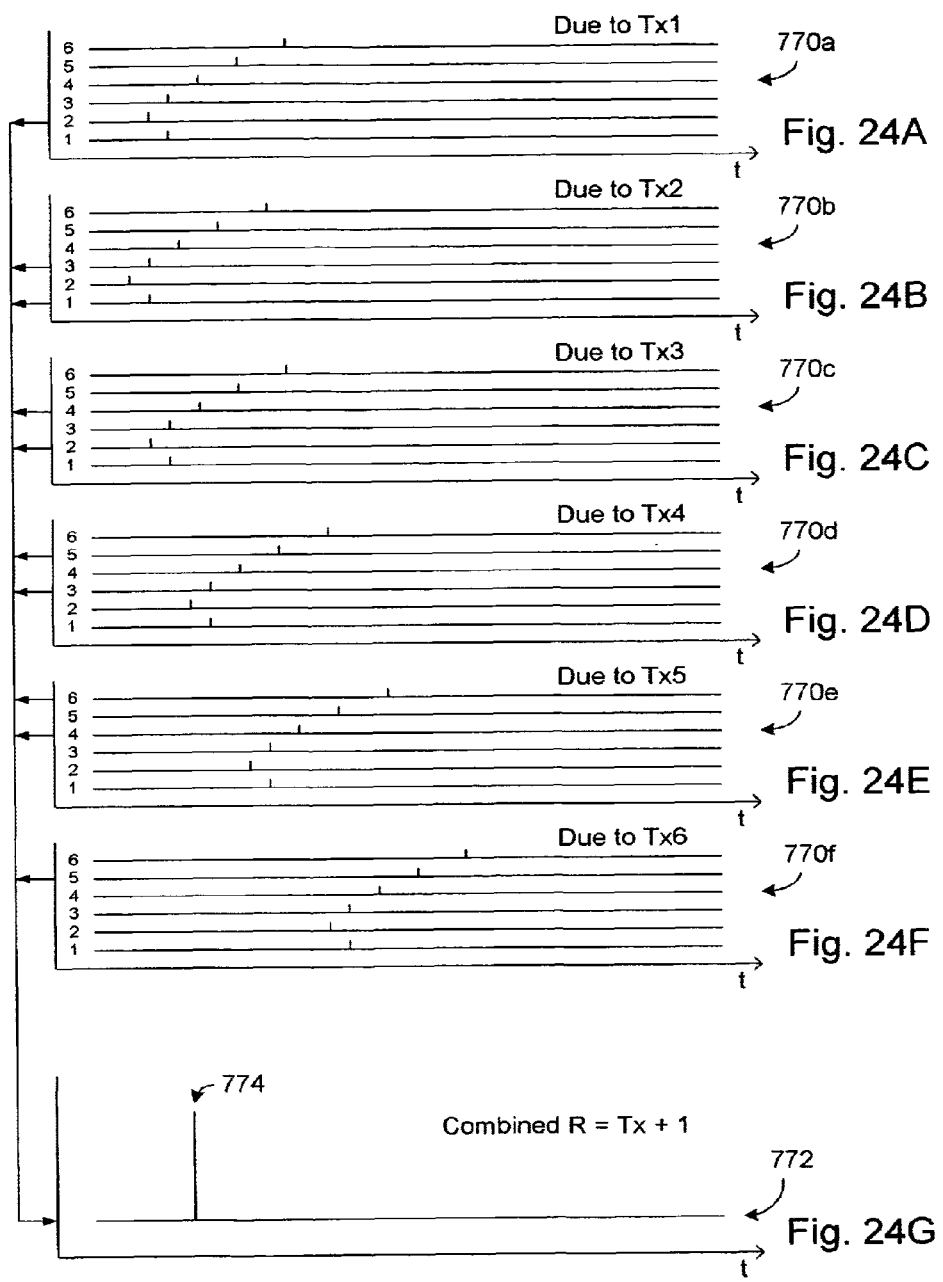

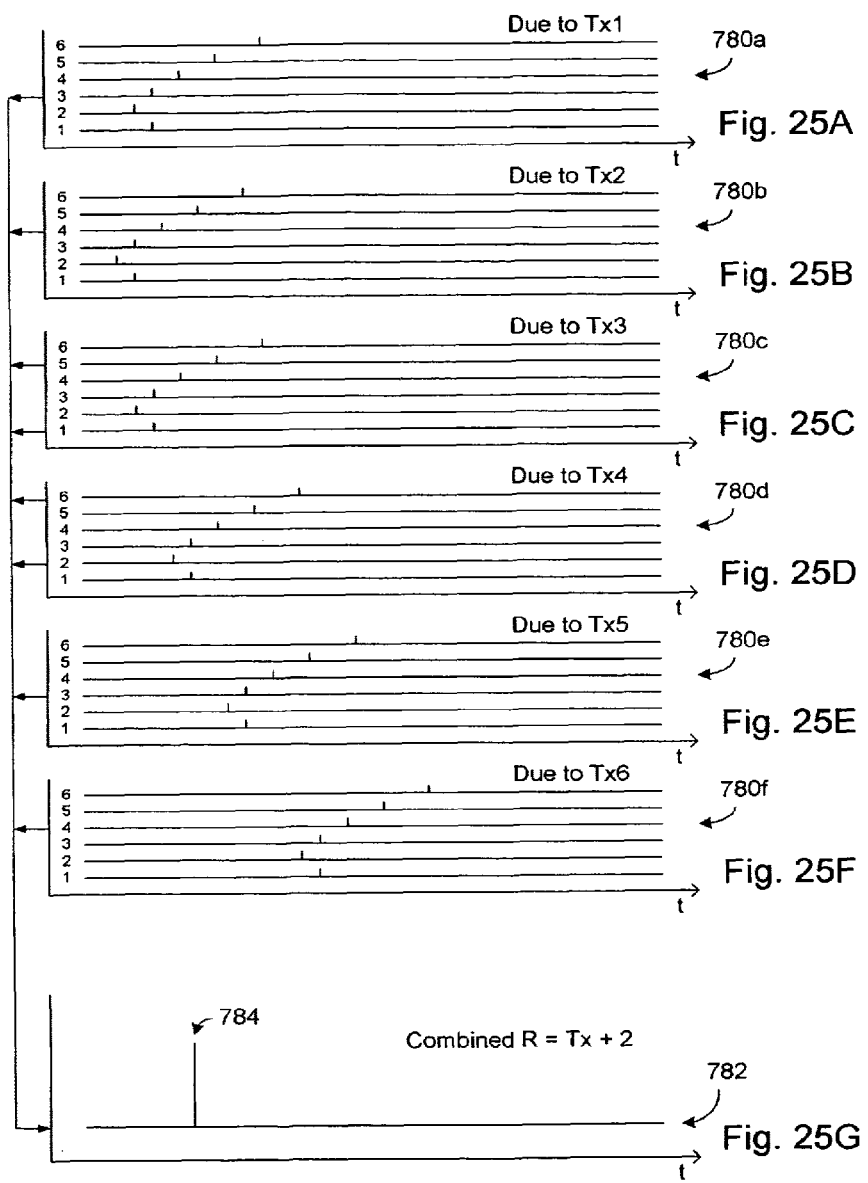

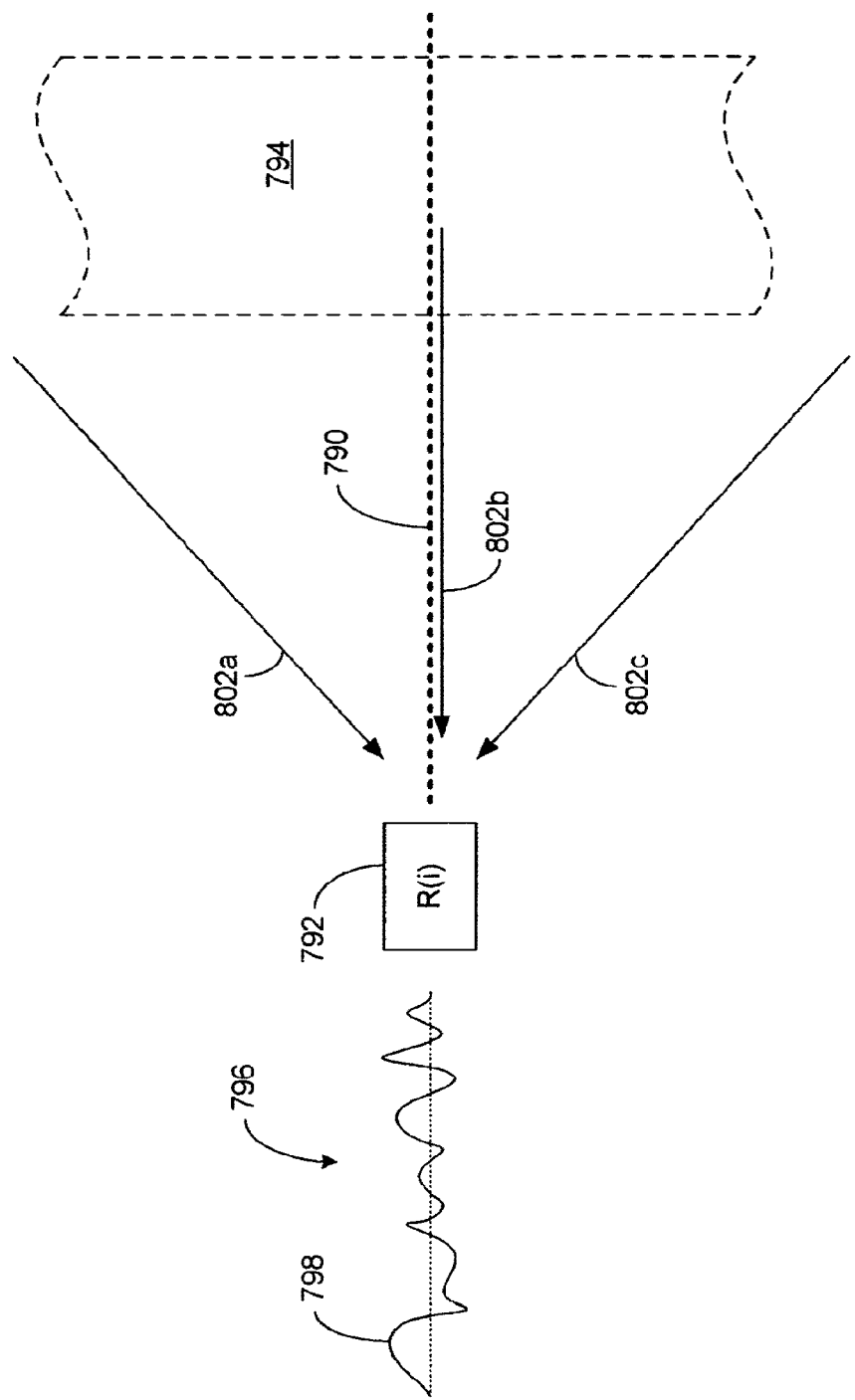

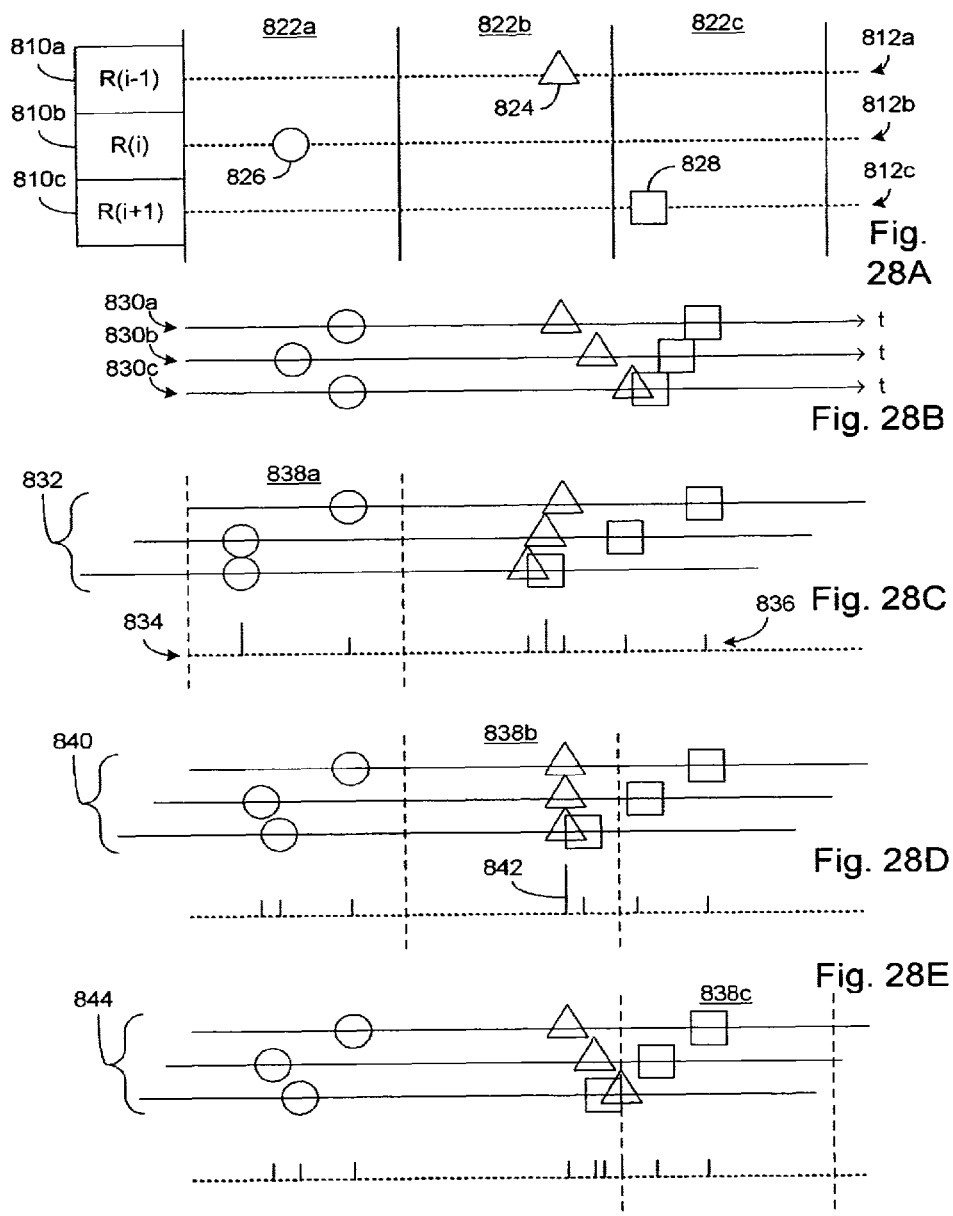

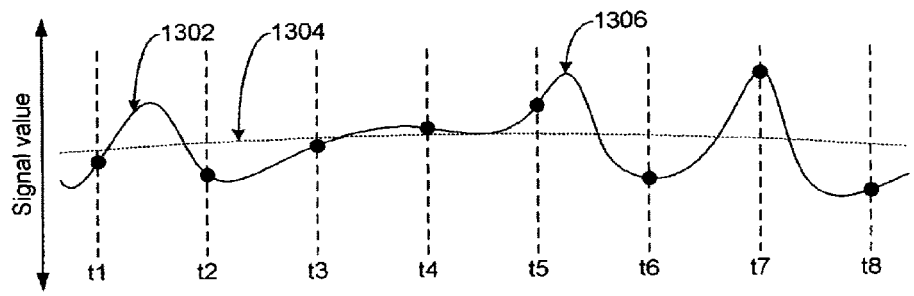
Fig. 37
| Sample time | Signal value | Sampled value |
|---|---|---|
| t1 | S1 | D1 |
| t2 | S2 | D2 |
| t3 | S3 | D3 |
| t4 | S4 | D4 |
| t5 | S5 | D5 |
| t6 | S6 | D6 |
| t7 | S7 | D7 |
| t8 | S8 | D8 |
Fig. 38
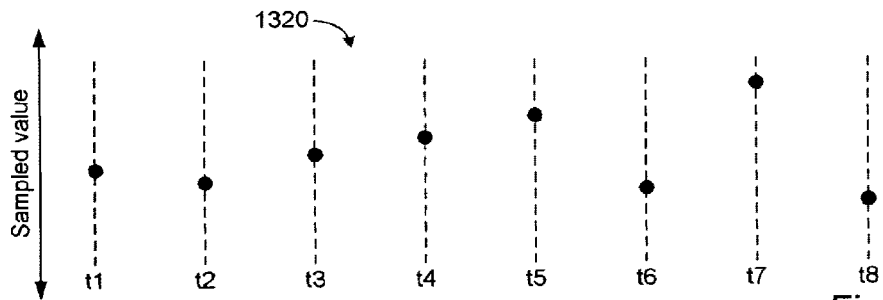
Fig. 39

SYSTEMS AND METHODS FOR ULTRASOUND IMAGING

RELATED APPLICATIONS

This application is a continuation of U.S. patent application Ser. No. 12/950,341, filed Nov. 19, 2010, now U.S. Pat. No. 8,234,923 on Aug. 7, 2012, which is a continuation-in-part of U.S. patent application Ser. No. 11/385,482, filed 20 Mar. 2006 now U.S. Pat. No. 7,862,508, entitled "SYSTEMS AND METHODS FOR ULTRASOUND IMAGING", which is a continuation-in-part of U.S. patent application Ser. No. 11/314,139, filed 21 Dec. 2005 now U.S. Pat. No. 7,819,805, entitled "SUB-NYQUIST SAMPLING OF ACOUSTIC SIGNALS IN ULTRASOUND IMAGING", which is a continuation-in-part of U.S. patent application Ser. No. 10/945,459, filed 20 Sep. 2004 now U.S. Pat. No. 7,850,611, entitled "SYSTEMS AND METHODS FOR IMPROVED IMAGING", which are hereby incorporated by reference herein in their entirety.

BACKGROUND

1. Field

The present teachings generally relate to the field of imaging using waves and more particularly, to systems and methods for improving the resolution of images obtained by an array of transmitters and receivers.

2. Description of the Related Art

Imaging devices such as ultrasound devices transmit a signal into a medium, and measure reflections from various features in the medium. An image of a given feature can be reconstructed based on quantities such as intensity and frequency of the reflected signal from that feature. To form the image, one needs to somehow determine the relative location of the feature with respect to the imaging device, and in particular, to a location of a receiving element of the device.

Conventional ultrasound devices typically have an array of transmitter-receiver pairs. In operation, each pair only "sees" along a line, commonly referred to as a scanline, that extends from the pair into the medium. With such an assumption, a feature along that scanline can be brought into "focus" by determining the propagation times of the transmitted and reflected signals to and from the feature. A propagation time t can be calculated as $t=d/v$ where v is the velocity of the signal in the medium, and d is the distance of interest (e.g., from the feature to the receiver). The distance d can be determined by dividing the scanline into discrete elements in a predetermined manner, such that the location of each element is known. The velocity v can either be assumed as a constant in the medium, or can be calculated in a manner generally known in the art.

Based on such an operation, one can see that the resolution and quality of the image formed can be limited by the size of the scanline element. Even if the scanline element can be made arbitrarily small, the effective operation of obtaining an image from the device is subject to the intrinsic resolution of the transmitter-receiver pair, as well as the sampling criteria for yielding a meaningful result.

The intrinsic resolution of a detector can be expressed as depending on the ratio of the operating wavelength of the signal to the effective dimension of the detector (commonly referred to as a Rayleigh or Sparrow criteria). One can change such a resolution of the detector by either changing the wavelength and/or the effective dimension of the detector. For example, reducing the wavelength (increasing the frequency) and/or increasing the effective dimension of the detector can improve the resolution. However, such a change can be accompanied by undesired effects. For example, an increased frequency signal has a smaller penetration depth in ultrasound applications.

Furthermore, an increased operating frequency also forces the minimum sampling frequency. Commonly known as the Nyquist sampling criteria, a signal needs to be sampled at a frequency that is at least approximately twice the frequency of the operating signal to yield a meaningful result.

Because of the foregoing challenges and limitations, there is an ongoing need to improve the manner in which imaging devices are designed and operated.

SUMMARY

The foregoing needs can be addressed by systems and methods for improving the resolution and quality of an image formed by signals from an array of receivers. Multiple receivers introduce variations in arrival times that can be less than the period of an operating signal, and also less than the period associated with a sampling operation. Thus, multiple receivers allow sampling of fine features of reflected signals that would be considered beyond the resolution associated with the operating signal. Use of multiple receivers also provides an effective sampling rate that is greater than the sampling rate of an individual receiver. Similar advantages can be obtained using multiple transmitters. Such advantageous features can be used to obtain high resolution images of objects in a medium in applications such as ultrasound imaging.

In some embodiments, the present teachings relate to a method of imaging an object in a medium with ultrasound. The method includes transmitting acoustic energy from a transmitter to the object such that the acoustic energy becomes scattered. The method further includes receiving the scattered energy at a plurality of receivers so as to produce respective analog echo signals. The method further includes sampling the analog echo signals at a frequency of F, with each of the sampled analog echo signals includes substantial spectral frequency components above a frequency of F/2 and includes substantial nonnegative spectral frequency components below or at said frequency of F/2. Such sampling produces a respective plurality of digital echo signals. The method further includes combining the plurality of digital echo signals, with each of the digital echo signals being offset by time with respect to another of the digital echo signals, so as to produce a combined digital signal that is selected from a plurality of different combinations of the plurality of digital echo signals. The method further includes producing an image pixel of the object from the combined digital signal.

In one embodiment, the method further includes producing a plurality of image pixels from the plurality of different combinations of the plurality of digital echo signals. The plurality of pixels distinctly depicts two objects in the medium that are closer together than 4F divided into an average velocity of sound in the medium. In one embodiment, such a method can distinctly depict two objects in the medium that are closer together than approximately 100 micrometers when the acoustic energy has a central peak frequency of approximately 3.5 MHz. In one embodiment, the acoustic energy propagates in the medium with an average velocity of approximately 1540 m/s.

In one embodiment of the method, the substantial spectral frequency components above a frequency of F/2 include a higher frequency having an intensity that is above a predetermined value. Such a predetermined value can have different values, such as 50 dB, 40 dB, 30 dB, 20 dB, 10 dB, or 10 dB less than a maximum intensity of the spectral frequency components of one of the sampled analog echo signals.

In one embodiment of the method, the step of combining the plurality of digital echo signals includes selecting a first digital echo signal associated with a first receiver. The step further includes performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the method, the step of combining the plurality of digital echo signals further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment of the method, the step of combining the plurality of digital echo signals further includes splitting a parent layer into two or more sublayers and performing time-shift combinations on each of the sublayers. The step further includes determining a best quality value for each of the sublayers. The step further includes comparing a best quality value of the parent layer to the best quality value of each of the sublayers. If the best quality value of the parent layer is substantially less than the best quality value of each of the sublayers, then the step further includes continuing to divide each of the sublayers into final sublayers, where each of the best quality values of the final sublayers is less than the best quality value of a parent layer of the final sublayers. In one embodiment, the step further includes assigning a combined digital signal of the parent layer of the final sublayers to the scanline.

In one embodiment of the method, the scanline is divided into a plurality of layers, and determinations of the particular qualities of the combinations are performed successively starting from a layer closest to the receiver.

In one embodiment of the method, combining of the plurality of digital echo signals substantially negates the effects, of aliasing within at least the sampled analog echo signals.

In some embodiments, the present teachings relate to a method of imaging an object with ultrasound. The method includes providing an array of transmitters $Tx(i)$, where i represents a relative positional index that ranges from 1 to N, and where N is greater than or equal to 2. The method further includes providing an array of receivers $Rx(i)$, where each of the receivers $Rx(i)$ associated with a respective transmitter $Tx(i)$. The method further includes transmitting ultrasound energy from the transmitters to the object such that the ultrasound energy is scattered. The method further includes receiving scattered energy at every receiver $Rx(i+j)$ that was transmitted from transmitter $Tx(i)$, where j represents a relative positional offset from i, and where j is greater than zero. The method further includes generating a first plurality of signals in response to the scattered energies received at every receiver $Rx(i+j)$. The method further includes combining the plurality of signals so as to produce an image of the object.

In one embodiment the method, the value of j is one. In one embodiment, the method further includes receiving scattered energy at every receiver $Rx(i+k)$ that was transmitted from transmitter $Tx(i)$, where k represents a relative positional offset from i, and where k is greater than zero and is not equal to j. The method further includes generating a second plurality of signals in response to the scattered energies received at every receiver $Rx(i+j)$ and $Rx(i+k)$. The method further includes combining the first and second pluralities of signals so as to produce an image of the object.

In some embodiments, the present teachings relate to an ultrasound imaging apparatus that includes a plurality of transmitters configured to transmit acoustic energy to one or more objects in a medium such that the acoustic energy becomes scattered. The apparatus further includes a plurality of receivers configured to receive the scattered energy and in response produce respective analog echo signals. The apparatus further includes a processor that is configured to facilitate sampling of the analog echo signals at a frequency of F, where each of the sampled analog echo signals includes substantial spectral frequency components above a frequency of $F/2$ and includes substantial nonnegative spectral frequency components below or at said frequency of $F/2$. The sampling produces a respective plurality of digital echo signals. The processor further facilitates combining of the plurality of digital echo signals, with each of the digital echo signals being offset by time with respect to another of the digital echo signals, so as to produce a combined digital signal that is selected from a plurality of different combinations of the plurality of digital echo signals. The processor further facilitates production of an image pixel of the object from the combined digital signal.

In one embodiment of the apparatus, the processor further facilitates production of a plurality of image pixels from the plurality of different combinations of the plurality of digital echo signals. The plurality of pixels distinctly depict two objects in the medium that are closer together than 4F divided into an average velocity of sound in the medium. In one embodiment, such an apparatus can distinctly depict two objects in the medium that are closer together than approximately 100 micrometers when the acoustic energy has a central peak frequency of approximately 3.5 MHz. In one embodiment, the acoustic energy propagates in the medium with an average velocity of approximately 1540 m/s.

In one embodiment of the apparatus, the substantial spectral frequency components above a frequency of $F/2$ include a higher frequency having an intensity that is above a predetermined value. Such a predetermined value can have different values, such as 50 dB, 40 dB, 30 dB, 20 dB, 10 dB, or 10 dB less than a maximum intensity of the spectral frequency components of one of the sampled analog echo signals.

In one embodiment of the apparatus, the processor facilitates combining of the plurality of digital echo signals by a process that selects a first digital echo signal associated with a first receiver. The process further performs a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the apparatus, the process further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of one of the plurality of combinations.

In one embodiment of the apparatus, the process further includes splitting a parent layer into two or more sublayers, and performing time-shift combinations on each of the sublayers. The process further includes determining a best quality value for each of the sublayers. The process further includes comparing a best quality value of the parent layer to the best quality value of each of the sublayers. If the best quality value of the parent layer is substantially less than the best quality value of each of the sublayers, then the process continues to divide each of the sublayers into final sublayers. Each of the best quality values of the final sublayers is less than the best quality value of a parent layer of the final sublayers.

In one embodiment of the apparatus, the process further includes a combined digital signal of the parent layer of the final sublayers to the scanline. In one embodiment, the scanline is divided into a plurality of layers, and the determinations of the particular qualities of the combinations are performed successively starting from a layer closest to the receiver.

In some embodiments, the present teachings relate to an ultrasound imaging apparatus that includes a transducer assembly having a plurality of transmitting elements and a plurality of receiving elements. The plurality of transmitting elements are configured to transmit ultrasound energy, having a wavelength $\lambda$ corresponding to a central peak frequency of the ultrasound energy, toward a region in a medium. The plurality of receiver elements generate a plurality of signals in response to scattered energy from the region. An aperture size D of the transducer assembly is the maximum distance between any two receiving elements in the transducer assembly. The apparatus further includes a processor configured to sample the plurality of signals to produce a plurality of corresponding digital echo signals. The processor is further configured to combine the plurality of digital echo signals to generate an image having a spatial resolution limit that is equal to or better than $\theta=(0.25)\lambda/D$, where $\theta$ is the minimum resolvable angular separation of two objects in the medium.

In one embodiment of the apparatus, the spatial resolution limit allows resolving of two objects in the medium that are closer together than approximately 100 micrometers when the ultrasound energy has a central peak frequency of approximately 3.5 MHz. In one embodiment, the acoustic energy propagates in the medium with an average velocity of approximately 1540 m/s. In one embodiment, the processor combines the plurality of digital echo signals by a process that includes selecting a first digital echo signal associated with a first receiver, and performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the apparatus, the process further includes assigning one of the plurality of combinations having a particular quality value to a scanline for the first receiver.

In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment of the apparatus, the process further includes splitting a parent layer into two or more sublayers, and performing time-shift combinations on each of the sublayers. The process further includes determining a best quality value for each of the sublayers. The process further includes comparing a best quality value of the parent layer to the best quality value of each of the sublayers. If the best quality value of the parent layer is substantially less than the best quality value of each of the sublayers, then the process further includes continuing to divide each of the sublayers into final sublayers, where each of the best quality values of the final sublayers is less than the best quality value of a parent layer of the final sublayers.

In one embodiment of the apparatus, the process further includes assigning a combined digital signal of the parent layer of the final sublayers to the scanline. In one embodiment, the scanline is divided into a plurality of layers, and determinations of the particular qualities of the combinations are performed successively starting from a layer closest to the receiver.

In some embodiments, the present teachings relate to a method of imaging with ultrasound. The method includes transmitting ultrasound energy, having a wavelength $\lambda$, corresponding to a central peak frequency of the ultrasound energy, from a plurality of transmitters in a transducer assembly into a medium such that the transmission energy is scattered. An aperture size D of the transducer assembly is the maximum distance between any two transmitters in the transducer assembly. The method further includes receiving scattered energies from the medium at a plurality of receivers. The method further includes digitally combining signals generated from the scattered energies so as to produce an image having a spatial resolution limit that is equal to or better than $\theta=(0.25)\lambda/D$, where $\theta$ is the minimum resolvable angular separation of two objects in the medium.

In one embodiment of the method, the spatial resolution limit allows resolving of the two objects in the medium that are closer together than approximately 100 micrometers when the ultrasound energy has a central peak frequency of approximately 3.5 MHz. In one embodiment, the acoustic energy propagates in the medium with an average velocity of approximately 1540 m/s. In one embodiment, the step of digitally combining the signals includes digitally sampling the signals so as to produce a plurality of digital echo signals. The step further includes selecting a first digital echo signal associated with a first receiver. The step further includes performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment of the method, the step of digitally combining the signals further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment, the method further includes splitting a parent layer into two or more sublayers, and performing time-shift combinations on each of the sublayers. The method further includes determining a best quality value for each of the sublayers. The method further includes comparing a best quality value of the parent layer to the best quality value of each of the sublayers. If the best quality value of the parent layer is substantially less than the best quality value of each of the sublayers, then the method further includes continuing to divide each of the sublayers into final sublayers. Each of the best quality values of the final sublayers is less than the best quality value of a parent layer of the final sublayers. In one embodiment, the method further includes assigning a combined digital signal of the parent layer of the final sublayers to the scanline.

In one embodiment of the method, the scanline is divided into a plurality of layers, and determinations of the particular qualities of the combinations are performed successively starting from a layer closest to the receiver.

In some embodiments, the present teachings relate to a method of replicating information from a waveform energy emanating from an object over time, where the information includes a spectral frequency distribution having frequency components above a frequency F/2. The method includes digitally sampling the waveform energy at a temporal frequency of less than F to obtain sampled data. The method further includes producing a replica of the information from the sampled data, where the replica includes a spectral frequency distribution that substantially matches the spectral frequency distribution in a range below the frequency F/2. The energy is emitted from a plurality of emitters and is reflected from the object.

In one embodiment of the method, the energy is sampled with a plurality of detectors. In one embodiment, the energy is acoustic energy. In one embodiment, the energy is electromagnetic energy.

In some embodiments, the present teachings relate to an ultrasound imaging apparatus having a plurality of transmitters configured to transmit acoustic energy to an object in a medium such that the acoustic energy becomes scattered. The apparatus further includes a plurality of receivers configured to receive the scattered energy and in response produce respective analog echo signals. The apparatus further includes a sampling module configured to sample the analog echo signals at a frequency of F. Each of the sampled analog echo signals includes substantial spectral frequency components above a frequency of F/2 and includes substantial non-negative spectral frequency components below or at the frequency of F/2. The sampling produces a respective plurality of digital echo signals. The apparatus further includes a combining module configured to combine the plurality of digital echo signals. Each of the digital echo signals is offset by time with respect to another of the digital echo signals, so as to produce a combined digital signal that is selected from a plurality of different combinations of the plurality of digital echo signals. The apparatus further includes an image producing module configured to produce an image pixel of the object from the combined digital signal.

In one embodiment, the image producing module further produces a plurality of image pixels from the plurality of different combinations of the plurality of digital echo signals, with the plurality of pixels distinctly depicting two objects in the medium that are closer together than 4F divided into an average velocity of sound in the medium. In one embodiment, the two objects in the medium are closer together than approximately 100 micrometers when the acoustic energy has a central peak frequency of approximately 3.5 MHz. In one embodiment, the acoustic energy propagates in the medium with an average velocity of approximately 1540 m/s.

In one embodiment, the substantial spectral frequency components above a frequency of F/2 include a higher frequency having an intensity that is above a predetermined value. In one embodiment, the predetermined value is 50 dB less than a maximum intensity of the spectral frequency components of one of the sampled analog echo signals. In one embodiment, the predetermined value is 40 dB less than a maximum intensity of the spectral frequency components of one of the sampled analog echo signals. In one embodiment, the predetermined value is 30 dB less than a maximum intensity of the spectral frequency components of one of the sampled analog echo signals. In one embodiment, the predetermined value is 20 dB less than a maximum intensity of the spectral frequency components of one of the sampled analog echo signals. In one embodiment, the predetermined value is 10 dB less than a maximum intensity of the spectral frequency components of one of the sampled analog echo signals. In one embodiment, the predetermined value is 5 dB less than a maximum intensity of the spectral frequency components of one of the sampled analog echo signals.

In one embodiment, the combining module combines the plurality of digital echo signals by a process that includes selecting a first digital echo signal associated with a first receiver; and performing a plurality of time-shift combinations of the first digital echo signal with one or more digital echo signals associated with one or more other receivers about a selected time window of the first signal. Each of the plurality of combinations has a quality value indicative of a quality of the combination.

In one embodiment, the process performed by the combining module further includes assigning one of the plurality of combinations having a particular quality value to a scanline for the first receiver. In one embodiment, the selected time window corresponds to a layer having a first thickness along the scanline. In one embodiment, the particular quality value includes a running average of an amplitude of the one of the plurality of combinations. In one embodiment, the particular quality value includes a slope of a running average of an amplitude with respect to time of the one of the plurality of combinations.

In one embodiment, the process performed by the combining module further includes splitting a parent layer into two or more sublayers; performing time-shift combinations on each of the sublayers; determining a best quality value for each of the sublayers; comparing a best quality value of the parent layer to the best quality value of each of the sublayers; and if the best quality value of the parent layer is substantially less than the best quality value of each of the sublayers, then continuing to divide each of the sublayers into final sublayers. Each of the best quality values of the final sublayers is less than the best quality value of a parent layer of the final sublayers. In one embodiment, the process further includes assigning a combined digital signal of the parent layer of the final sublayers to the scanline.

In one embodiment, the scanline is divided into a plurality of layers. Determinations of the particular qualities of the combinations are performed successively starting from a layer closest to the receiver.

In one embodiment, the sampling module includes an analog-to-digital converter. In one embodiment, the sampling module includes a processor. In one embodiment, the processor includes a single unit configured to perform one or more processes. In one embodiment, the processor includes a plurality of separate units configured to perform one or more processes.

In one embodiment, the combining module includes a processor. In one embodiment, the processor includes a single unit configured to perform one or more processes. In one embodiment, the processor includes a plurality of separate units configured to perform one or more processes.

In one embodiment, combining of the plurality of digital echo signals substantially negates the effects of aliasing within at least the sampled analog echo signals.

One embodiment of the present disclosure relates to an ultrasound imaging apparatus that includes a sampling module configured to sample, at a frequency of F, a plurality of analog echo signals received from a respective plurality of receivers. Each of the sampled analog echo signals includes substantial spectral frequency components above a frequency of F/2 and includes substantial nonnegative spectral frequency components below or at the frequency of F/2. The sampling produces a respective plurality of digital echo signals. The apparatus further includes a combining module configured to combine the plurality of digital echo signals. Each of the digital echo signals is offset by time with respect to another of the digital echo signals, so as to produce a combined digital signal that is selected from a plurality of different combinations of the plurality of digital echo signals. The apparatus further includes an image-producing module configured to produce an image pixel of an object from the combined digital signal.

One embodiment of the present disclosure relates to an ultrasound imaging apparatus having a plurality of sampling modules. Each sampling module is configured to sample, at a frequency of F, an analog echo signal received from a receiver. Each of the sampled analog echo signals includes substantial spectral frequency components above a frequency of F/2 and includes substantial nonnegative spectral frequency components below or at the frequency of F/2. The plurality of sampling modules produces a respective plurality of digital echo signals. The apparatus further includes a combining module configured to combine the plurality of digital echo signals. Each of the digital echo signals is offset by time with respect to another of the digital echo signals, so as to produce a combined digital signal that is selected from a plurality of different combinations of the plurality of digital echo signals. The apparatus further includes an image-producing module configured to produce an image pixel of an object from the combined digital signal.

One embodiment of the present disclosure relates to an ultrasound imaging apparatus having a plurality of means for sampling, with each means for sampling configured to sample, at a frequency of F, an analog echo signal received from a receiver. Each of the sampled analog echo signals includes substantial spectral frequency components above a frequency of F/2 and includes substantial nonnegative spectral frequency components below or at the frequency of F/2. The plurality of means for sampling produces a respective plurality of digital echo signals. The apparatus further includes means for combining the plurality of digital echo signals, with each of the digital echo signals being offset by time with respect to another of the digital echo signals, so as to produce a combined digital signal that is selected from a plurality of different combinations of the plurality of digital echo signals. The apparatus further includes means for producing an image pixel of an object from the combined digital signal.

One embodiment of the present disclosure relates to an ultrasound imaging apparatus having a plurality of transmitters configured to transmit acoustic energy to an object in a medium such that said acoustic energy becomes scattered. The apparatus further includes a plurality of receivers configured to receive said scattered energy and in response produce respective analog echo signals. The apparatus further includes a plurality of sampling modules, with each configured to sample, at a frequency of F, a corresponding one of said plurality of analog echo signals. Each of said sampled analog echo signals includes substantial spectral frequency components above a frequency of F/2 and includes substantial nonnegative spectral frequency components below or at said frequency of F/2. The plurality of sampling modules produces a respective plurality of digital echo signals. The apparatus further includes a combining module configured to combine said plurality of digital echo signals, with each of said digital echo signals being offset by time with respect to another of said digital echo signals, so as to produce a combined digital signal that is selected from a plurality of different combinations of said plurality of digital echo signals. The apparatus further includes an image producing module configured to produce an image pixel of said object from said combined digital signal.

One embodiment of the present disclosure relates to an ultrasound apparatus that includes a plurality of transmitters configured to transmit acoustic energy to a tissue of an animal having an anatomy through a coupling medium, such that the acoustic energy becomes scattered by an object in the tissue. The apparatus further includes a plurality of receivers configured to receive the scattered energy and produce respective analog echo signals. The apparatus further includes a signal processing component configured to digitize the analog echo signals so as to produce respective digitized signals. The apparatus further includes a processing module configured so as to calculate a plurality of first indices. Each of the plurality of first indices represents a travel time of the acoustic energy along an assumed path from a transmitter to a voxel in a proposed image plane and from the voxel to a receiver. The processing module is further configured so as to produce a first set of object data by combining first selected portions of the digitized signals. Each of the first selected portions is determined based on the plurality of first indices. The processing module is further configured so as to determine a location of a skin surface of the anatomy. The skin surface represents a scattering interface. The processing module is further configured so as to calculate a plurality of second indices for the voxels in the proposed image plane. The voxels are located on the opposite side of the skin surface with respect to the plurality of transmitters. Each of the plurality of second indices is determined by an adjustment to at least one of the plurality of first indices due to refraction of the acoustic energy at the scattering interface. The adjustment is determined based on assumed sound speeds in the coupling medium and in the tissue between the scattering interface and the object. The processing module is further configured so as to produce a second set of object data by combining second selected portions of the digitized signals. Each of the second selected portions determined based on the plurality of second indices.

In one embodiment, the tissue includes a human breast.

In one embodiment, the processing module is further configured to re-calculate the plurality of second indices and re-produce the second set of object data by obtaining an optimized focus while varying the speed of sound between the scattering interface and the object. In one embodiment, the optimized focus includes a maximized contrast in a boundary or a reflector within the tissue. In one embodiment, the processing module is further configured to calculate a plurality of additional indices and produce one or more additional sets of object data corresponding to a plurality of layers within the tissue between the scattering interface and the object.

In one embodiment, the scattering interface is the closest scattering interface with respect to the transmitters and receivers.

In one embodiment, the assumed path includes a substantially straight path.

In one embodiment, the refraction is determined according to Snell's law of refraction.

In one embodiment, the refraction is determined in three dimensions.

In one embodiment, at least one of the plurality of transmitters includes a physical transducer that is part of an array of similar transducers.

In one embodiment, at least one of the plurality of transmitters includes a transducer or a point source that is virtual, having been created by the timed firing of part or all of an array of physical transducers.

In one embodiment, the apparatus further includes an image producing module that produces an image of the object based on the second set of object data.

The signal processing component can include, for example, an analog-to-digital converter (ADC). The processing module can include one or more devices, one or more processes, or any combination thereof. The processing module can also include one or more hardware components, one or more software components, or any combination thereof. Similarly, the image producing module can include one or more devices, one or more processes, or any combination thereof, and can include a still-image generating device, a video-image generating device, or any combination thereof. The image producing module can also include one or more hardware components, one or more software components, or any combination thereof. Moreover, any combination of the signal processing component, processing module, and/or image producing module can be part of a single component, or be part of a plurality of components.

In one embodiment, the image producing module and the processing module form a single component. In one embodiment, the single component also includes the signal processing component.

In one embodiment, the signal processing component and the processing module form a single component.

One embodiment of the present disclosure relates to an ultrasound apparatus that includes a plurality of transmitters configured to transmit acoustic energy to a tissue of an animal having an anatomy through a coupling medium, such that the acoustic energy becomes scattered by an object in the tissue. The apparatus further includes a plurality of receivers configured to receive the scattered energy and produce respective analog echo signals. The apparatus further includes a signal processing component configured to digitize the analog echo signals so as to produce respective digitized signals. The apparatus further includes a processing module configured so as to estimate a tissue configuration, including positions of one or more boundaries between a plurality of regions and speeds of sound in each of the plurality of regions. Each of the plurality of regions has a thickness. The processing module is further configured so as to calculate a plurality of indices. Each of the plurality of indices represents a travel time of the acoustic energy from a transmitter to a voxel in a proposed image plane and from the voxel to a receiver. The travel time is determined based on refraction at each of the boundaries. The processing module is further configured so as to produce a set of object data by combining selected portions of the digitized signals. Each of the selected portions is determined based on the plurality of indices. The processing module is further configured so as to repeat the calculation of the plurality of indices and the production of the set of object data while varying, for at least one of the plurality of regions, at least one of thickness and speed of sound, until a desired quality for the set of object data for the tissue is obtained.

In one embodiment, the tissue includes a human liver.

In one embodiment, the first two of the plurality of regions are assumed to be human skin and human fat.

In one embodiment, the desired data quality is obtained by obtaining an optimized focus while varying the speed of sound in each of the plurality of regions. In one embodiment, the optimized focus includes maximized contrast in a boundary or a reflector within the tissue. In one embodiment, the processing module is further configured to divide one or more of the plurality of regions into a plurality of layers and perform the production of set of object data for each of the layers.

In one embodiment, the apparatus further includes an image producing module that produces an image of the tissue based on the set of object data having the desired quality.

In one embodiment, the image producing module and the processing module form a single component. In one embodiment, the single component also includes the signal processing component.

In one embodiment, the signal processing component and the processing module form a single component.

In one embodiment, the processing module is configured to make use of a previous estimation of a tissue configuration including positions of one or more boundaries between a plurality of regions and speeds of sound in each of the plurality of regions, with each of the plurality of regions having a thickness.

The signal processing component can include, for example, an analog-to-digital converter (ADC). The processing module can include one or more devices, one or more processes, or any combination thereof. The processing module can also include one or more hardware components, one or more software components, or any combination thereof. Similarly, the image producing module can include one or more devices, one or more processes, or any combination thereof, and can include a still-image generating device, a video-image generating device, or any combination thereof. The image producing module can also include one or more hardware components, one or more software components, or any combination thereof. Moreover, any combination of the signal processing component, processing module, and/or image producing module can be part of a single component, or be part of a plurality of components.

One embodiment of the present disclosure relates to an ultrasound apparatus that includes a plurality of transmitters configured to transmit acoustic energy to a tissue of an animal having an anatomy through a coupling medium, such that the acoustic energy becomes scattered by an object in the tissue. The apparatus further includes a plurality of receivers configured to receive the scattered energy and produce respective analog echo signals. The apparatus further includes a signal processing component configured to digitize the analog echo signals so as to produce respective digitized signals. The apparatus further includes a processing module configured so as to calculate a plurality of indices. Each of the plurality of indices represents a travel time of the acoustic energy from a transmitter to a voxel in a proposed image plane and from the voxel to a receiver. The travel time is determined based on assumed constant speeds of sound in the coupling medium and in the tissue. The processing module is further configured so as to obtain a first optimized focus within a field of view of the tissue while varying the speed of sound in the tissue. The processing module is further configured so as to postulate the presence of a boundary within the field of view so as to form two layers having thicknesses on both sides of the boundary. The processing module is further configured so as to obtain a second optimized focus within the two layers while varying the thicknesses and speeds of sound in the two layers. The processing module is further configured so as to compare the first and second optimized focuses, and discard the second optimized focus if the second optimized focus is not better than the first optimized focus.

In one embodiment, the processing module is further configured such that the two layers are further split and focus optimized to find a best focused set of layer thicknesses and sound speeds.

The signal processing component can include, for example, an analog-to-digital converter (ADC). The processing module can include one or more devices, one or more processes, or any combination thereof. The processing module can also include one or more hardware components, one or more software components, or any combination thereof. Moreover, any combination of the signal processing component, and/or processing module can be part of a single component, or be part of a plurality of components.

One embodiment of the present disclosure relates to an ultrasound for imaging a generally layered portion of anatomy. The apparatus includes a plurality of transmitters configured to transmit acoustic energy to a tissue of an animal having an anatomy through a coupling medium, such that the acoustic energy becomes scattered by an object in the tissue. The apparatus further includes a plurality of receivers configured to receive the scattered energy and produce respective analog echo signals. The apparatus further includes a signal processing component configured to digitize the analog echo signals so as to produce respective digitized signals. The apparatus further includes a processing module configured so as to estimate a speed of sound in a first layer encountered by the acoustic energy. The processing module is further configured so as to calculate a plurality of indices. Each of the plurality of indices represents a travel time of the acoustic energy from a transmitter to a voxel in the first layer and from the voxel to a receiver, and construct a set of object data based on the plurality of indices. The processing module is further configured so as to obtain an optimized focus in the first layer while varying the speed of sound in the first layer. The processing module is further configured so as to determine a location of a first interface that forms a boundary between the first layer and a second layer. The first interface is determined based on the optimized focus in the first layer. The processing module is further configured so as to estimate a speed of sound in the second layer. The processing module is further configured so as to calculate a plurality of adjustments to the plurality of indices based on refraction across the first interface. The processing module is further configured so as to obtain an optimized focus in the second layer while varying the speed of sound in the second layer.

In one embodiment, the processing module is further configured to determine the location of one or more additional interfaces behind the first interface thereby forming one or more additional layers, and obtain respective optimized focus in each of the one or more additional layers based on variations of respective speeds of sound and adjustments based on refraction.

The signal processing component can include, for example, an analog-to-digital converter (ADC). The processing module can include one or more devices, one or more processes, or any combination thereof. The processing module can also include one or more hardware components, one or more software components, or any combination thereof. Moreover, any combination of the signal processing component and/or processing module can be part of a single component, or be part of a plurality of components.

One embodiment of the present disclosure relates to an ultrasound apparatus for imaging a portion of anatomy having distinct regions with different speeds of sound. The apparatus includes a plurality of transmitters configured to transmit acoustic energy to a tissue of an animal having an anatomy through a coupling medium, such that the acoustic energy becomes scattered by an object in the tissue. The apparatus further includes a plurality of receivers configured to receive the scattered energy and produce respective analog echo signals. The apparatus further includes a signal processing component configured to digitize the analog echo signals so as to produce respective digitized signals. The apparatus further includes a processing module configured so as to calculate a plurality of first indices. Each of the plurality of first indices represents a travel time of the acoustic energy along an assumed path from a transmitter to a voxel in the tissue and from the voxel to a receiver. The travel time is determined based on an estimated speed of sound in the tissue. The processing module is further configured so as to produce a first set of object data by combining first selected portions of the digitized signals. Each of the first selected portions is determined based on the first indices. The processing module is further configured so as to determine a location of one or more interfaces based on the first set of object data. The one or more interfaces define regions of interest in the tissue. The processing module is further configured so as to calculate plurality of second indices for voxels in the regions of interest. Each of the plurality of second indices is determined by an adjustment to at least one of the plurality of first indices due to refraction of the acoustic energy at the one or more interfaces. The adjustment is determined based on the estimated speed of sound. The processing module is further configured so as to produce a second set of object data by combining second selected portions of the digitized signals, with each of the second selected portions determined based on the plurality of second indices. The processing module is further configured so as to obtain an optimized object data by varying speed of sound in at least one of the regions of interest.

The signal processing component can include, for example, an analog-to-digital converter (ADC). The processing module can include one or more devices, one or more processes, or any combination thereof. The processing module can also include one or more hardware components, one or more software components, or any combination thereof. Moreover, any combination of the signal processing component and/or processing module can be part of a single component, or be part of a plurality of components.

One embodiment of the present disclosure relates to a method of imaging a portion of anatomy with ultrasound. The method includes, for each of a plurality of transmitters, transmitting acoustic energy from a transmitter to a tissue of an animal having an anatomy through a coupling medium such that the acoustic energy becomes scattered by an object in the tissue; receiving the scattered energy at a plurality of receivers so as to produce respective analog echo signals; and digitizing the analog echo signals so as to produce respective digitized signals. The method further includes calculating a plurality of first indices, with each of the plurality of first indices representing a travel time of the acoustic energy along an assumed path from a transmitter to a voxel in a proposed image plane and from the voxel to a receiver. The method further includes producing a first set of object data by combining first selected portions of the digitized signals, with each of the first selected portions determined based on the plurality of first indices. The method further includes determining a location of a skin surface of the anatomy, with the skin surface representing a scattering interface. The method further includes calculating a plurality of second indices for the voxels in the proposed image plane, with the voxels being located on the opposite side of the skin surface with respect to the plurality of transmitters, with each of the plurality of second indices determined by an adjustment to at least one of the plurality of first indices due to refraction of the acoustic energy at the scattering interface, with the adjustment determined based on assumed sound speeds in the coupling medium and in the tissue between the scattering interface and the object. The method further includes producing a second set of object data by combining second selected portions of the digitized signals, with each of the second selected portions determined based on the plurality of second indices.

In one embodiment, the tissue includes a human breast.

In one embodiment, the method further includes re-calculating the plurality of second indices and re-producing the second set of object data by obtaining an optimized focus while varying the speed of sound behind the scattering interface. In one embodiment, the optimized focus includes a maximized contrast in a boundary or a reflector within the tissue. In one embodiment, the method further includes calculating plurality of additional indices and producing one or more additional sets of object data corresponding to a plurality of layers within the tissue between the scattering interface and the object.

In one embodiment, the scattering interface is the closest scattering interface with respect to the transmitters and receivers.

In one embodiment, the assumed path includes a substantially straight path.

In one embodiment, the refraction is determined according to Snell's law of refraction.

In one embodiment, the refraction is determined in three dimensions.

In one embodiment, at least one of the plurality of transmitters includes a physical transducer that is part of an array of similar transducers.

In one embodiment, the method further includes producing an image of the object based on the second set of object data.

One embodiment of the present disclosure relates to a method of imaging a portion of anatomy with ultrasound. The method includes, for each of a plurality of transmitters, transmitting acoustic energy from a transmitter to a tissue of an animal having an anatomy through a coupling medium such that the acoustic energy becomes scattered by an object in the tissue; receiving the scattered energy at a plurality of receivers so as to produce respective analog echo signals; and digitizing the analog echo signals so as to produce respective digitized signals. The method further includes estimating a tissue configuration, including positions of one or more boundaries between a plurality of regions and speeds of sound in each of the plurality of regions, with each of the plurality of regions having a thickness. The method further includes calculating a plurality of indices, with each of the plurality of indices representing a travel time of the acoustic energy from a transmitter to a voxel in a proposed image plane and from the voxel to a receiver, with the travel time determined based on refraction at each of the boundaries. The method further includes producing a set of object data by combining selected portions of the digitized signals, with each of the selected portions determined based on the plurality of indices. The method further includes repeating the calculation of the plurality of indices and the production of the set of object data while varying, for at least one of the plurality of regions, at least one of thickness and speed of sound, until a desired quality for the set of object data for the tissue is obtained.

In one embodiment, the tissue of interest includes a human liver.

In one embodiment, the first two of the plurality of regions are assumed to be human skin and human fat.

In one embodiment, the desired data quality is obtained by obtaining an optimized focus while varying the speed of sound in each of the plurality of regions. In one embodiment, the optimized focus includes maximized contrast in a boundary or a reflector within the tissue. In one embodiment, the method further includes dividing one or more of the plurality of regions into a plurality of layers and performing the production of a set of object data for each of the layers.

In one embodiment, the method further includes producing an image of the tissue based on the set of object data having the desired quality.

One embodiment of the present disclosure relates to a method of imaging a portion of anatomy with ultrasound. The method includes, for each of a plurality of transmitters, transmitting acoustic energy from a transmitter to a tissue of an animal having an anatomy through a coupling medium such that the acoustic energy becomes scattered by an object in the tissue; receiving the scattered energy at a plurality of receivers so as to produce respective analog echo signals; and digitizing the analog echo signals so as to produce respective digitized signals. The method further includes calculating a plurality of indices, with each of the plurality of indices representing a travel time of the acoustic energy from a transmitter to a voxel in a proposed image plane and from the voxel to a receiver, with the travel time determined based on assumed constant speeds of sound in the coupling medium and in the tissue. The method further includes obtaining a first optimized focus within a field of view of the tissue while varying the speed of sound in the tissue. The method further includes postulating the presence of a boundary within the field of view so as to form two layers having thicknesses on both sides of the boundary. The method further includes obtaining a second optimized focus within the two layers while varying the thicknesses and speeds of sound in the two layers. The method further includes comparing the first and second optimized focuses, and discarding the second optimized focus if the second optimized focus is not better than the first optimized focus.

In one embodiment, the two layers are further split and focus optimized to find a best focused set of layer thicknesses and sound speeds.

One embodiment of the present disclosure relates to a method of imaging a generally layered portion of anatomy with ultrasound. The method includes, for each of a plurality of transmitters, transmitting acoustic energy from a transmitter to a tissue of an animal having an anatomy through a coupling medium such that the acoustic energy becomes scattered by an object in the tissue; receiving the scattered energy at a plurality of receivers so as to produce respective analog echo signals; and digitizing the analog echo signals so as to produce respective digitized signals. The method further includes estimating a speed of sound in a first layer encountered by the acoustic energy. The method further includes calculating a plurality of indices, with each of the plurality of indices representing a travel time of the acoustic energy from a transmitter to a voxel in the first layer and from the voxel to a receiver, and construct a set of object data based on the plurality of indices. The method further includes obtaining an optimized focus in the first layer while varying the speed of sound in the first layer. The method further includes determining a location of a first interface that forms a boundary between the first layer and a second layer, with the first interface determined based on the optimized focus in the first layer. The method further includes estimating a speed of sound in the second layer. The method further includes calculating a plurality of adjustments to the plurality of indices based on refraction across the first interface. The method further includes obtaining an optimized focus in the second layer while varying the speed of sound in the second layer.

In one embodiment, the method further includes determining location of one or more additional interfaces behind the first interface thereby forming one or more additional layers, and obtaining respective optimized focus in each of the one or more additional layers based on variations of respective speeds of sound and adjustments based on refraction.

One embodiment of the present disclosure relates to a method of using ultrasound to image a portion of anatomy having distinct regions with different speeds of sound. The method includes, for each of a plurality of transmitters, transmitting acoustic energy from a transmitter to a tissue of an animal having an anatomy through a coupling medium such that the acoustic energy becomes scattered by an object in the tissue; receiving the scattered energy at a plurality of receivers so as to produce respective analog echo signals; and digitizing the analog echo signals so as to produce respective digitized signals. The method further includes calculating a plurality of first indices, with each of the plurality of first indices representing a travel time of the acoustic energy along an assumed path from a transmitter to a voxel in the tissue and from the voxel to a receiver, with the travel time determined based on an estimated speed of sound in the tissue. The method further includes producing a first set of object data by combining first selected portions of the digitized signals, with each of the first selected portions determined based on the first indices. The method further includes determining a location of one or more interfaces based on the first set of object data, with the one or more interfaces defining regions of interest in the tissue. The method further includes calculating plurality of second indices for voxels in the regions of interest, with each of the plurality of second indices determined by an adjustment to at least one of the plurality of first indices due to refraction of the acoustic energy at the one or more interfaces, with the adjustment determined based on the estimated speed of sound. The method further includes producing a second set of object data by combining second selected portions of the digitized signals, with each of the second selected portions determined based on the plurality of second indices. The method further includes obtaining an optimized object data by varying speed of sound in at least one of the regions of interest.

BRIEF DESCRIPTION OF THE DRAWINGS

FIG. 7 shows a process for obtaining a set of indices separately for transmitters and receivers for a given an array of pixels;

FIG. 8 shows a process for using the indices to selectively sample signals obtained by one or more receivers;

FIGS. 24A-F show a simplified depiction of example digitized data trace from the example signal traces of FIGS. 23A and B;

FIG. 24G shows an example of a combination of digitized data associated with receivers that are offset by one from their respective transmitters;

FIGS. 25A-F show a simplified depiction of example digitized data trace from the example signal traces of FIGS. 23A and B;

FIG. 25G shows an example of a combination of digitized data associated with receivers that are offset by two from their respective transmitters;

FIG. 26 shows how a signal from a given receiver can be combined with signal(s) from other receiver(s) to form a scanline for the given receiver such that the scanline has an improved performance for imaging a given layer;

FIG. 28A shows an example of features located along different scanlines and in different layers;

FIG. 28B shows an example of measured signal traces having components associated with the example features of FIG. 28A;

FIGS. 28C-E show by example "in-focus" combinations at various layers for the signals traces to form the scanline associated with the first example receiver;

FIG. 37 shows an example analog echo signal, having one or more relatively fine features, being sampled periodically;

FIG. 38 shows an example table of signal values and the corresponding sampled values at example sampling times of the example analog signal of FIG. 37;

FIG. 39 shows an example plot of the sampled values analog signal of FIG. 37, showing that such sampling can be susceptible to aliasing effects;

These and other aspects, advantages, and novel features of the present teachings will become apparent upon reading the following detailed description and upon reference to the accompanying drawings. In the drawings, similar elements have similar reference numerals.

DETAILED DESCRIPTION OF SOME EMBODIMENTS

Figure 1:
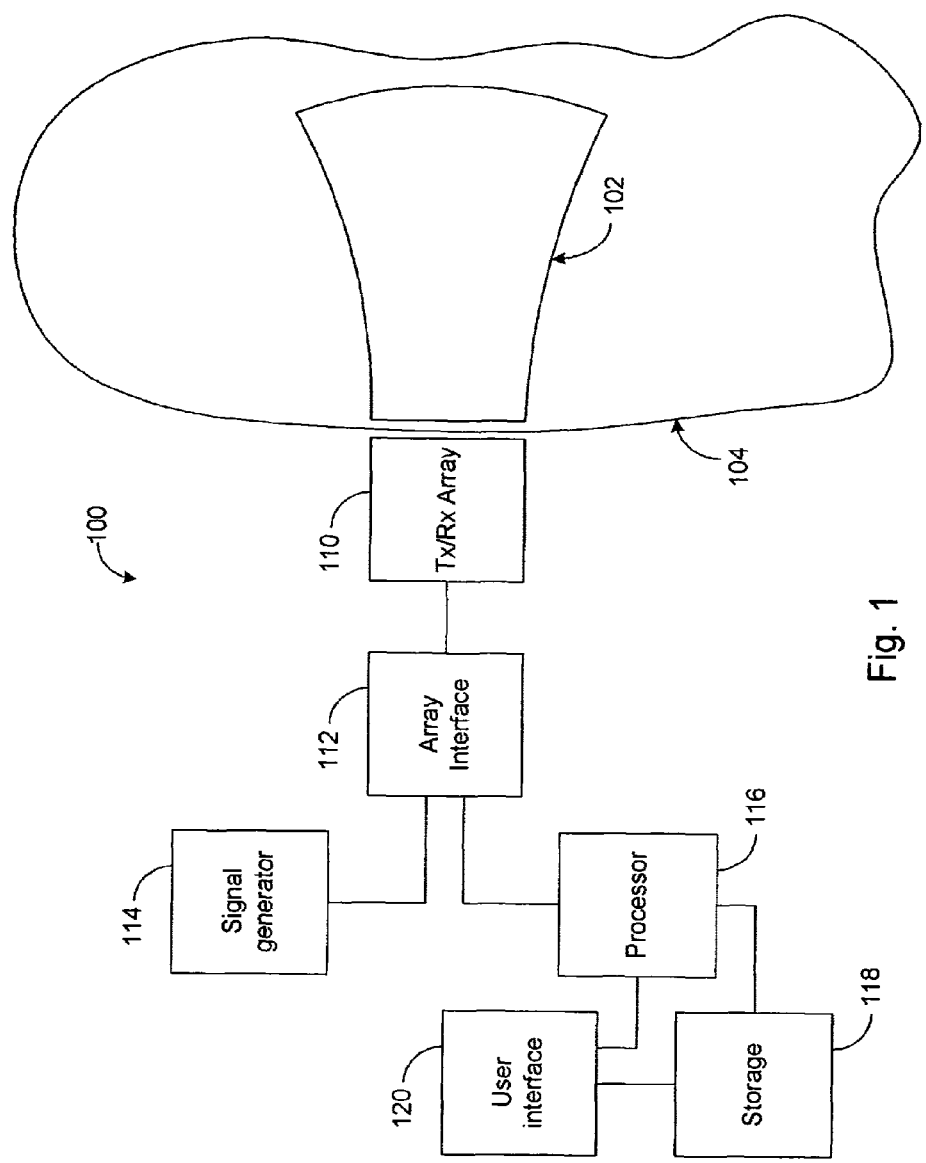
FIG. 1 shows a block diagram of one embodiment of an imaging system that images a defined volume in a medium.

The present teachings generally relate to systems and methods for forming an image of a portion of a medium. FIG. 1 shows a block diagram of one embodiment of an imaging device 100 that includes an array 110 of transducers. A transducer can represent a transmitter or a receiver. As is known, some transducers can operate as transmitters and as receivers. Thus for the purpose of description, a transducer can represent a transmitter, a receiver, or a combination thereof.

As shown in FIG. 1, the imaging device 100 further includes an array interface 112 that facilitates operation of the array 110 of transducers. The array interface 112 may, for example, multiplex and/or demultiplex a plurality of signals to and/or from transmitters and/or receivers. The transducer array 110 via the interface 112 may be supplied with a signal from a signal generator 114. The operation of the interface 112 in providing the signal to the array 110 and/or readout of the received signals from the receivers can be performed by a processor 116. As described below in greater detail, the processor 116 can operate the imaging device 100 in a manner that improves the resolution of the obtained image.

As shown in FIG. 1, the imaging device 100 further includes a storage device 118 that allows retrievable storage of various operating parameters in a manner described below. The imaging device 100 may further includes a user interface 120 that provides an output for a user and/or allow a user to control some of the manner in which the imaging device 100 is operated.

As shown in FIG. 1, the imaging device 100 projects one or more signals into a medium 104 and detects responses of such transmitted signals therefrom. A region 102 that provides measurements in such a manner can be defined as an image volume 102. In the description herein, image volumes are sometimes represented as a two-dimensional plane. In many applications, image "planes" accurately describe the image volume. It will be understood, however, that such representation is in no way intended to limit the scope of the present teachings. It will also be understood that the shape and size of the image volume 102 may vary depending on factors such as the medium, the type of signal being used, and the properties of the imaging device.

It will also be understood that the imaging device, such as the device 100 of FIG. 1, may include both longitudinal-wave and transverse-wave devices. The longitudinal-wave device may include, but is not limited to, ultrasound-based devices, sonar-based devices, or devices that probe underground geological features. The transverse-wave device may include, but is not limited to, devices that operate based on electromagnetic waves such as optical devices or radar-type devices.

Figure 2:
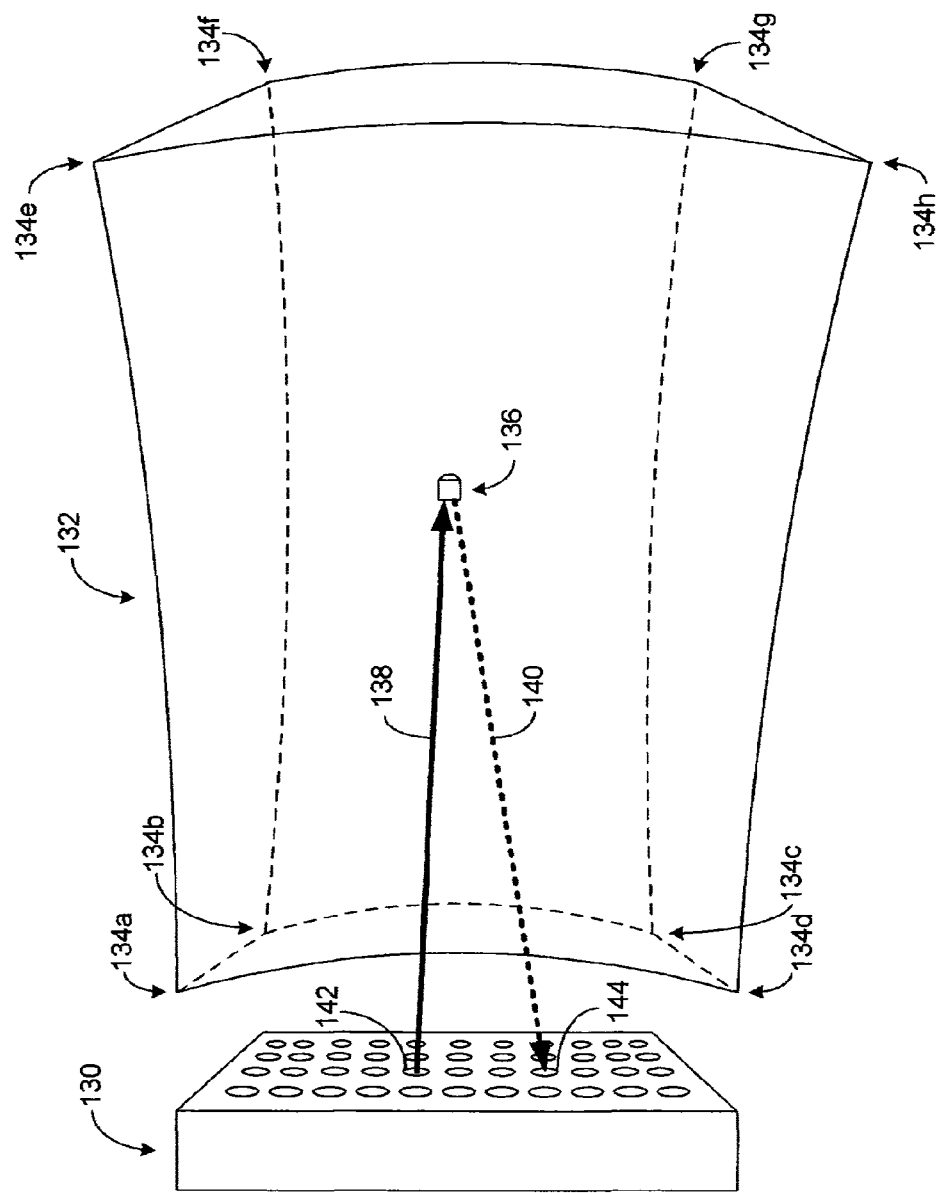
FIG. 2 shows an example transmitter and an example receiver of one embodiment of an array forming an image associated with an example pixel of an image volume.

FIG. 2 now shows one embodiment of an example array 130 of transducers that images a volume 132. The example volume 132 can be defined by a plurality of corner locations 134a-h. Within the volume 132 is shown an example elemental volume 136 (also referred to as a pixel and/or voxel herein). A plurality of such pixels 136 make up the volume 132. It will be understood that the terms pixel (picture element) and voxel (volume element) are used interchangeably throughout the description.

In one embodiment, one or more transducers of the array 130 transmits one or more signals into the volume 132 so as to cover each of the pixels therein. A wave impinging on a pixel can be transmitted through the pixel, reflected from the pixel, or any combination thereof. For example, if an object occupies the pixel, that object can cause a partial reflection and a partial transmission. Measurement of the reflected wave or lack of the reflected wave can yield an image of the pixel.

Thus as shown in FIG. 2, the example pixel 136 is depicted as being probed by a transmitted signal 138 from an example transmitter 142. The pixel's response to that signal 138 as measured by an example receiver 144 is indicated by a dashed arrow 140.

One can see that the resolution of an image of the volume depends on the size of the pixels, and the imaging device's ability to resolve such pixels. As described herein, one aspect of the present teachings relates to systems and methods of probing and measuring the pixels in a manner that improves the resolution of images formed therefrom.

Figure 3:
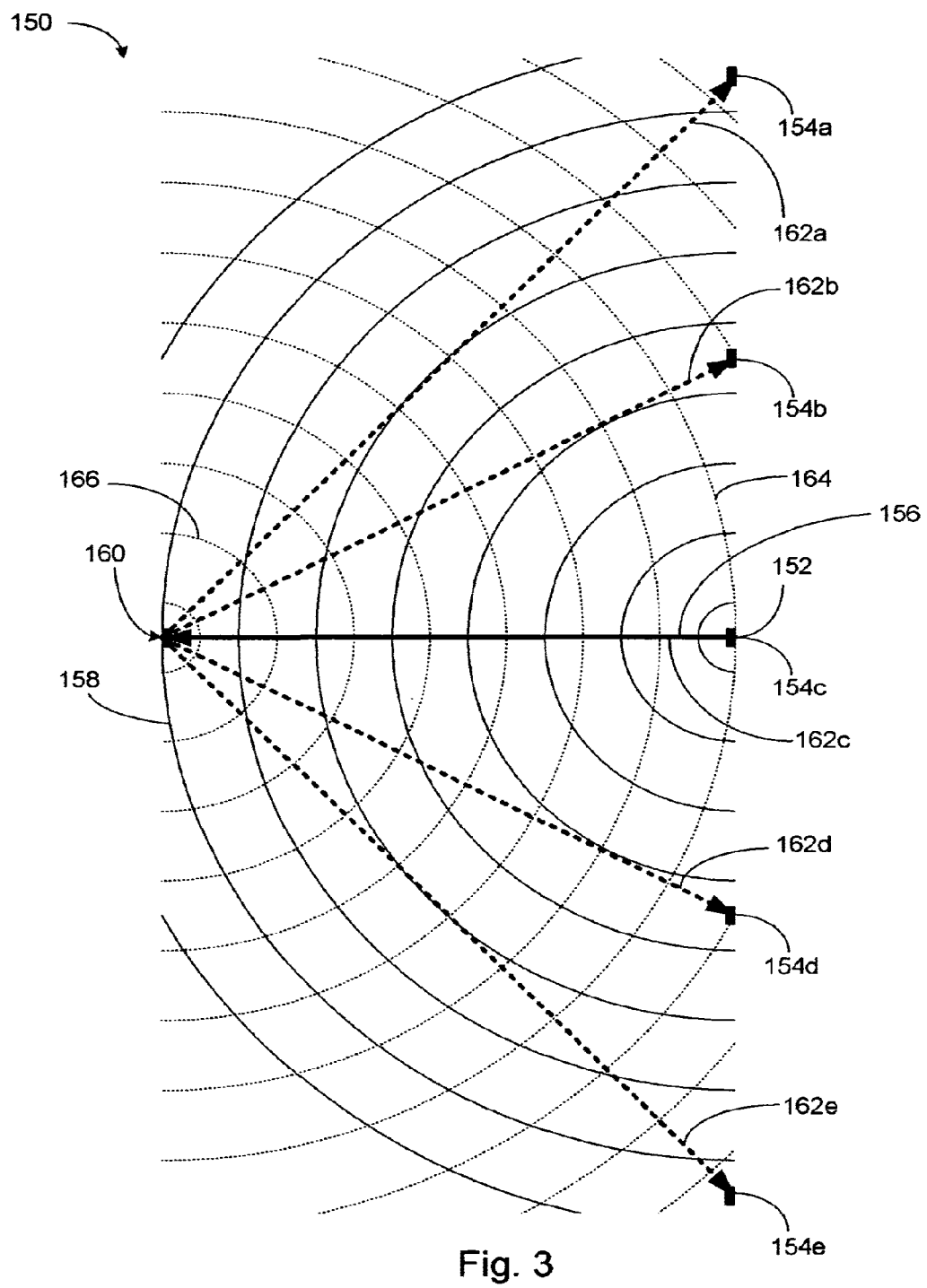
FIG. 3 shows a wave representation of an example array of transducers, where a transmitted signal from one example transducer is shown to reflect from an example target object such that the reflected wave can be detected by a plurality of receivers.

FIG. 3 shows an example wavefront representation 150 of one embodiment of an array of transducers 154a-e probing a target object 160. In the example, the transducers 154 are shown to function as transmitters and receivers, and one receiver 152 is shown to transmit a signal 156. A wavefront 158 impinges on the target 160 and reflects therefrom into a reflected wave 166. A propagated wave 164 is shown to be received first by the transducer 154c. The same wavefront 164 would then be received by other transducers 154a, b, d, e at later times. Rays representing the reflected wave propagation towards the transducers 154a-e are indicated by dashed arrows 162a-e.

By synchronizing and combining the measurements of the reflected wave (example wave 164) by the various transducers, an improved image of the target can be formed. Although FIG. 3 shows a single-transmitter and multiple-receiver operation, it will be understood that any other combinations of transmitters and receivers can be used. As an example, the imaging device can be operated where multiple transmitters transmit multiple signals that are measured by a single receiver. In another example, a plurality of transmitters and a plurality of receivers can be used in various combinations. One aspect of the present teachings relates to performing synchronization and combination of transmitters and/or receivers to improve the performance of the imaging device.

The imaging device can form an image of a portion of a medium containing one or more targets by defining that portion into a plurality of pixels. Thus, in the example target of FIG. 3 can occupy one or more pixels. Probing of those pixels, along with other pixels, can yield an image of the target in its medium.

Figure 4:
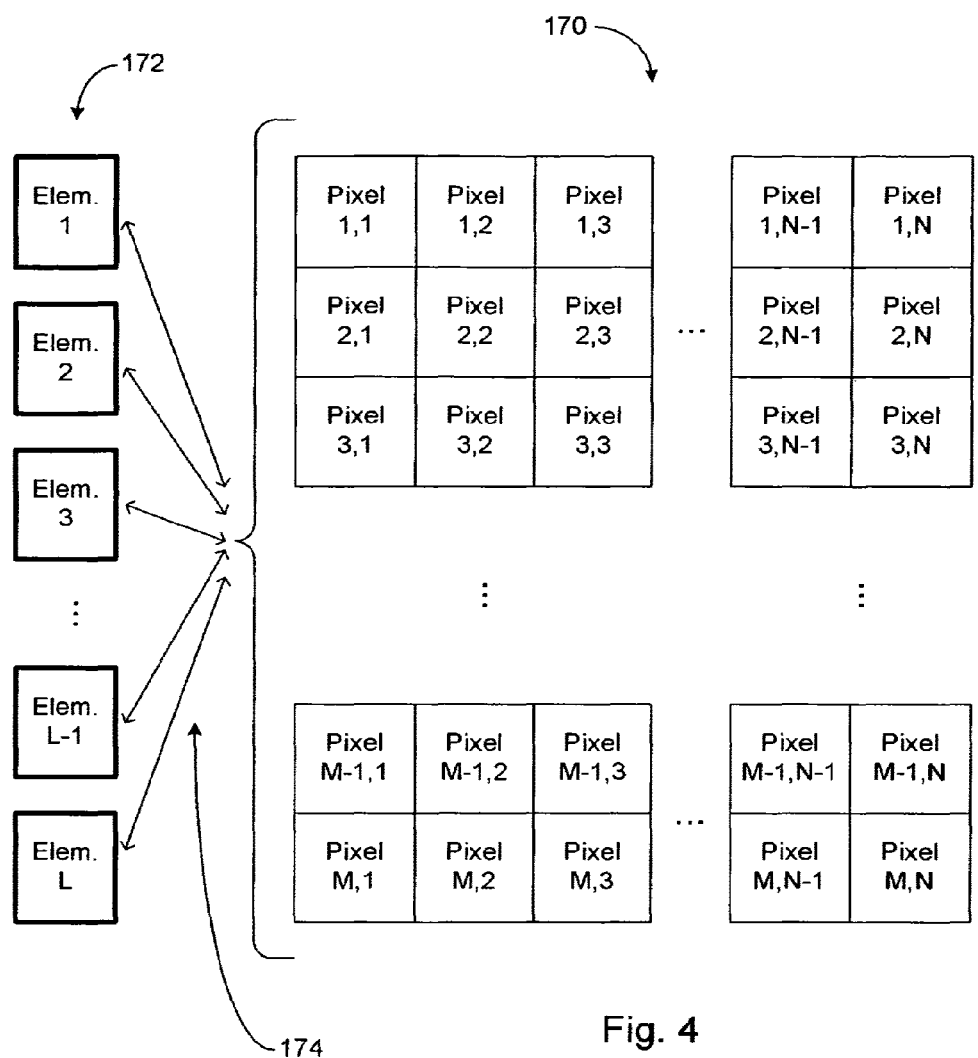
FIG. 4 shows how an image volume can be mapped into a plurality of pixels with respect to a plurality of transducers.

FIG. 4 shows one embodiment of an array of such pixels defined for an image plane 170. The image plane 170 is shown to be divided into an M×N array of pixels. Although FIG. 4 depicts the pixels as squares for the purpose of description, it will be understood that the pixels can be of any definable shape. Furthermore, the overall shape of the image plane 170 need not be rectangular shaped. Moreover, the image plane 170 is referred to as a "plane" for the purpose of description, and is not intended to limit the scope of the present teachings.

Some or all of the pixels of the image plane 170 can be probed by an array 172 of transducer elements. Such probing of the pixels is depicted by a plurality of arrows 174.

FIG. 4 shows L elements arranged along a line to form the array 172. It will be understood that the line arrangement of the transducer elements is for the purpose of description of the image plane 170. The array 172 of transducer elements can be arranged in a two-dimensional array, either in a planar manner or along some curved surface.

Figure 5:
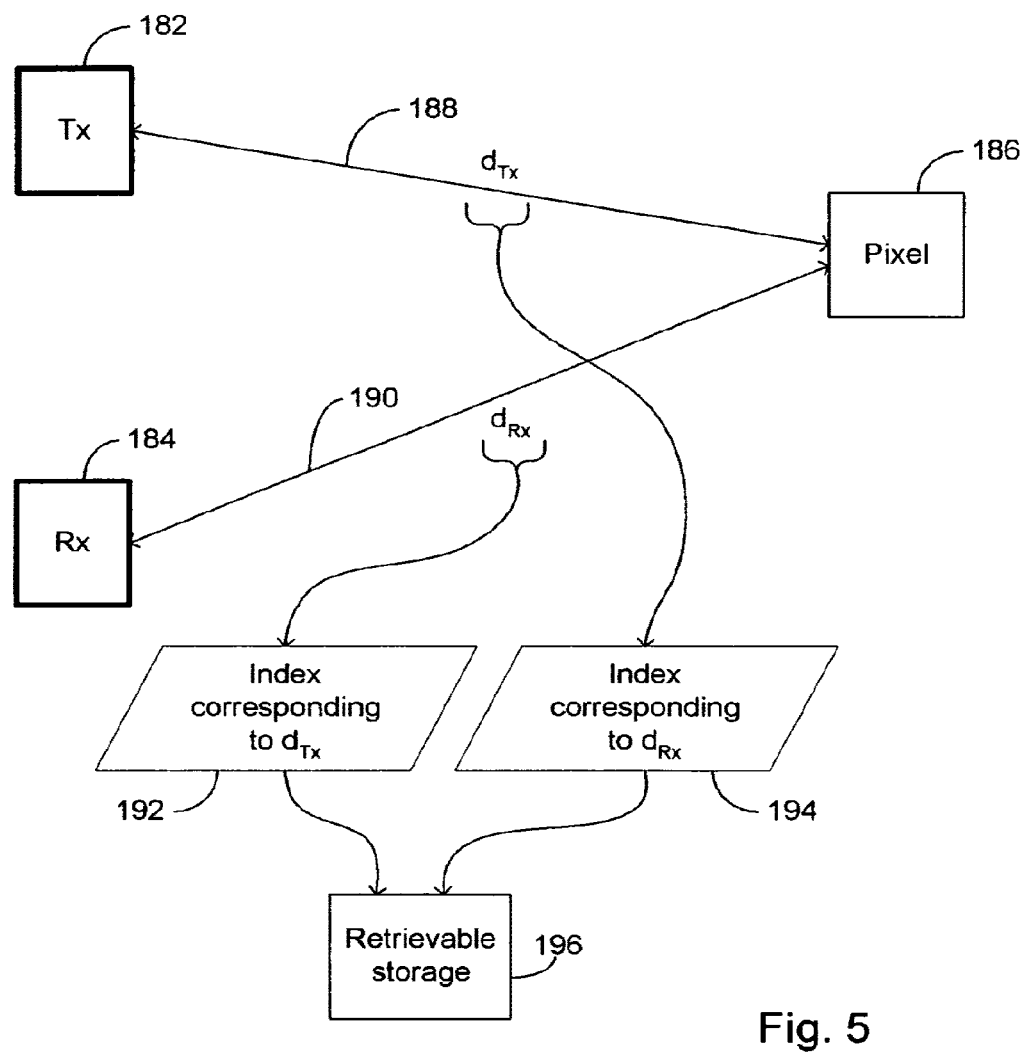
FIG. 5 shows an example of how a position of a pixel relative to a transmitter and a receiver can be stored independently as time-dependent indices based on their respective distances and wave propagation speed.

FIG. 5 now shows how a pixel 186 can be associated with a transmitter 182 and with a receiver 184. By performing such associations for all possible transmitter-pixel and receiver-pixel combinations, a spatial and/or temporal alignment set (also referred to as an "alignment set" herein) of an array of pixel is obtained with respect to an array of transmitters and receivers. One aspect of the present teachings relates to mapping the pixels with respect to the transmitters separately from the receiver-pixel mapping. As described below, such a feature provides significant advantages during certain types of high-resolution imaging operations.

As shown in FIG. 5, the pixel 186 is positioned relative to the transmitter 182 by a distance $d_{Tx}$ (as indicated by arrow 188). Similarly, the pixel 186 is positioned relative to the receiver 184 by a distance $d_{Rx}$ (as indicated by arrow 190). The distance $d_{Tx}$ can be used to determine when a signal from the transmitter 182 can be expected to reach the pixel 186. Similarly, the distance $d_{Rx}$ can be used to determine when a possibly-reflected signal from the pixel 186 can be expected to reach the receiver 184. Such expectation information can be used to effectively combine signals associated with different transmitter-pixel and/or receiver-pixel combinations.

The expectation arrival information for the transmitter-pixel combination depends on the distance $d_{Tx}$, and can be represented as some form of an index. Such an index can also account for factors other than the distance that affect the arrival of the signal. As an example, electronic circuitry associated with the transmitter may cause the signal to be transmitted after a delay from some start time. Thus, an index data 194 corresponding to the distance $d_{Tx}$ may also include such other factors.

Similarly, the expectation arrival information for the receiver-pixel combination depends on the distance $d_{Rx}$, and can be represented as some form of an index. Such an index can also account for factors other than the distance that affect the arrival of the signal. As an example, a readout process associated with the receiver may cause the signal to be sampled after a delay from the time when the signal impinges on the receiver. Thus, an index data 192 corresponding to the distance $d_1$ may also include such other factors.

As shown in FIG. 5, the indices 194 and 192 can be stored independently in a retrievable storage 196. A collection of such indices for all possible transmitter-pixel and receiver-pixel combinations then defines the alignment set of the array of pixels.

Figure 6:
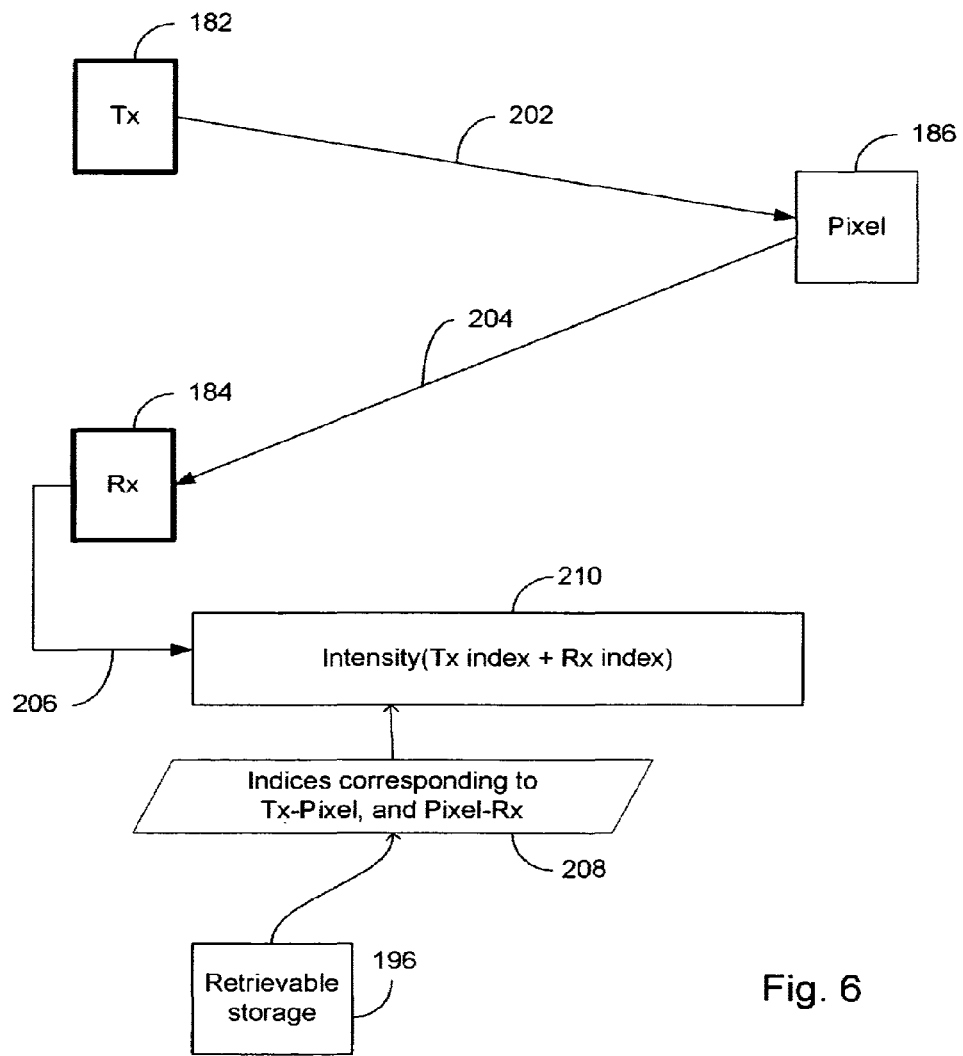
FIG. 6 shows how the indices can be used to selectively sample a signal received by a receiver.

FIG. 6 now shows how an alignment set for the pixel 186 can be used to obtain a selectively sampled signal 210 from an output 206 of the receiver 184. A transmitted signal from the transmitter 182 propagating towards the pixel 186 is depicted as an arrow 202. The signal 202 may or may not experience reflection from the pixel 186. Thus, an arrow 204 represents how a reflected signal would propagate from the pixel 186 to the receiver 184.

As further shown in FIG. 6, data 208 having the transmitter-pixel and receiver-pixel indices can be retrieved from the storage 196, and be used selectively sample the output 206 of the receiver 184. In one embodiment, such selectively sampled signal 210 is obtained by sampling the output 206 at an index corresponding to the sum of the transmitter-pixel and receiver-pixel indices. Some possible forms of the indices are described below in greater detail.

FIGS. 7 and 8 now show processes that perform the index determination and subsequent use, respectively, for an array of transducers. A process 220 determines the indices for a given pixel array with respect to a given array of transducers. The process 220 begins at a start state 222, and in a process block 224, the process 220 obtains detector and map parameters. Detector parameters may include the number of transmitters and the number of receivers. Map parameters may include the number of pixels, the desired size of the pixels, and the arrangement of the pixels.

The process 220 in a process block 226 defines the array of transmitters and receivers. In one embodiment, each transmitter and each receiver are defined in terms of their positions relative to a chosen coordinate system. In an embodiment where transmitter and receiver function are performed by a common transducer, the array definition only needs to be performed for the transducer array. An example array definition is described below in greater detail.

The process 220 in a process block 228 defines the array of pixels as determined by the map parameters. In one embodiment, each pixel is defined in terms of its position relative to the transmitter/receiver array. An example array definition is described below in greater detail.

The process 220 in a process block 230 determines a propagation index corresponding to each transmitter-pixel combination. An example propagation index determination is described below in greater detail.

The process 220 in a process block 232 determines a sampling index corresponding to each receiver-pixel combination. An example sampling index determination is described below in greater detail.

The process 220 in a process block 234 stores the propagation indices and the sampling indices. An example storage of the indices is described below in greater detail. The process 220 ends at a stop state 236. In one embodiment, the alignment set generation process 220 is performed once for a given transducer array and a given pixel array, and does not need to be re-done during the imaging operation.

As shown in FIG. 8, an image generation process 240 determines the measured signals associated with some or all of the pixels using the previously determined alignment set for the transducer-pixel configuration. The process 240 begins at a start state 242, and in a process block 244, the process 240 obtains imaging parameters. In one embodiment, the imaging parameters include the number of transmitters and receivers, and alignment sets for transmitter-pixel and receiver-pixel combinations.

The process 240 in a process block 246 sets initial values for each of the pixels being evaluated. An example of such initialization is described below in greater detail The process 240 in a process block 248 transmits signal(s) into the pixel array, and samples signal(s) at indices corresponding to selected transmitter-pixel-receiver combinations. An example of selected transmitting and sampling is described below in greater detail.

The process 240 in a process block 250 determines the intensity of each of the selected pixels from the sampled signal(s). An example of such intensity determination is described below in greater detail.

The process 240 in a process block 252 processes the pixel intensities to form an image associated with the pixel array. The process 240 ends at a stop state 254.

Figure 9:
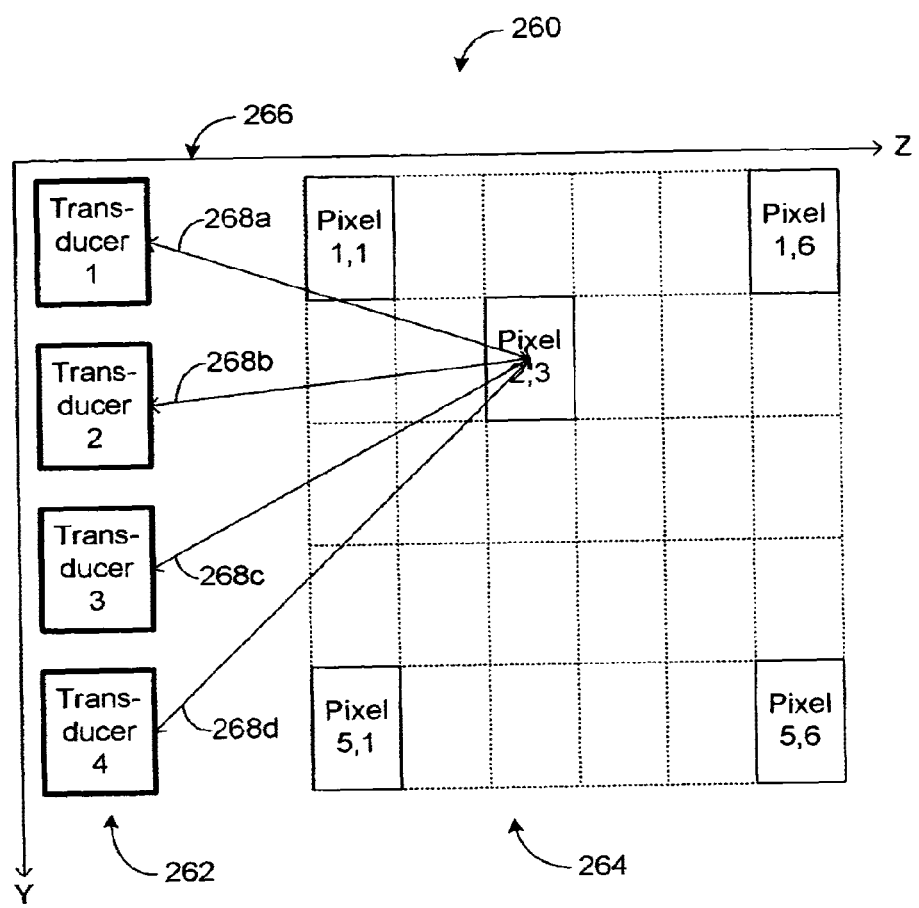
FIG. 9 shows an example of how a pixel array can be defined with respect to a transducer array, thereby allowing determination of distances between transducers and pixels.
Figure 10:
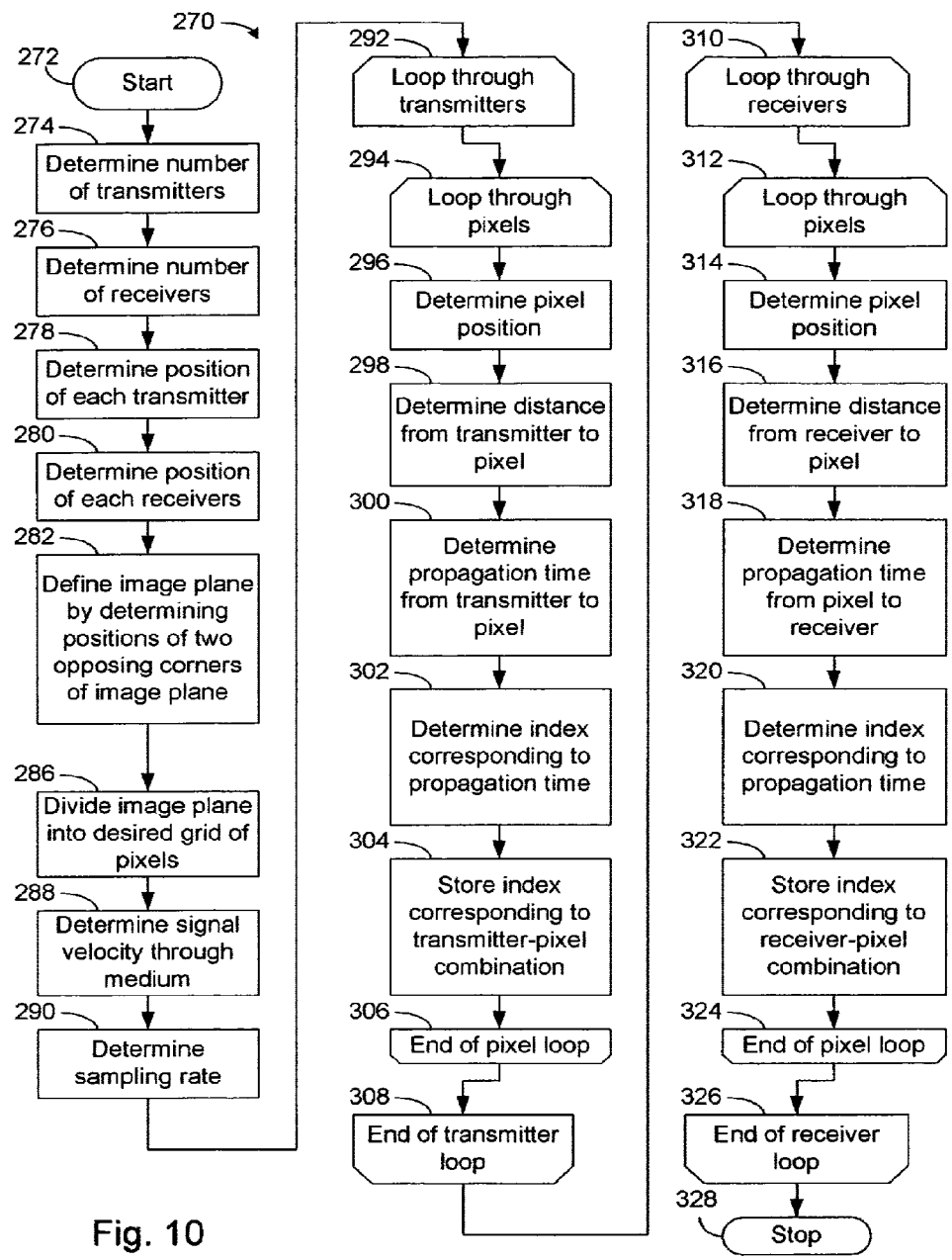
FIG. 10 shows a process that separately determines indices corresponding to various position-defined transmitter-pixel and receiver-pixel combinations.
Figure 11:
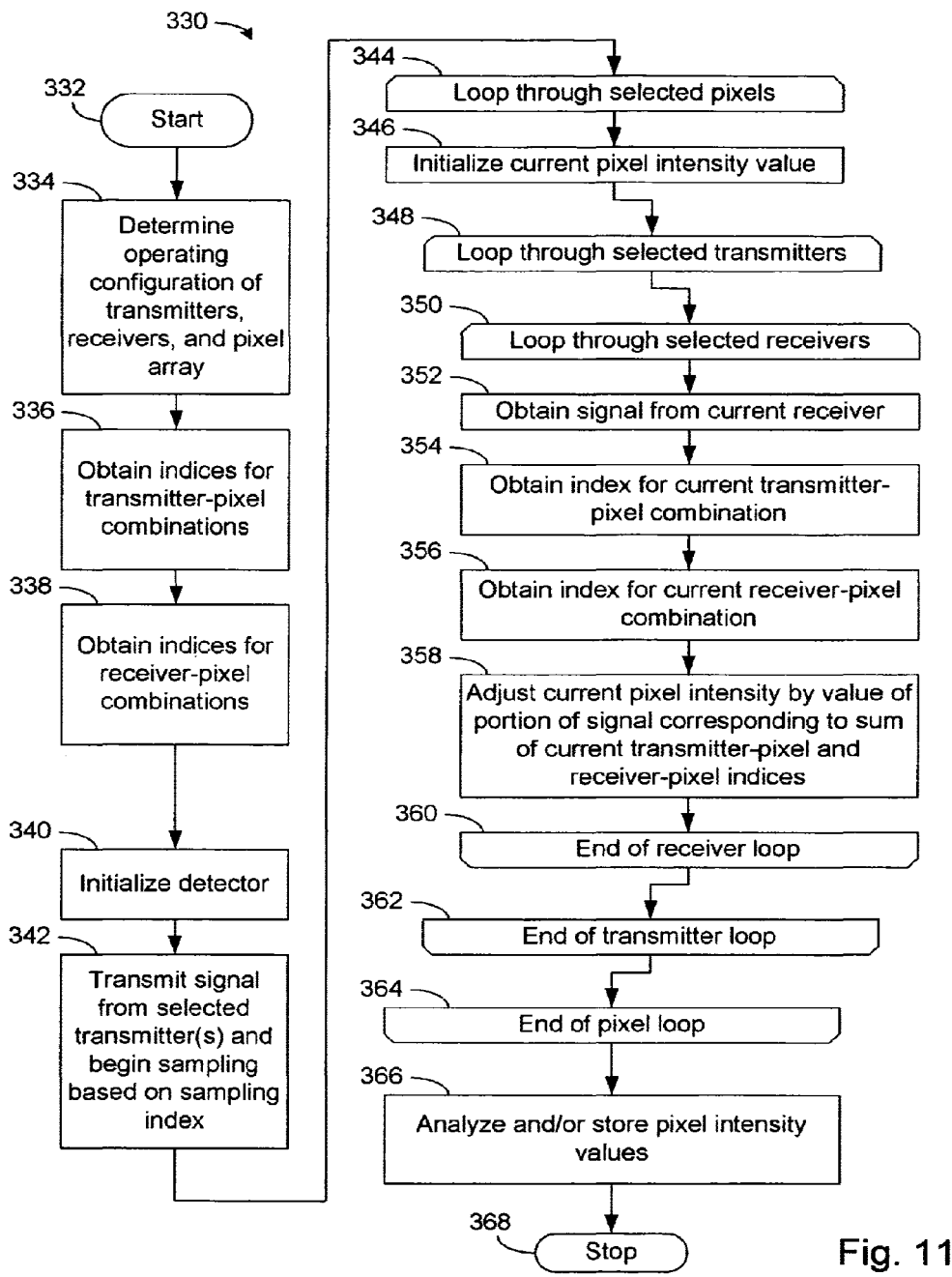
FIG. 11 shows a process that uses the transmitter-pixel and receiver-pixel indices to image selected pixels using selected transmitters and selected receivers.

FIGS. 9-11 now show more specific manner in which the transducer and pixel arrays can be configured, and how mapping and imaging operations can be performed on such a configuration. FIG. 9 shows an example configuration 260 of array of pixels 264 relative to an array of transducers 262. It will be understood that use of four example transducers 262 is for descriptive purpose only, and in no way intended to limit the scope of the present teachings. Similarly, the use of 5×6 array of pixels 264 is for descriptive purpose only, and in no way intended to limit the scope of the present teachings.

In one embodiment, the positions of the transducers 262 are defined with respect to a coordinate system 266. Although a Cartesian coordinate system is used, it will be understood that any coordinate system can be used for such definition.

In one embodiment, the array of pixels 264 are formed by dividing up an image plane into a grid (5×6 in the example) of pixel regions. One way to define such a grid is to define the positions of set of opposing corner pixels—for example, (1,1) and (5,6), or (1,6) and (5,1), with respect to the coordinate system 266. Then, one can specify number of rows (5 in this example) and columns (6 in this example). Such a definition of the grid provides sufficient information to define the size and position of each of the pixels. One can see that the pixel grid can be defined in any number of ways. Thus, the example method disclosed herein is not intended to limit the scope of the present teachings.

Once the pixel grid 264 is established with respect to the chosen coordinate system 266, each pixel's position can be referenced to each transducer. As an example, the pixel (2,3) is shown to be referenced to transducers 1 to 4 as denoted by arrows 268a-d. Such relative positions of the pixel to the transducers can be used to obtain the transmission indices and sampling indices.

One way of obtaining an index associated with a given transducer-pixel combination is to first determine the distance between the transducer and the pixel. Such determination can be achieved by simple geometry calculation based on the chosen coordinate system. As an example, if the coordinates of the pixel and the transducer can be represented by $(x_p, y_p, z_p)$ and $(x_t, y_t, z_t)$ respectively, the distance d between the two points can be calculated as square root of the quantity $(x_t-x_p)^2+(y_t-y_p)^2+(z_t-z_p)^2$.

The distance d obtained in the foregoing manner can then be used to determine the propagation time t between the transducer and the pixel as $t=d/v$ where v is the magnitude of the propagation velocity of the signal of interest in the medium. For sampling purposes, the propagation time t can further be expressed as a sample number $i_{sample}$ for situations where the received signal is sampled at a sampling rate. In one embodiment, the sample number can be represented as $i_{sample}=(t)(\text{sample rate})$. As previously described, the actual time between some "start" time and sampling time may include time(s) in addition to the propagation times. Such additional time, if any, can also be represented as a sample-rate-based quantity, and added to that associated with the propagation times.

From the foregoing description of the sample number determination, one can see that similar information can be obtained in any number of ways. Thus, it will be understood that any number of other methods, or variations of the disclosed method, can be used to obtain and store the indices associated with the transmitter-pixel and receiver-pixel combinations.

FIG. 10 now shows one implementation of a detailed process 270 for determining an alignment set for a given pixel array with respect to a given transmitter and receiver arrays. The process 270 begins at a start state 272, and in a process block 274, the number of transmitters is determined. In a process block 276, the number of receivers is determined. In a process block 278, the position of each transmitter is determined. In a process block 280, the position of each receiver is determined.

In a process block 282, the process 270 defines an image plane by determining positions of two opposing corners of the image plane. In a process block 286, the image plane is divided into a grid defined by desired numbers of rows and columns of pixels.

In a process block 288, the process 270 determines the signal's velocity through the medium being imaged. In a process block 290, the sampling rate is determined.

As shown by a loop 292 (with end-loop 308), the process 270 loops through the transmitters. For each transmitter, the process 270 loops through the pixels (loop 294, with end-loop 306). Thus for each combination of the transmitter and pixel, the process 270 determines the pixel position in a process block 296. In a process block 298, the distance between the transmitter and the pixel is determined. In a process block 300, propagation time between the transmitter and the pixel is determined based on the distance and signal velocity (t=d/v). In a process block 302, an index corresponding to the propagation time is determined. In one embodiment, the index can be represented as a product of the propagation time and the sampling rate of the imaging device. In a process block 304, the index corresponding to the transmitter-pixel combination is saved for later retrieval and use. The loops 294 and 292 end at loop-ends 306 and 308 respectively.

As shown by a loop 310 (with end-loop 326), the process 270 loops through the receivers. For each receiver, the process 270 loops through the pixels (loop 312, with end-loop 324). Thus for each combination of the receiver and pixel, the process 270 determines the pixel position in a process block 314. In a process block 316, the distance between the receiver and the pixel is determined. In a process block 318, propagation time between the pixel and the receiver is determined based on the distance and signal velocity (t=d/v). In a process block 320, an index corresponding to the propagation time is determined. In one embodiment, the index can be represented as a product of the propagation time and the sampling rate of the imaging device. In a process block 322, the index corresponding to the receiver-pixel combination is saved for later retrieval and use. The loops 312 and 310 end at loop ends 324 and 326 respectively. The process 270 ends at a stop state 328.

As previously described, the alignment set generation, such as that of the process 270, is generally performed once and does not need to be repeated during subsequent imaging operations. The stored indices corresponding to the transmitter-pixel and receiver-pixel combinations allow such subsequent improved-resolution imaging operations to be performed in an efficient manner.

FIG. 11 now shows one implementation of a detailed process 330 for performing an imaging operation utilizing the alignment set obtained previously. The process 330 begins at a start state 332, and in a process block 334 an operating configuration of transmitters, receivers, and pixels is determined. In one embodiment, such an operating configuration defines the numbers and positions of the transmitters, receivers, and pixels in a manner similar to that used for the alignment set determination process. As such, one or more operating configurations can be stored, and one configuration can be either selected by a user or be used as a default.

In a process block 336, the process 330 obtains a set of indices corresponding to the transmitter-pixel combinations of the operating configuration. In a process block 338, a set of indices corresponding to the receiver-pixel combinations of the operating configuration is obtained.

In a process block 340, the process 330 initializes the imaging detector. In one embodiment, such initialization includes initializing the values of the pixel intensities.

In a process block 342, the process 330 transmits a signal from selected transmitter(s) and begins sampling for return signals from the pixel array using selected receiver(s). In one embodiment, a sampling "start" is issued at some predetermined time about the time when the signal leaves the transmitter. Referencing the samplings from such a common start time allows correlated sampling of all the transmitter-pixel-receiver combinations. By having separate sets of transmitter-pixel and receiver-pixel indices, such correlated sampling, as well as other variations of operation of the imager, can be performed more efficiently.

In one embodiment, the process 330 measures the pixel array by sampling signals associated with each of the transmitter-pixel-receiver combinations. One way to cover all the combinations is to perform nested loops for the transmitters, pixels, and receivers. Thus, the process 330 is shown to loop through the selected pixels (loop 344, end-loop 364). For each pixel in the pixel loop 344, its intensity value is initialized in a process block 346. For each initialized pixel, the process 330 loops through the selected transmitters (loop 348, end-loop 362). For each pixel-transmitter combination, the process 330 loops through the selected receivers (loop 350, end-loop 360). Thus for each pixel-transmitter-receiver combination of the nested loops 344, 348, 350, the process 330 in a process block 352 obtains a signal from the current receiver. In a process block 354, the index for the current transmitter-pixel combination is obtained. In a process block 356, the index for the current receiver-pixel combination is obtained. In a process block 358, the pixel intensity is adjusted by a value of the receiver signal corresponding to the sum of current transmitter-pixel and receiver-pixel indices.

As shown in FIG. 11, pixel intensity values obtained in the foregoing manner can be further analyzed or stored (for later analysis) in a process block 366. The process 330 ends in a stop state 368.

Figure 12:
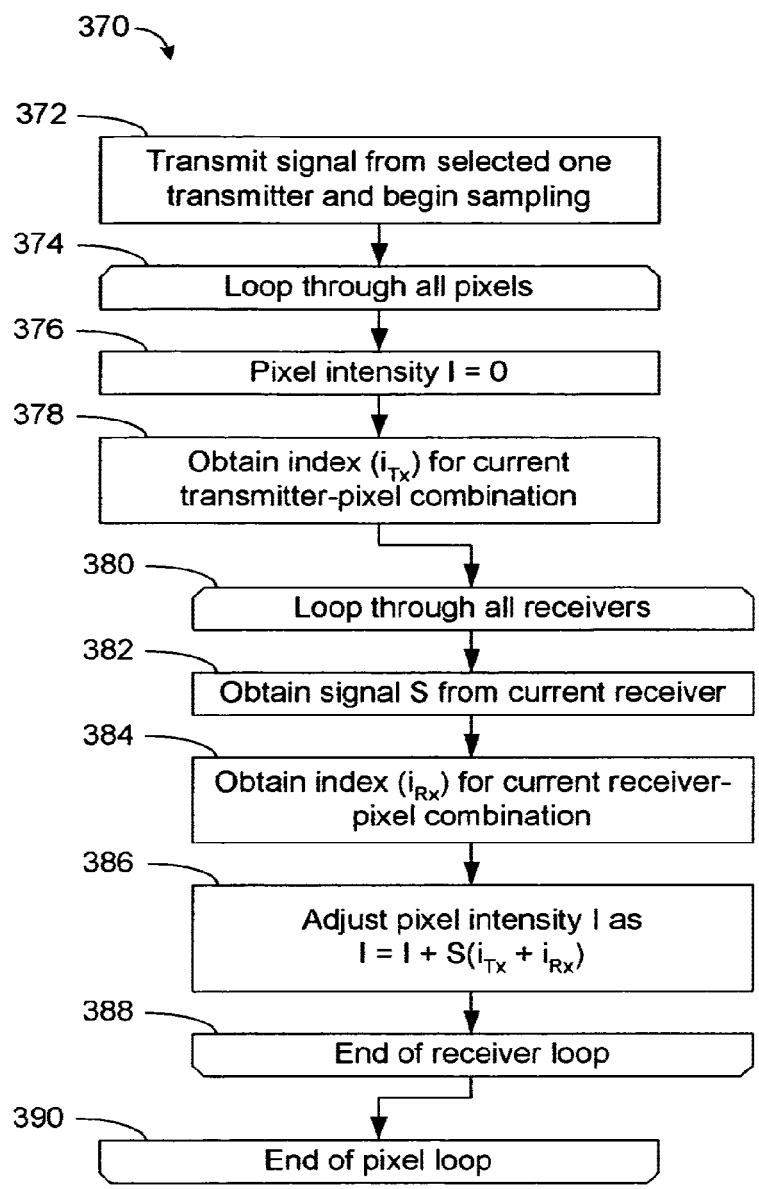
FIG. 12 shows an example process that images a pixel array by transmitting from one selected transmitter and sampling from substantially all receivers.
Figure 13:
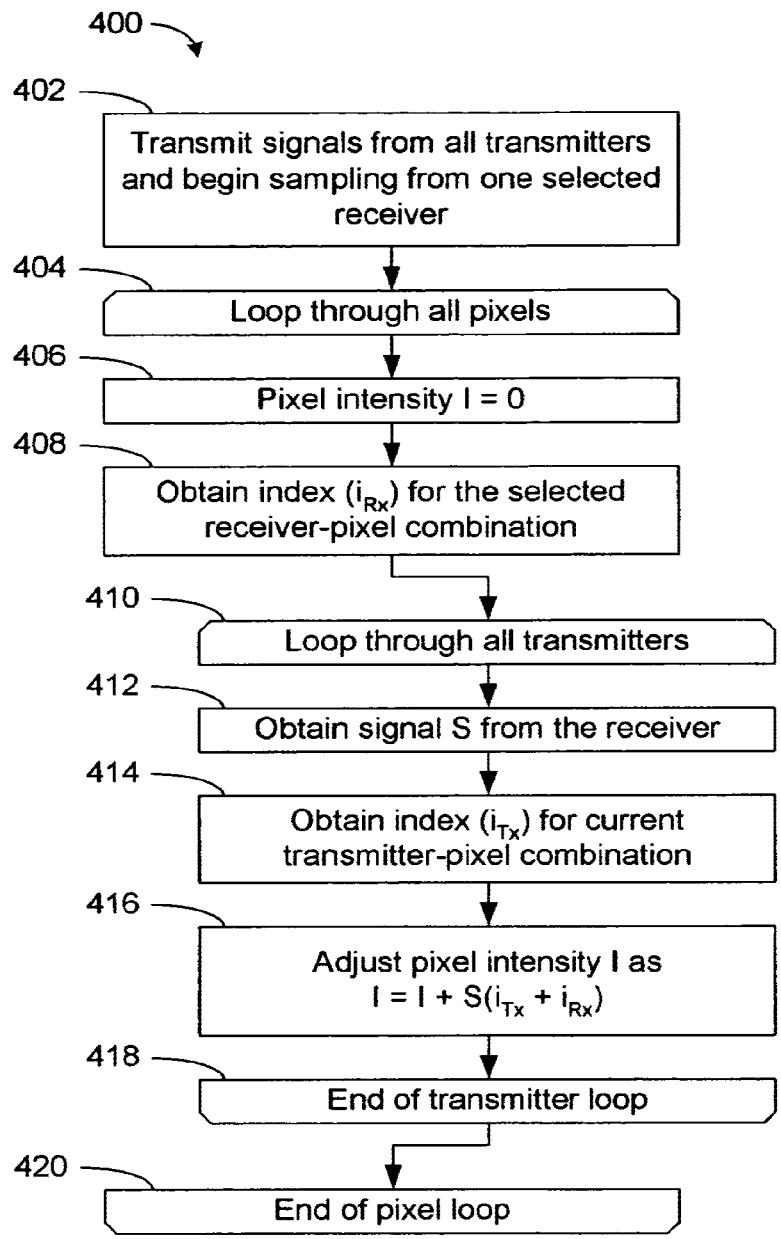
FIG. 13 shows an example process that images a pixel array by transmitting from substantially all transmitters and sampling from one receiver.

FIGS. 12 and 13 now show two specific examples of using selected transmitter(s) and selected receiver(s) to obtain an improved image quality. In FIG. 12 an example process 370 is shown where a single selected transmitter and a plurality of selected receivers are used. In FIG. 13, an example process 400 is shown where a plurality of selected transmitters and a single selected receiver are used.

As shown in FIG. 12, the example process 370 in a process block 372 transmits a signal from a selected transmitter and begins sampling. Such a beginning of sampling can be at a predetermined time relative to the time when the transmitted signal begins propagating from the transmitter. The process 370 then loops through all of the pixels in a loop 374 (with an end-loop 390). For each pixel, the process 370 sets that pixel's initial value to zero in a process block 376. Also for that pixel, the process 370 obtains the index $i_{Tx}$ for the current transmitter-pixel combination in a process block 378.

For the current pixel, the process 370 then loops over all of the selected receivers in a loop 380 (with an end-loop 388). The process 370 in a process block 382 obtains a signal S from the current receiver. In a process block 384, the index for the current pixel-receiver combination $i_{Rx}$ is obtained. In a process block 386, the current pixel's intensity value is adjusted as $I=I+S(i_{Tx}+i_{Rx})$.

As shown in FIG. 13, the example process 400 in a process block 402 transmits signals from all of the selected transmitters, and begins sampling from one selected receiver. Transmitting of the signals from the selected transmitters can be either simultaneous or in a predetermined sequence. In embodiments where the number of selected transmitters is relatively small, the signals may be transmitted substantially simultaneously, and the sampling may be able to temporally distinguish the transmitter-pixel-receiver combinations. In embodiments where the number of selected transmitters is relatively large, the signals being transmitted simultaneously may not allow effective selective sampling of the transmitter-pixel-receiver combinations.

In embodiments where the signals are transmitted simultaneously, beginning of sampling can be at a predetermined time relative to the time when the transmitted signals begin propagating from the transmitters. In embodiments where the signals are transmitted in some sequence, beginning of sampling can be defined in a variety of ways. One way is to have a common start time, and account for the different transmit times for different transmitters as adjustments to the transmitter-pixel combination indices.

The process 400 then loops through all of the pixels in a loop 404 (with an end-loop 420). For each pixel, the process 400 sets that pixel's initial value to zero in a process block 406. Also for that pixel, the process 400 obtains the index $i_{Rx}$ for the current receiver-pixel combination in a process block 408.

For the current pixel, the process 400 then loops over all of the selected transmitters in a loop 410 (with an end-loop 418). The process 400 in a process block 412 obtains a signal S from the receiver. In a process block 414, the index for the current transmitter-receiver combination $i_{Tx}$ is obtained. In a process block 416, the current pixel's intensity value is adjusted as $I=I+S(i_{Tx}+i_{Rx})$.

Figure 14:
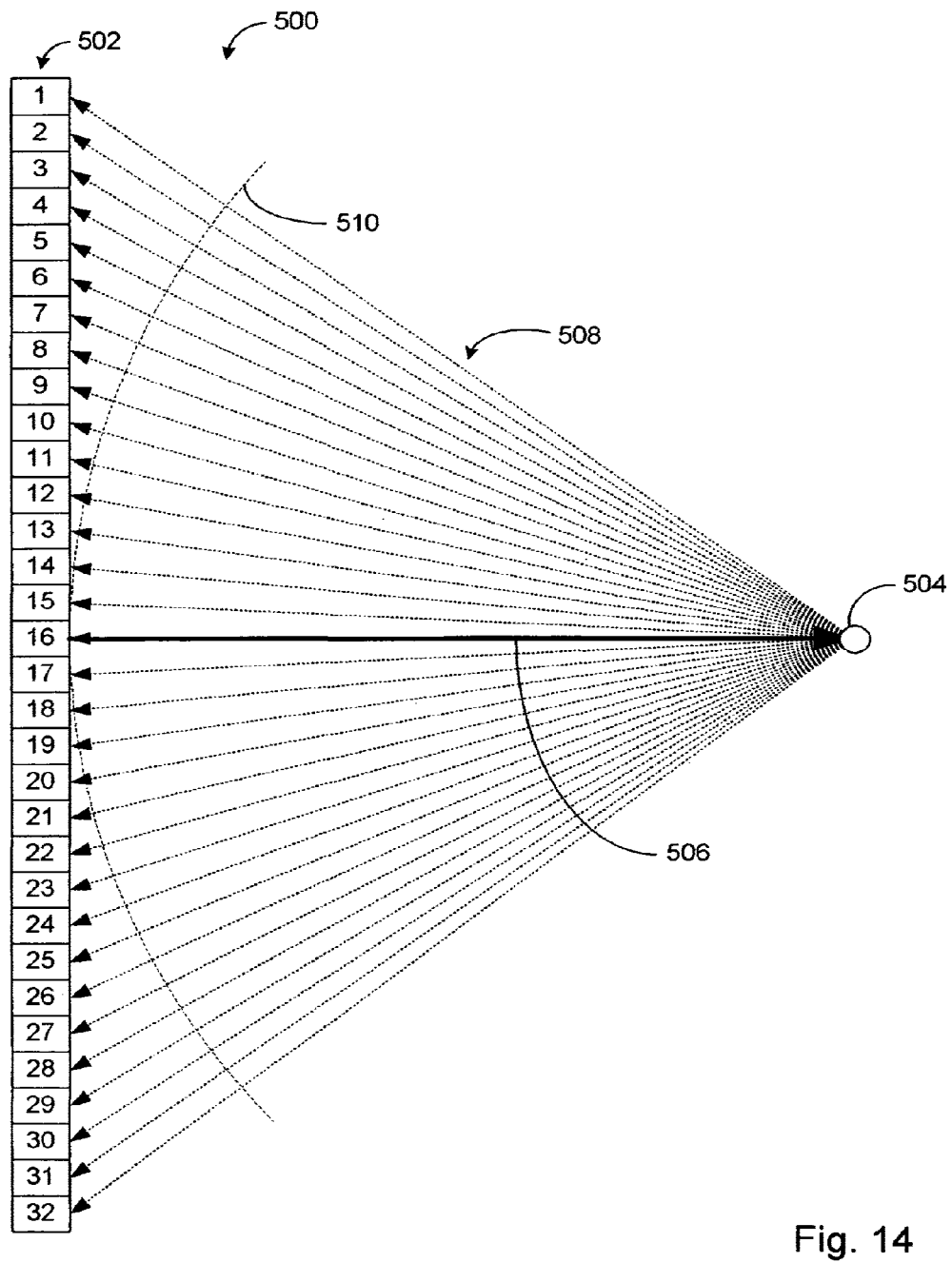
FIG. 14 shows a ray representation of an example 32-transducer device being operated in a single-transmitter/all-receiver mode.

In one embodiment as shown in FIG. 14, an imaging device includes 32 elements. In particular, FIG. 14 shows a ray representation 500 of the embodiment where one transmitter (transmitter 16) transmits a signal 506 to an object 504, resulting in a reflected wave 510 that is detected by 32 receivers (1 to 32). The reflected wave 510 propagating to the receivers 502 is represented by reflected rays 508, and the intersection of the wavefront 510 with the rays 508 represent the in-phase portions of the rays 508.

For the example embodiment 500, the index $I_D$, representative of the transmitted signal 506 is common to all of the sampling indices used by the 32 receivers. For the particular example where the object is located at the mid-level of the array 502, the reflected wave 510 reaches receiver 16 first. Thus, the sampling index associated with the pixel where the object 504 is located would have a value that causes the signal from receiver 16 to be sampled first. Thereafter, signals from receivers 15 and 17 would be sampled, followed by 14 and 18, etc. Signal from receiver 32 would be the last to be sampled at a time corresponding to the extra propagation distance of the wavefront 510.

Figure 15:
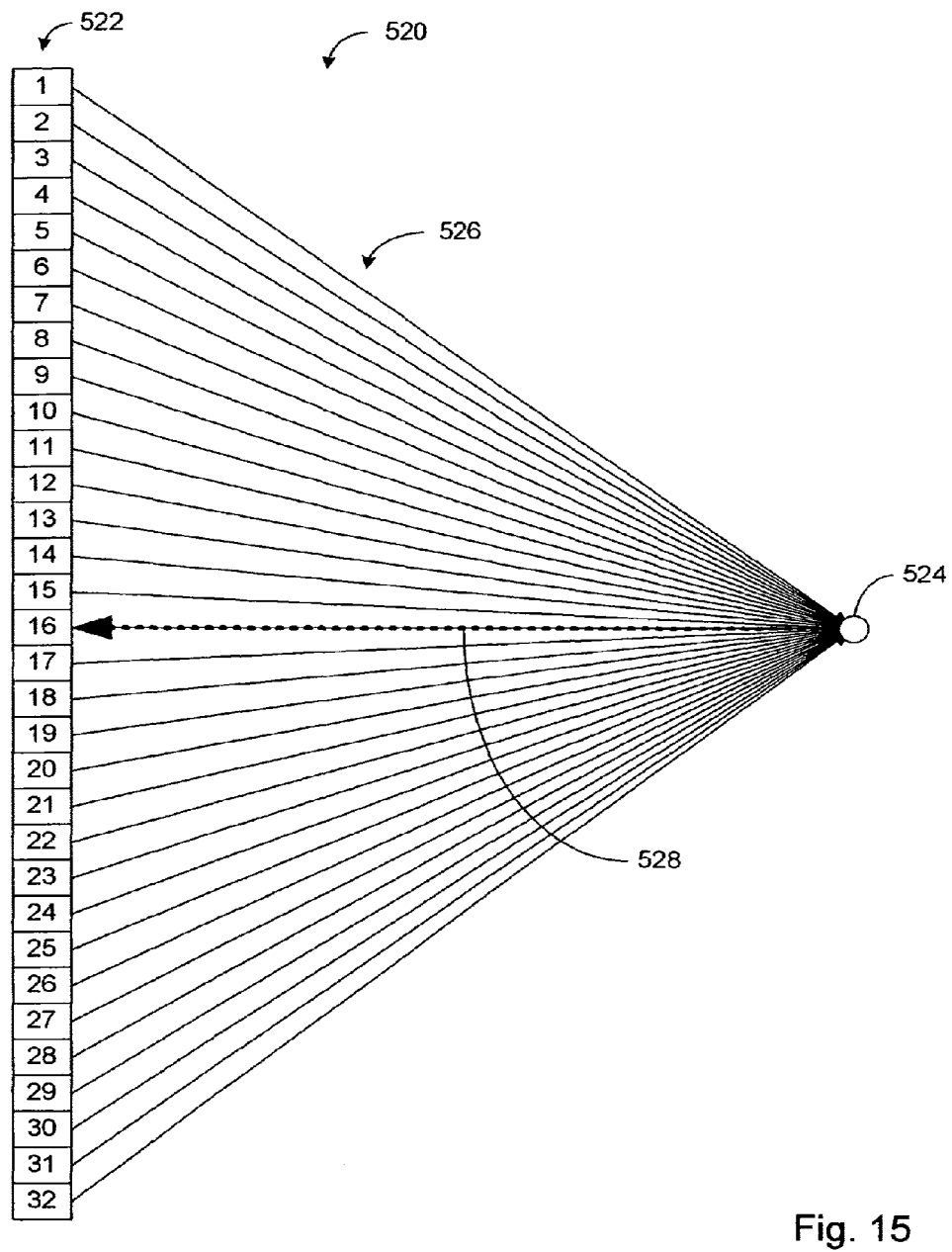
FIG. 15 shows a ray representation of the 32-transducer device being operated in an all-transmitter/single-receiver mode.

In one embodiment as shown in FIG. 15, an imaging device includes 32 elements. In particular, FIG. 15 shows a ray representation 520 of the embodiment where all 32 transmitters transmit signals 526 to an object 524, resulting in a reflected signal 528 that is detected by receiver 16. For the example embodiment 520, the index $i_{Rx}$ representative of the reflected signal 528 is common to all of the sampling indices associated with the 32 receivers.

For the particular example where the object is located at the mid-level of the array 502, the transmitted signal from transmitter 16 reaches the object 524 first (assuming that all signals are transmitted simultaneously). Thus, the sampling index associated with the pixel where the object 524 is located would have a value that causes the first sampled signal to be associated with transmitter 16. The next set of sampled signals would be associated with transmitters 15 and 17, and so on. The last set of sampled signals would be associated with transmitter 32.

As previously described in reference to FIG. 13, the plurality of signals can be transmitted from the transmitters in different ways. Sequenced transmission of signals from the plurality of transmitters can temporally separate the arrivals of the signals at the object 524, as well as reflected signals at the receiver thereafter. One way to sequence the signal transmission is to begin transmission at the transmitter 16, followed at a predetermined time by transmission at transmitters 15 and 17, etc. Such a sequence of transmission can increase the temporal separation of the samplings associated with the array of receivers 522.

Figure 16:
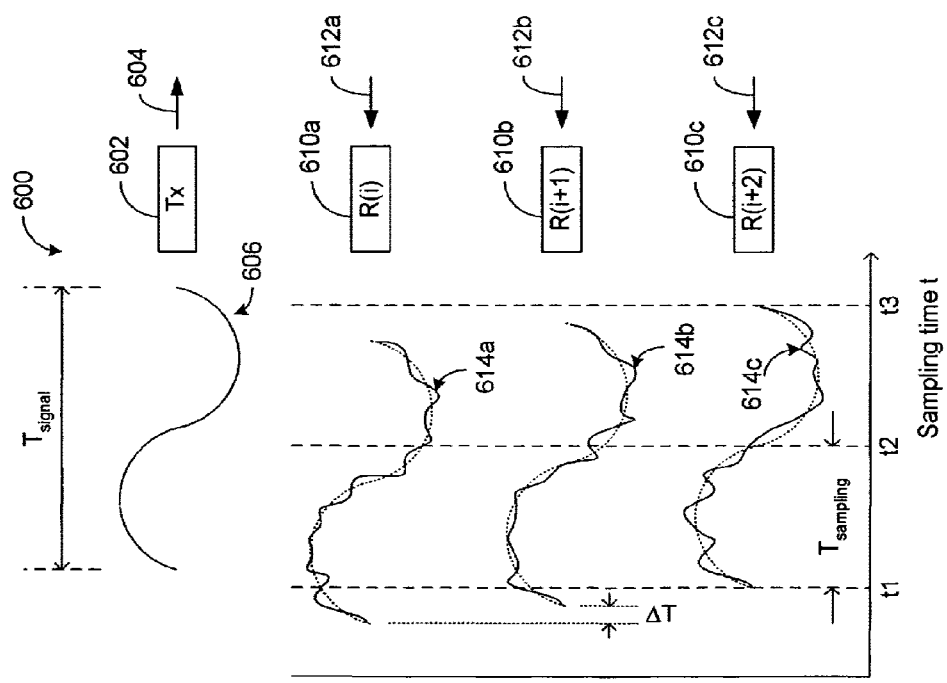
FIG. 16 shows how use of multiple receivers can allow sampling of fine perturbation features that are significantly smaller than that of a carrier signal.

FIG. 16 now shows how sampling by a plurality of transducers can yield an effective sampling rate that is greater than a sampling rate associated with each of the transducers. In an example operating configuration 600, a transmitter 602 is depicted as transmitting a transmission energy 604 into a medium (not shown) in response to a transmission signal 606. The transmission signal 606 is depicted as a periodic signal; but such a characteristic is not a requirement. The transmission signal 606 can be of any waveform having some time-characterizable feature. For example, if the transmission signal 606 is a single pulse, it may be characterized by it temporal width.

The example operating configuration 600 further includes a plurality of receivers 610 that receive respective reflection energies 612. In response to the reflection energies 612, the receivers 610 output respective signals 614 that are sampled. In this example, the plurality of receivers 610 are shown to be sampled simultaneously for the purpose of description. It will be understood that simultaneous sampling of the receiver signals is not a requirement.

Also for the purpose of description, the common sampling is shown to have a period $T_{sampling}$ that is approximately half of the transmission signal period $T_{signal}$. As such, the sampling frequency in such a situation is approximately twice the transmission signal frequency. In general, a sampling frequency should be at least twice the frequency of a signal being analyzed to be able to characterize that signal; and the "twice" lower limit is often referred to as the Nyquist limit.

As shown in FIG. 16, the example signals 614 output by the receivers 610 are shown to have an underlying "carrier" signal structure (dotted curve superimposed for descriptive purpose) that can have a similar structure as the transmission signal 606. The signals 614 can include a plurality of perturbations about the carrier signal structure. Such perturbations can be the result of the interaction of the transmission signal 606 with some feature of interest in the medium, or due to background noise. Whatever the cause may be, such perturbations may have (and are depicted as having) sub-wavelength feature sizes when compared to the carrier signal structure or the sampling period. As such, sampling of an individual receiver alone will not be able to resolve the fine-feature structures associated with noises or legitimate signals.

When a plurality of receivers are used, the receivers may be arranged so that reflected energies arrive at the receivers at different times. Such arrival time differences can be caused by differences in propagation times due to the pathlength differences and/or velocity differences caused by medium anisotropy. In FIG. 16, such an arrival difference is depicted as ΔT for the receivers 610a and 610b. For a given pair of receivers, the arrival difference ΔT can be made substantially smaller than the sampling period $T_{sampling}$ or the transmission signal period $T_{signal}$.

With an array of receivers, successive arrival differences can be introduced to the receivers. Then, a common sampling of the receivers can have an effect of having the individual receivers sampling different temporal parts of the received signals. Thus in the example configuration 600, the common sampling at time t1 causes the example signal 614c (that arrives late) to be sampled at a given temporal part of the carrier structure (beginning of the cycle in the example). Sampling at time t1 causes the example signal 614b to be sampled at a temporal part of the carrier structure at a time approximately equal to the arrival difference between the receivers 610b and 610c. Similarly, sampling at time t1 causes the example signal 614a to be sampled at a temporal part of the carrier structure at a time that is approximately equal to the arrival difference between the receivers 610a and 610b. When the samplings from the receivers 610a, b, and c are combined, the resulting measurement can be equivalent to sampling at intervals of arrival difference ΔT that is substantially smaller than the common sampling interval of $T_{sampling}$.

One can see that the number of receivers and/or the arrival time difference can be selected so that the effective sampling intervals are distributed between two common sampling intervals (for example, between common sampling times t1 and t2 in FIG. 16). Thus, with proper configuration, an array of receivers can be used to sample the received signals at a frequency that is greater than the common sampling frequency, thereby be able to resolve higher frequency (than the transmission signal frequency) perturbation signal components that are "riding" on the carrier signal structure.

To be able to extract the higher frequency perturbation features, it is preferable in one embodiment to not filter the received signals. In some conventional systems, filtering is used to remove these higher frequency perturbations. Such filtering, however, can filter out a perturbation that is caused by an interaction of interest along with the noise perturbations.

One can see that sampling the received signals at a effectively higher frequency as described above is one aspect of achieving an improved imaging. Such sampling samples both the perturbations of interest and noise. Thus, another aspect of improved imaging includes a method of combining the samplings from different receivers so that the signal to noise ratio of the sampled perturbations is increased.

Figure 17:
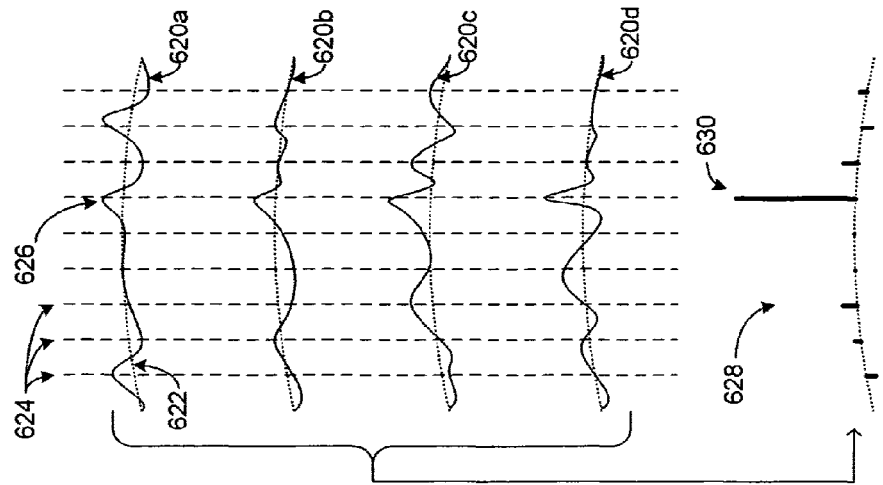
FIG. 17 shows how signals from the multiples receivers can be combined to enhance a fine perturbation feature of interest.

FIG. 17 shows an example of how combination of the samplings from a plurality of receivers can enhance a relatively weak signal from a reflection of interest from the medium. A plurality of example segments of signals 620 are shown superimposed to a carrier signal (dotted curve 622). Each of the example signal segments 620 is shown to include a relatively weak signal of interest 626 among its own set of noise structures. Each signal may have different noise structures since the signal is representative of a path that is different from other signals. If any perturbation within the signal is present in at least some significant portion of the plurality of signals 620, such a perturbation is likely due to some interaction of interest in the medium, and are likely correlated among the signals.

As described above in reference to FIG. 16, such relatively fine-featured perturbations, whether a legitimate signal or noise, are more likely to be sampled with the effective sampling rate that can be substantially greater than that of the common sampling frequency. Thus, an example of a plurality of such effective samplings are depicted as dashed lines 624. It should be understood that the effective sampling lines 624 in FIG. 17 are shown only for the purpose of demonstrating that when properly correlated, the plurality of signals 620 can yield an enhancement of the perturbation of interest over the surrounding noise perturbations. A method of forming such a correlation of signal samplings is described below in greater detail.

It should also be understood that the perturbation of interest 626 in FIG. 17 is depicted as being sampled near the peak for the purpose of description. Because the arrival differences (ΔTs) among the receivers may not be uniform, spacing between the effectively increased samplings may not be uniform. Consequently, samplings of the perturbation 626 may be at different parts of the perturbation peak structure. In one embodiment, such an effect limits the resolution achievable by the effectively increased sampling.

In one embodiment, properly correlated analog signals from the selected receivers can be made to interfere with each other. In such an embodiment, the various analog signals can be provided with delays according to the manner in which the signals are correlated.

In one embodiment, the raw signals from the selected receivers are digitized during the common samplings. The plurality of receivers and their associated sampling electronics are then effectively sampling and digitizing different temporal portions of their respective signals. As shown in FIG. 17, the digitized results are shown to be correlated and combined so as to yield a combined data sequence 628. When the digitized results of the signals are combined properly, individual digitized values of the perturbation of interest 626 combine to yield an enhanced digitized value 630. In contrast, the sampled and digitized noises either combine to generally cancel each other on average, or combine in a manner that is less than that of the correlated perturbation value 630.

In principle, the combining of the signals can be performed with any receivers in the array. However, Applicant's experiences have shown that correlating and combining signals from some combinations of transmitter and receivers yield better results in the quality of images.

Figure 18A:
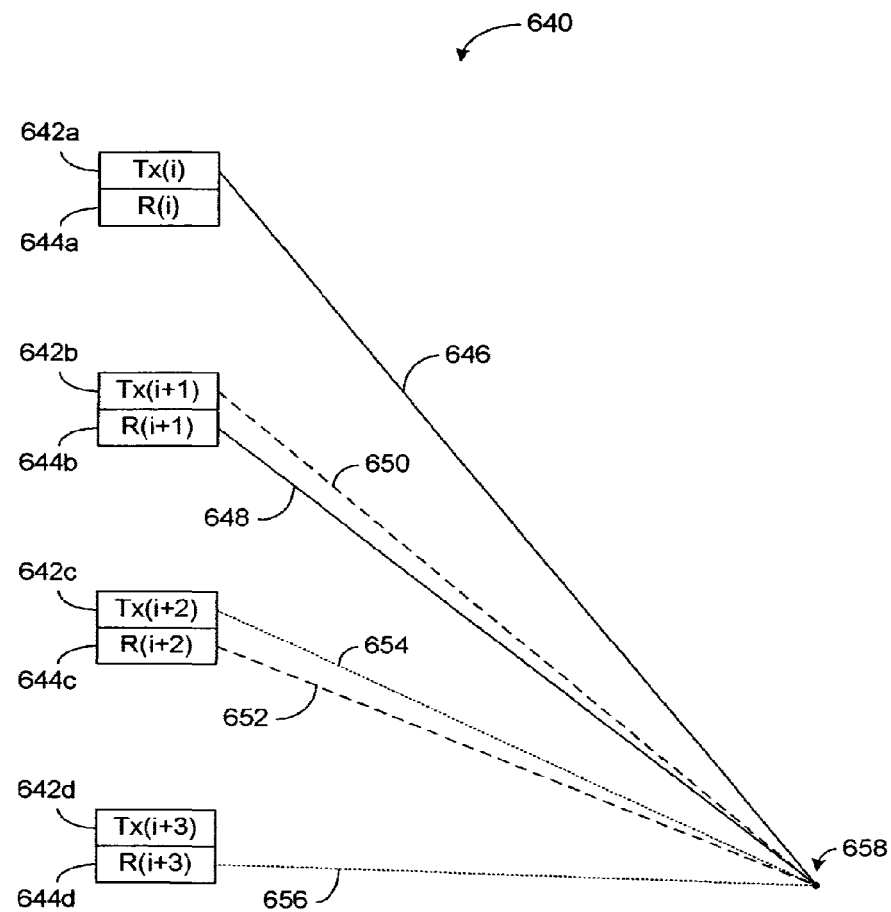
FIG. 18A shows by example how a plurality of signals from receivers that are offset by one from their respective transmitters can be combined.
Figure 18B:
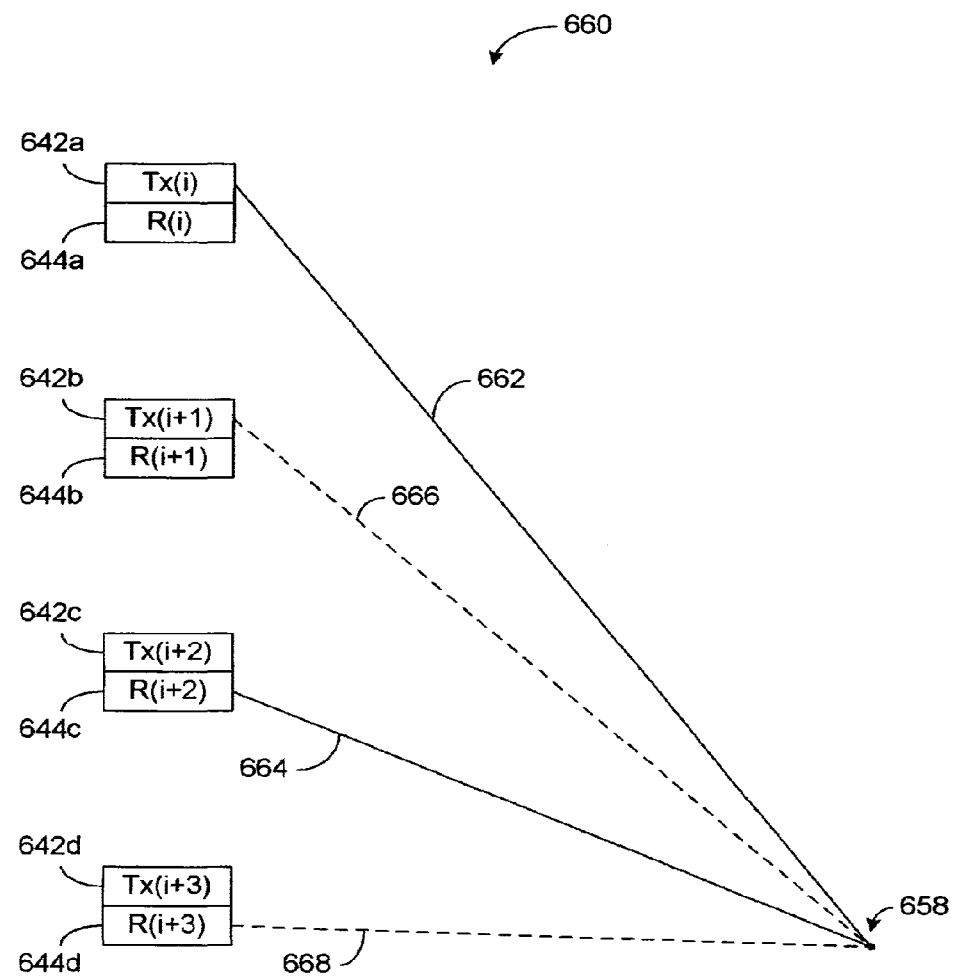
FIG. 18B shows by example how a plurality of signals from receivers that are offset by two from their respective transmitters can be combined.

FIGS. 18A and 18B show two examples of such transmitter-receiver combinations. In FIG. 18A, an example operating configuration 640 has an i-th transmitter 642a transmitting an energy 646, and a receiver (i+1) 644b that is offset by one element spacing receiving a reflected signal 648 (from an arbitrary point 658 in the medium) and generating a signal. Thus, an energy 650 from a transmitter (i+1) 642b is reflected as an energy 652 and received by a receiver (i+2) 644c. Similarly, an energy 654 from a transmitter (i+2) 642c is reflected as an energy 656 and received by a receiver (i+3) 644d. In one embodiment, such transmit-receive combination between transducers offset by one unit provides a substantially "head-on" type of probing of the arbitrary point 658 in the medium.

In FIG. 18B, an example operating configuration 660 has the i-th transmitter 642a transmitting an energy 662, and the receiver (i+3) 644c that is offset by two element spacing receiving a reflected signal 664 (from the arbitrary point 658 in the medium) and generating a signal. Thus, an energy 666 from the transmitter (i+1) 642b is reflected as an energy 668 and received by the receiver (i+3) 644d. Such an offset can provide a more angled probing of the point 658 in the medium.

One can see that such offset pairing of the transmitter and receiver can extend to three, four, or greater offset units. In principle, any offset in the array can be used. In some applications, such a capability can be used to investigate reflections and/or emissions from a given object that are directed towards sidelobe angles.

Figure 19:
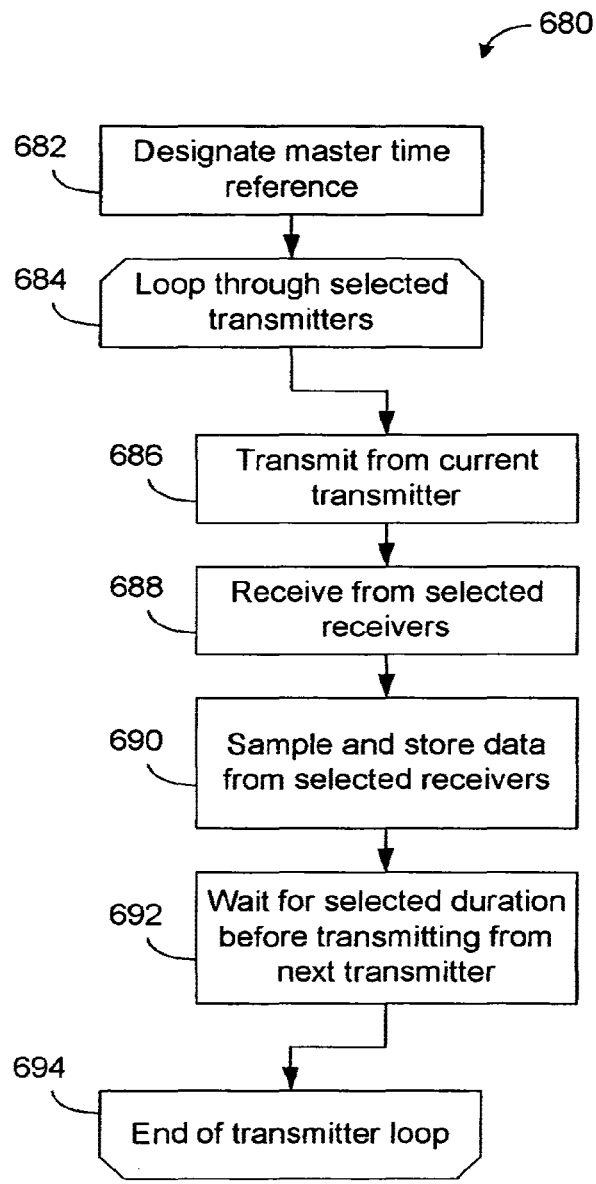
FIG. 19 shows a process for transmitting from one or more transmitters and receiving from a plurality of receivers to allow combination of resulting signals.
Figures 20, 21:
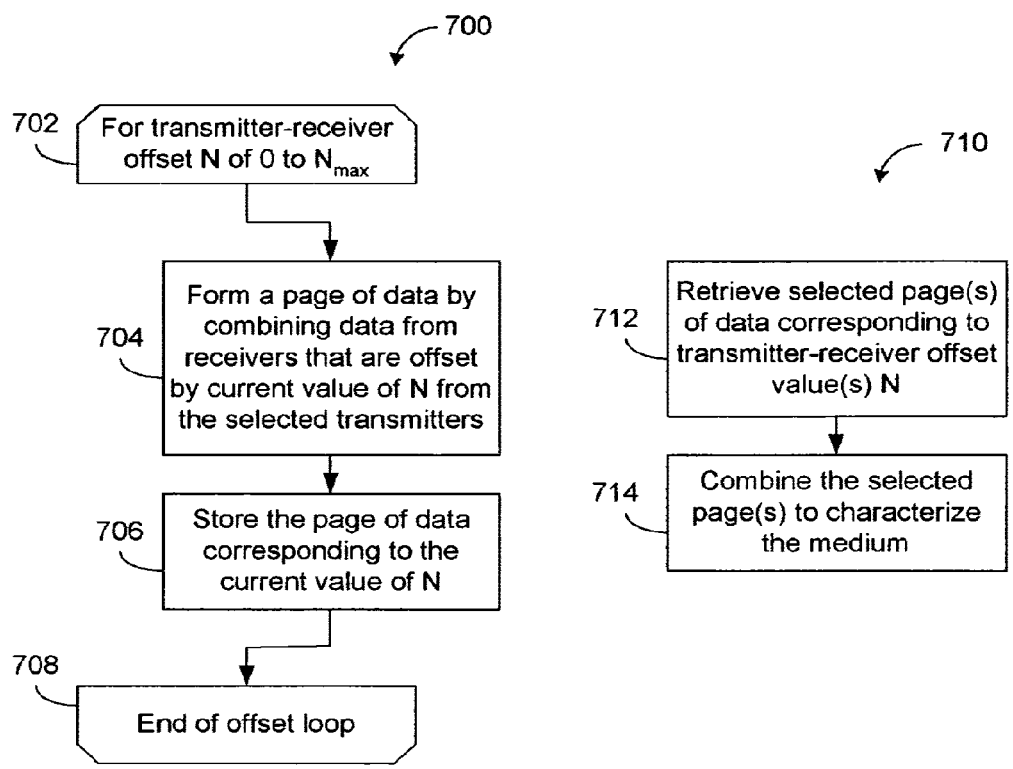
FIG. 20 shows how the received signals from the plurality of receivers can be grouped according to the receivers' respective offsets from transmitters.
FIG. 21 shows how selected groups of data based on the receiver offset can be combined.

FIGS. 19-21 now show various processes that perform the sampling and combining of signals from different transmitter-receiver offsets. FIG. 19 shows one embodiment of a process 680 that transmits from selected transmitters in a sequential manner. In one embodiment, a master time reference is designated in a process block 682. Such a master time can be used for referencing subsequent time-related operations. The process 680 then loops through the selected transmitters (begin loop 684, and end loop 694). In a process block 686, the process 680 induces the current transmitter to transmit energy into the medium. In a process block 688, the return signals are received from selected receivers. In one embodiment, all of the receivers receive return signals impinging on them. In a process block 690, the process 680 samples and stores the resulting data from the selected receivers. In one embodiment, the process 680 may wait for a selected duration before transmitting from the next transmitter.

FIG. 20 now shows one embodiment of a process 700 that combines the sampled data according to different transmitter-receiver offset groups. The process 700 loops through different values of offset N between the transmitter and the receiver of interest (begin loop 702, end loop 708). In one embodiment, the value of offset N ranges from zero to $N_{max}$, with N=0 representing a case where the receiver is in the same assembly as the transmitter. In a process block 704, the process 700 forms a "page" of data by combining data from receivers that are offset by the current value of N from the selected transmitters. In a process block 706, the process stores the page of data corresponding to the current offset value of N.

FIG. 21 now shows one embodiment of a process 710 that uses the page(s) of data to characterize the medium. In a process block 712, the process 710 retrieves selected page(s) of data corresponding to transmitter-receiver offset value(s) of N. In a process block 714, the process 712 combines the selected page(s) to characterize the medium. In one embodiment, characterization of the medium includes formation of an image of the medium.

Figure 22:
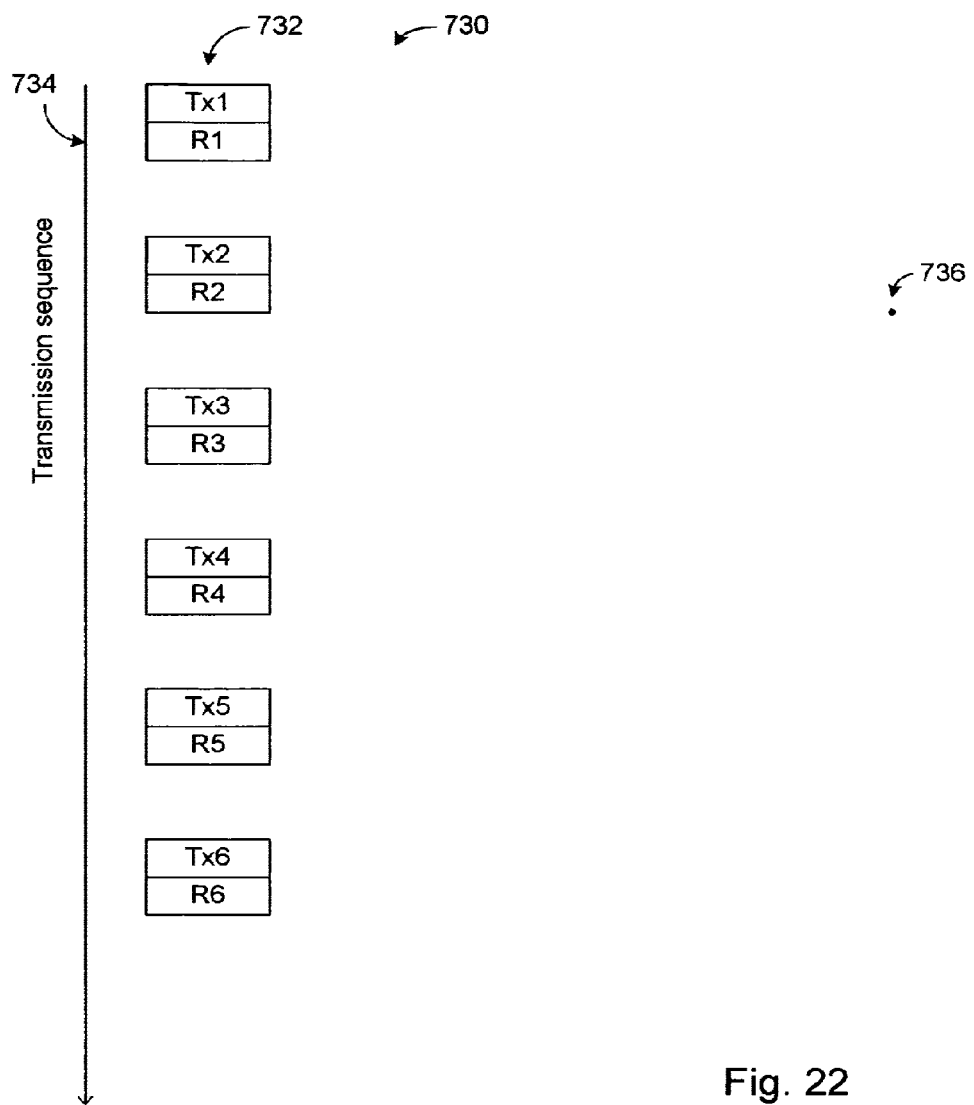
FIG. 22 shows an example of one embodiment of an array of transmitter-receiver pairs where the transmitters are triggered in sequence.

FIGS. 22 to 25 now show a specific example of the data page formation based on the offset of the transmitter and receiver pairs. For the purpose of describing by example, an example operating configuration 730 having six sets of transmitter-receiver assemblies 732 are shown in FIG. 22. It will be understood that such a configuration is only for descriptive purpose, and is not in any way intended to limit the scope of the present teachings.

In one embodiment, each transmitter-receiver assembly includes a transmitter (Tx) and a receiver (R) positioned in a close proximity to the transmitter. As depicted by an arrow 734, the six example transmitters (Tx1 to Tx6) are "fired" in sequence, starting from the first transmitter Tx1.

Also shown in FIG. 22 is an arbitrary point 736 in the medium. In one embodiment, a given transmitter does not transmit until return signals from the medium, including the point 736, would have had time to return to all of the receivers. It will be understood that the arbitrary point 736 is shown to aid in the purpose of description, and a-priori knowledge or assumption of it's location with respect to the array 732 is not required.

Figure 23A:
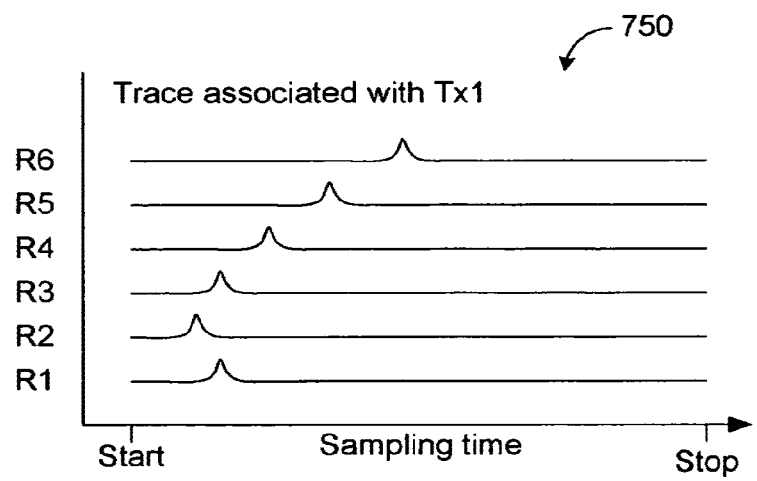
FIGS. 23A and B show a simplified depiction of example signal traces obtained from the example array of FIG. 22.
Figure 23B:
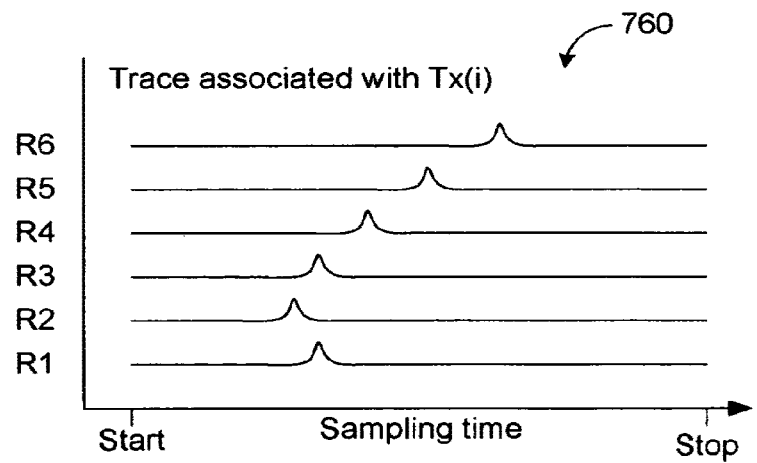

FIGS. 23A and 23B now show examples of simplified raw analog traces from the six example receivers of FIG. 22 in response to receiving of reflected signals due to a given transmitter. For the purpose of describing how a particular perturbation peak can be at different temporal portions of different traces, the traces are depicted to only show the peak. It should be understood that there will likely be other perturbation features in the traces, as described above in reference to FIGS. 16 and 17.

FIG. 23A shows example traces 750 associated with transmission from Tx1. In one embodiment, each of the traces 750 are sampled between a "Start" time and a "Stop" time while being referenced to a master time reference. Thus, if the perturbation peak is assumed to originate from the point 736 in FIG. 22, it will likely arrive at the second receiver R2 first due to that receiver being closer than others. Other receivers will likely receive the perturbation from the same point 736 successively later due to the geometry of the receivers with respect to the point 736. The differences in the arrival times can also be affected by variations in the velocity of sound in the medium. Whatever the cause may be, the arrival times need to compensated for each of the receivers of interest from which the signals (or digitized data therefrom) are combined. One technique of performing such compensation is described below in greater detail.

FIG. 23B shows example traces 760 associated with transmission from an i-th transmitter Tx(i). Similarly, each of the sampled traces 760 can be sampled between a "Start" time and a "Stop" time while being referenced to a time reference. The time reference may or may not be the same as the master time reference described above in reference to FIG. 23A. One can see that because of the proximity of the example point 736 to the second receiver R2, the perturbation signal will likely reach R2 first, followed by successively later arrivals to other receivers spaced from R2. The arrival times within the traces 760 can also be compensated for by the method described below.

From FIGS. 23A and 23B, one can see that signal traces (raw or digitized) from different "sets" associated with different transmitters can be combined. So, if one wants to analyze the return signals from receivers that are offset by one unit from their respective transmitters, the R2 trace from the traces 750 can be combined with the trace (i+1) from the traces 760 (e.g., if i=3, then get trace from R2 and/or R4). Combining signals in such a manner allows enhancement of the perturbation signal while generally maintaining a similar "perspective" with respect to the transmitters.

FIGS. 24 and 25 now show examples of specific possible combinations of offset-one and offset-two data associated with the example operating configuration of FIG. 22. For the purpose of describing the combinations of traces associated with different transmitters, the traces are depicted in a simplified manner as to have already been digitized. Thus, the spikes in the traces represent the digitized values of the sampled perturbation signals (of FIGS. 23A and B).

FIGS. 24A-F show sampled data traces from the receivers associated with each of the six example transmitters. FIGS. 25A-F show the same sampled data traces.

FIGS. 24A-F and G show possible combinations of offset-one data, and FIGS. 25A-F and G show possible combinations of offset-two data. Thus, one can see that the same set of data traces from the receivers associated with each of the transmitters can be used for different offset combinations. Furthermore, offset-three, four, or any number can be achieved in a similar manner as that described in reference to FIGS. 24 and 25.

As shown in FIG. 24A where transmitter Tx1 is used, R2 is the offset-one receiver. As shown in FIG. 24B where transmitter Tx2 is used, R1 and R3 are offset-one receivers; thus, data from either or both receivers can be used. Similar offset-one receivers corresponding to other transmitters are shown in FIGS. 24C to 24F.

FIG. 24G shows a combined data 772 that can result from combination of data 770a-f for offset-one receivers. If the data are combined properly, the combined data 772 can include an enhanced peak 774 that corresponds to a feature of interest. A method for performing such combination is described below in greater detail.

FIGS. 25A-F and G show possible combinations of offset-two data. As shown in FIG. 25A where transmitter Tx1 is used, R3 is the offset-two receiver. As shown in FIG. 25B where transmitter Tx2 is used, R4 is the offset-two receiver. As shown in FIG. 25C where transmitter Tx3 is used, R1 and R5 are offset-two receivers; thus, data from either or both receivers can be used. Similar offset-two receivers corresponding to other transmitters are shown in FIGS. 25D to 25F.

FIG. 25G shows a combined data 782 that can result from combination of data 780a-f for offset-two receivers. If the data are combined properly, the combined data 782 can include an enhanced peak 784 that corresponds to a feature of interest. A method for performing such combination is described below in greater detail.

One can see that other receiver offset (three, four, etc.) data can also be combined in a similar manner. Thus, it will be understood that the example description of the offset-one and offset-two configurations is in no way intended to limit the scope of the present teachings.

FIGS. 26-33 now show how signals from different receivers can be combined so as to yield an enhanced signal of interest. It will be understood that the different receivers can be offset receivers, or simply part of multiple receivers.

FIG. 26 shows that a given receiver 792 can output an example signal 796 having fine perturbations 798 as described above in reference to FIGS. 16 and 17. Such a receiver signal 796 can result from return signals 802 impinging on the receiver 792 from a plurality of directions, including a direction substantially directly in front of it. An imaginary line 790 that extends substantially directly front of the receiver is shown in FIG. 26. For the purpose of description, the line 790 is shown to intersect a layer 794. Although the line 790 and the layer 794 are depicted as being perpendicular, it will be understood that such orientation is not a requirement. A line may be oriented at an angle with respect to the layer. Furthermore, a layer does not need to have a planar shape—it can be curved and form a portion of a shell-like structure about the receiver.

In one embodiment, receiver signals are combined so as to enhance or "focus" on perturbation features positioned generally along the line 790 and within the layer 794. Such "focused" combination of signals from a plurality of receivers can be thought of as a scanline associated with the receiver 792. A plurality of such scanlines associated with a plurality of receivers can then form an image along the scanlines.

Figure 27:
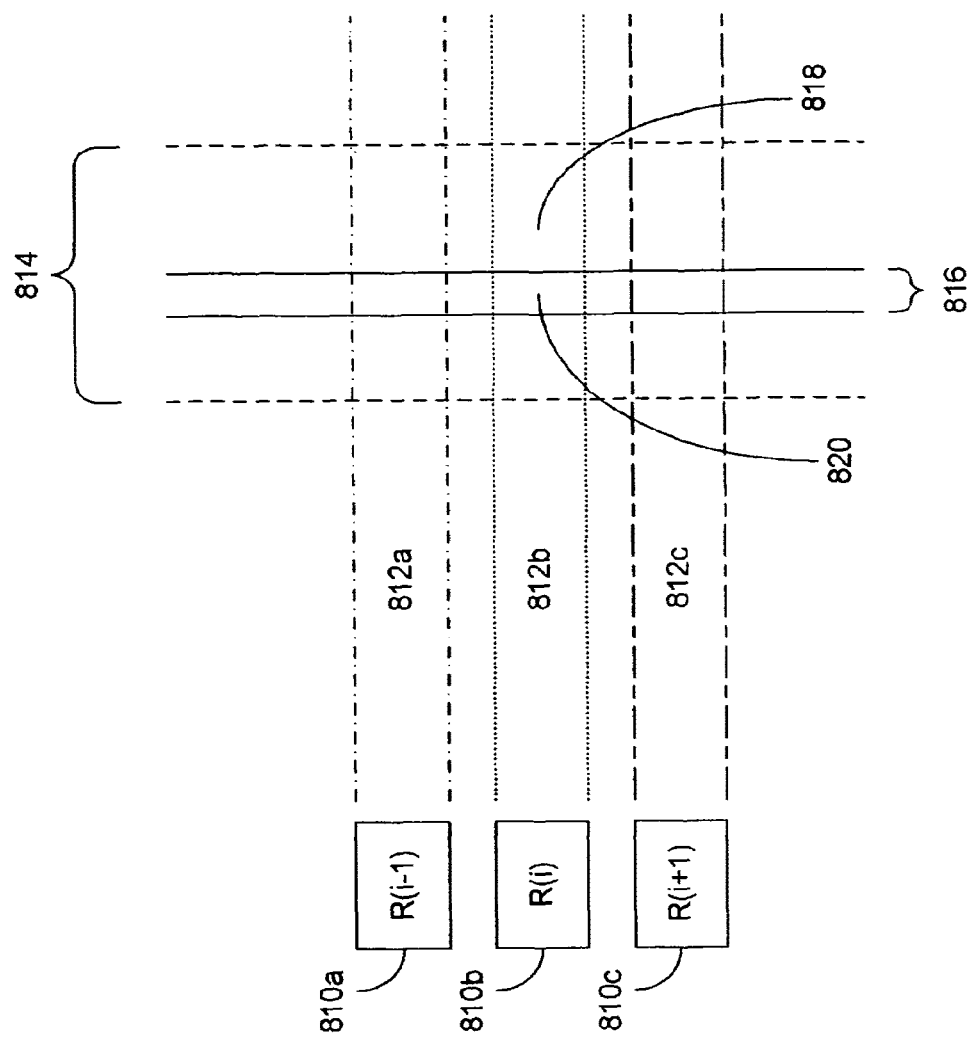
FIG. 27 shows a plurality of scanlines intersecting with a layer such that the plurality of scanlines can be focused to that layer, and wherein the layer can be split into one or more thinner layers so as to allow finer focusing of the plurality of scanlines.

FIG. 27 shows that a plurality of example scanlines 812a-c associated with a plurality of receivers 810a-c can intersect with an example layer 814. It will be understood that areas defined by such intersections are not necessarily equivalent to a "pixel." In some applications, the size of a pixel essentially places a limit on the resolution of the image generated therefrom, whether or not the detector is capable of better resolution.

In FIG. 27, an example area 818 is defined as an intersection area defined by the scanline 812b and the layer 814. In one embodiment, such an area defines a window (or depth-of-field of the scanline) in which a focus is performed. In one embodiment, if the area is not divided up any more, then that area can be considered to be a pixel for the purpose of imaging.

In one embodiment, the size of the focus area defined in the foregoing manner does not need to be fixed. As described below in greater detail, the layer 814 can be initially selected to be relatively large. Once a "coarse focus" is achieved for such a layer, that layer can be split into thinner layers. Then, the scanline(s) can be "fine focused" if desired and/or able to. Thus, as shown in FIG. 27, the layer 814 can be split into thinner layers such as an example layer 816, and a focus area 820 would be associated with that relatively thinner layer.

FIGS. 28 to 30 now show by example how scanlines associated with three example receivers can be brought into focus at different layers. For the purpose of description, an example array of three receivers 810a-c are shown in FIGS. 28A, 29A, and 30A. Associated with the receivers 810a-c are imaginary lines 812a-c that extend therefrom respectively. For the purpose of description, the lines 812a-c are divided into three example layers 822a-c. Also for the purpose of description, a first feature of interest 824 is shown to be located generally in an area defined by the line 812a and the layer 822b. A second feature of interest 826 is shown to be located generally in an area defined by the line 812b and the layer 822a. A third feature of interest 828 is shown to be located generally in an area defined by the line 812c and the layer 822c. For the purpose of showing how different features of interest can be shifted in sampling time, the three features of interest are depicted as triangle 824, circle 826, and square 828.

Figure 29A:
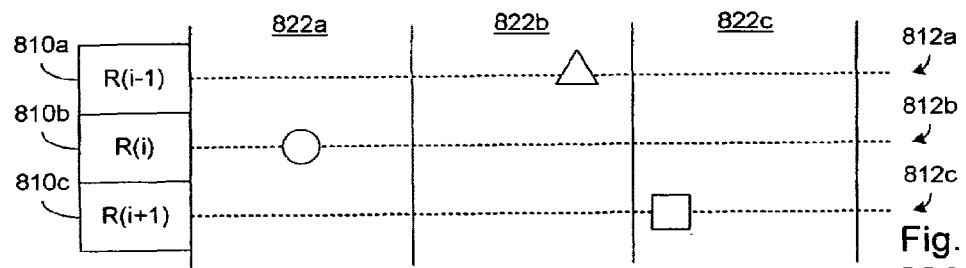
FIG. 29A shows an example of features located along different scanlines and in different layers.
Figure 29B:
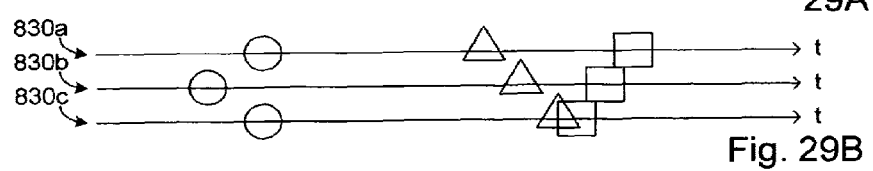
FIG. 29B shows an example of measured signal traces having components associated with the example features of FIG. 29A.
Figure 30A:
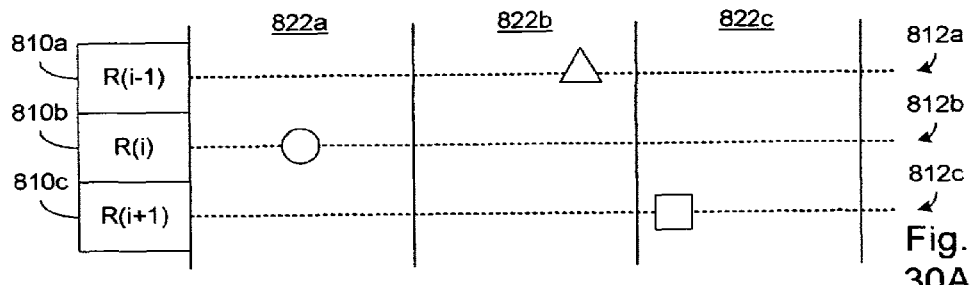
FIG. 30A shows an example of features located along different scanlines and in different layers.
Figure 30B:
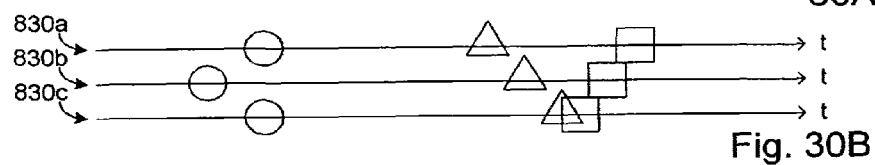
FIG. 30B shows an example of measured signal traces having components associated with the example features of FIG. 30A.

FIGS. 28B, 29B, and 30B are also common, showing that data traces 830a-c associated with their respective receivers 810a-c "sees" the three example features of interest 824, 826, and 828 at relatively different times. For example, the triangle 824 is generally in front of and closest to the receiver 810a. Consequently, as the data trace 830a associated with the receiver 810a shows, the receiver 810a will likely receive a return signal from the triangle 824 first, followed by the receiver 810b, which in turn is followed by the receiver 810c. Similarly, the circle 826 is generally in front of and closest to the receiver 810b. Consequently, as the data trace 830b shows, the receiver 810b will likely receive a return signal from the circle 826 first, and the receivers 810a and 810c after that.

As shown in FIGS. 28A, 29A, and 30A, the receivers 810a-c are depicted as being arranged in an ordered array. It will be understood that such a depiction is only for the purpose of describing the concept of relative arrival times of return signals to the different receivers, and how such signals can be combined to form a focused scanline. In particular, it will be understood that although the example receivers 810a-c are shown in sequence, they do not necessarily need to be as such physically. For example, different receiver-offset data can be combined as described above; and in such situations, the receivers whose signals are being combined may not be next to or even relatively close to each other. Thus, the arrangement of the receivers 810a-c should be considered to represent a logical arrangement for the purpose of description.

FIG. 28C shows an example focused layer 838a for a scanline 834 associated with the receiver 810a. Depicted along with the scanline 834 are relative peak heights 836 associated with the combined return signals from the three features 824, 826, and 828 when the scanline is in focus. Relative shifting of return signal traces to achieve the focus is shown as a set 832 of shifted traces. It will be noted that one does not need to know how much to shift one trace relative to another trace beforehand to achieve a focus. A method for determining a focused state from different combinations of shifting is described below in greater detail. For the purpose of describing the result of such focusing for a given scanline in reference to FIGS. 28-30, the scanlines are depicted as being brought into focus.

Similarly, FIG. 28D shows an example focused layer 838b for the scanline 834 associated with the receiver 810a. Depicted along with the scanline 834 are relative peak heights 836 associated with the combined return signals from the three features 824, 826, and 828 when the scanline is in focus. Relative shifting of return signal traces to achieve the focus is shown as a set 840 of shifted traces.

Similarly, FIG. 28E shows an example focused layer 838c for the scanline 834 associated with the receiver 810a. Depicted along with the scanline 834 are relative peak heights 836 associated with the combined return signals from the three features 824, 826, and 828 when the scanline is in focus. Relative shifting of return signal traces to achieve the focus is shown as a set 844 of shifted traces.

In FIG. 28D, one can see that the focused layer 838b results in an enhance peak 842 corresponding to the aligning (by proper shifting of the data traces) of the triangle 824. Such enhanced peaks can be utilized to determine whether a scanline is in focus in a given layer. Such determination is described below in greater detail.

Also note that for the line 812a associated with the receiver 810a, the first and third layers 822a and 822c do not have any features. Thus, an image resulting from a properly focused scanline should not show features in those two layers 822a and 822c. In one embodiment, such a result can be achieved by making a threshold cut on the peak(s) in a given focused layer so that peaks below that threshold are not processed for image formation. For example, if one was to set the threshold so as to accept the enhance peak 842 but reject lower peaks, the first and third focused layers 838a and 838c can form focus areas having substantially null images.

Figure 29C:
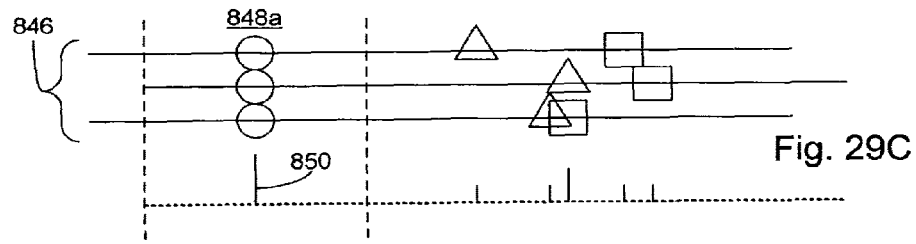
FIGS. 29C-E show by example "in-focus" combinations at various layers for the signals traces to form the scanline associated with the second example receiver.

FIG. 29C shows an example focused layer 848a for a scanline associated with the receiver 810b. Depicted along with the scanline are relative peak heights associated with the combined return signals from the three features 824, 826, and 828 when the scanline is in focus. Relative shifting of return signal traces to achieve the focus is shown as a set 846 of shifted traces.

Figure 29D:
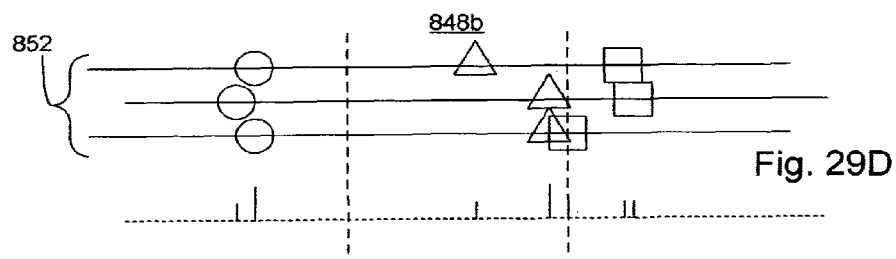

Similarly, FIG. 29D shows an example focused layer 848b for the scanline associated with the receiver 810b. Depicted along with the scanline are relative peak heights associated with the combined return signals from the three features 824, 826, and 828 when the scanline is in focus. Relative shifting of return signal traces to achieve the focus is shown as a set 852 of shifted traces.

Figure 29E:
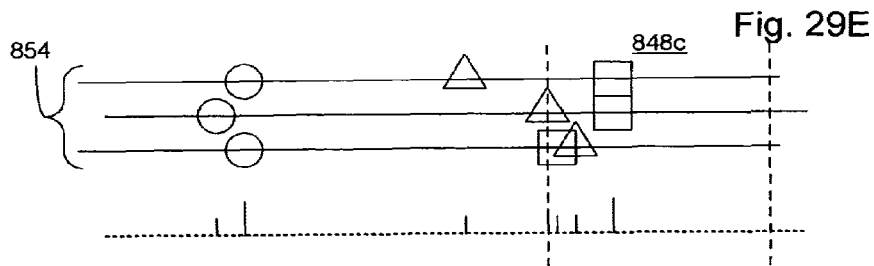

Similarly, FIG. 29E shows an example focused layer 848c for the scanline associated with the receiver 810b. Depicted along with the scanline are relative peak heights associated with the combined return signals from the three features 824, 826, and 828 when the scanline is in focus. Relative shifting of return signal traces to achieve the focus is shown as a set 854 of shifted traces.

In FIG. 29C, one can see that the focused layer 848a results in an enhanced peak 850 corresponding to the aligning (by proper shifting of the data traces) of the triangle 826. Such an enhanced peak can be used to form an image for the area associated with the line 812b and the layer 848a.

Figure 30C:
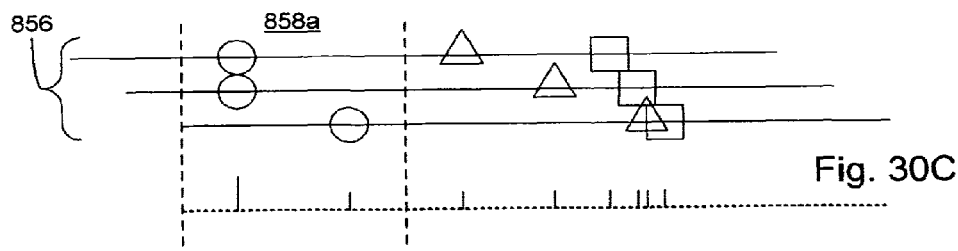
FIGS. 30C-E show by example "in-focus" combinations at various layers for the signals traces to form the scanline associated with the third example receiver.

FIG. 30C shows an example focused layer 858a for a scanline associated with the receiver 810c. Depicted along with the scanline are relative peak heights associated with the combined return signals from the three features 824, 826, and 828 when the scanline is in focus. Relative shifting of return signal traces to achieve the focus is shown as a set 856 of shifted traces.

Figure 30D:
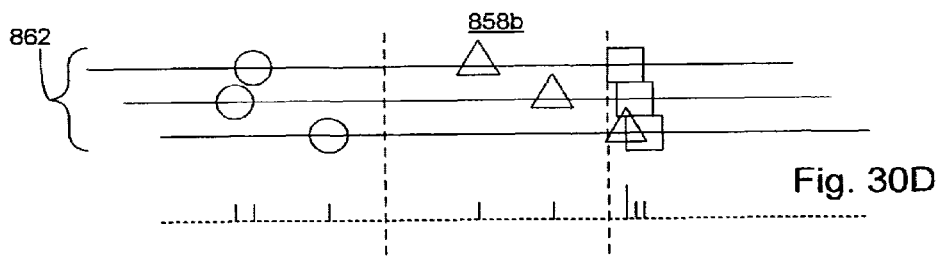

Similarly, FIG. 30D shows an example focused layer 858b for the scanline associated with the receiver 810c. Depicted along with the scanline are relative peak heights associated with the combined return signals from the three features 824, 826, and 828 when the scanline is in focus. Relative shifting of return signal traces to achieve the focus is shown as a set 862 of shifted traces.

Figure 30E:
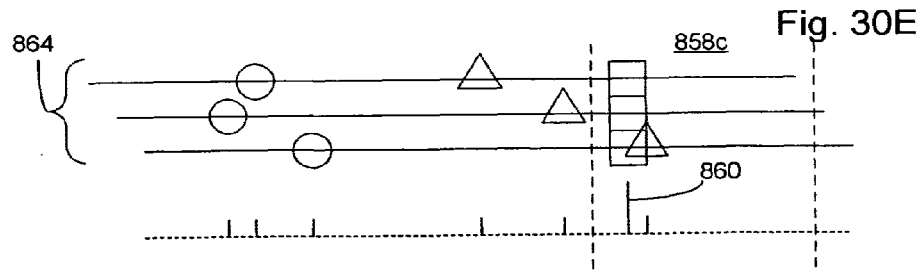

Similarly, FIG. 30E shows an example focused layer 858c for the scanline associated with the receiver 810c. Depicted along with the scanline are relative peak heights associated with the combined return signals from the three features 824, 826, and 828 when the scanline is in focus. Relative shifting of return signal traces to achieve the focus is shown as a set 864 of shifted traces.

In FIG. 29E, one can see that the focused layer 858c results in an enhanced peak 860 corresponding to the aligning (by proper shifting of the data traces) of the square 826. Such an enhanced peak can be used to form an image for the area associated with the line 812c and the layer 858c.

In one embodiment, a layer closest to a given receiver is focused first, followed by successive layers therefrom. Focusing of a given layer allows determination of propagation time within that layer, since the amount of shifting of various data traces depends on how much differences there are in the propagation times. Thus, a given layer is brought into focus when the proper amount of shifting is applied (i.e., when the proper propagation time is determined for that layer).

In one embodiment, the foregoing focusing process and/or the focus results therefrom can be implemented with physical movements of one or more transducer elements. For example, arrays having movable elements similar to that of adaptive optics can be adjusted to either aid the focusing process, or to re-position the elements so that subsequent focusing process can be achieved more efficiently. In one specific example, suppose that a focused section of a scanline is achieved when data traces from one or more receivers are shifted so as to be near their limits. In such cases, the corresponding receivers may be moved so as to introduce changes in propagation times thereto, so that likely "focused" sections of the corresponding data traces are now located more centrally, thereby providing more "working" room in the shifting of data traces.

By focusing on the closest layer, the propagation time for that layer is determined. Focusing of the next layer can then be facilitated by the knowledge of the first layer. This building of propagation time information can build successively outward away from the receiver.

It will be understood that the shifting of data traces described for the purpose of combining those data traces refer to shifting in time. In one embodiment where each data trace includes a series of digital representation of samplings, each sampling has a time associated with it. Thus, time-shifting can be in the form of shifting data trace based on such "time stamp" of the samplings. Based on the foregoing, a "time-shift combination" operation includes shifting of time or phase associated with portions of a plurality of data traces with respect to each other. For example, if a scanline is being focused at a given layer, temporal ranges of data traces being combined can be identified (for example, by an initial estimation based on geometry). Then, digital data within those ranges can be shifted with respect to each other and combined to yield a quality value associated with that combination.

Figure 31A:
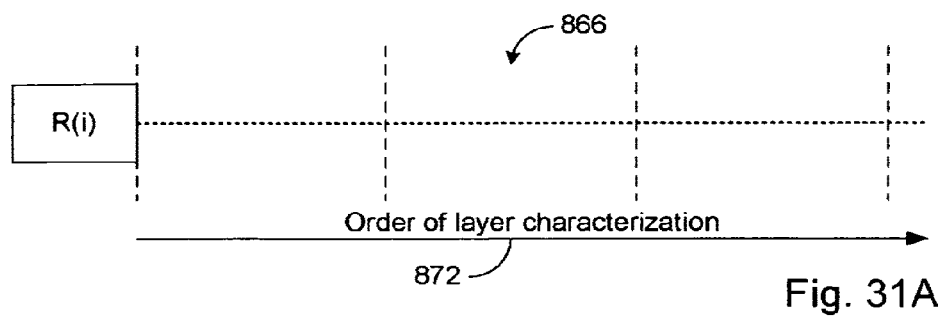
FIGS. 31A-C show that in one embodiment, a scanline can be focused from the layer closest to the receiver, and that a given layer can be split into finer layers for finer focusing.
Figure 31B:
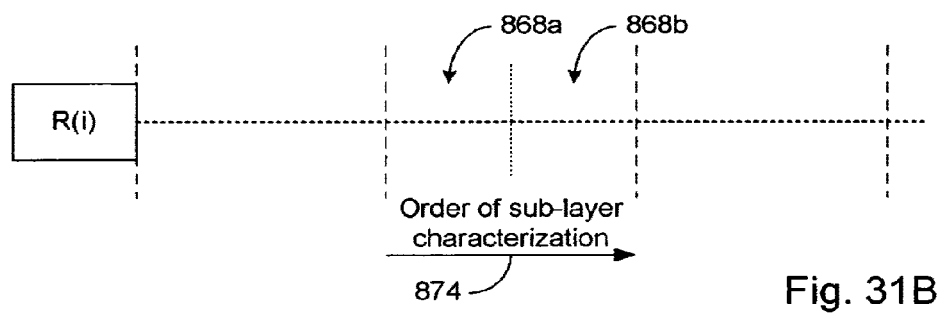
Figure 31C:
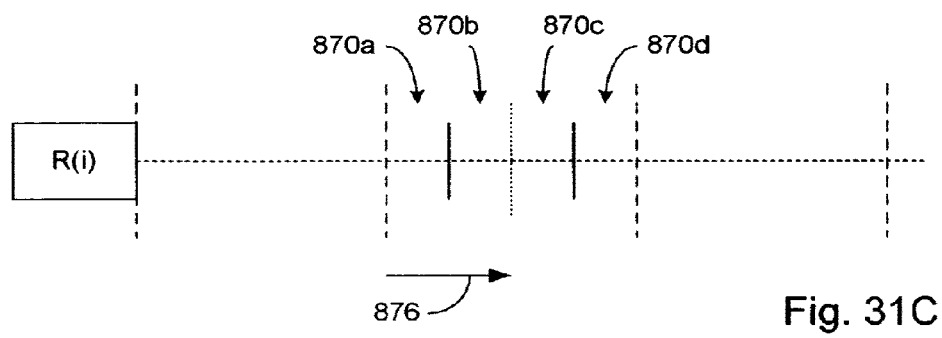

FIGS. 31A-C show such a successive layer characterization method. In FIG. 31A, an arrow 872 directed away from a receiver indicates the order of layer characterization. Also in FIG. 31A, an example layer 866 is shown. If that layer is to be split for finer focusing, such as layers 868a and 868b in FIG. 31B, characterization of those sub-layers can be characterized successively beginning from the sub-layer closest to the receiver (as indicated by an arrow 874). Similarly, each of the sub-layers 868 can be split further into layers 870*a-b* and 870*c-d*. Again, such layers can be characterized successively beginning from the one closest to the receiver (as indicated by an arrow 876).

It will be understood that the foregoing successive layer characterization (beginning with the closest layer to the receive) is just one example of focusing on the plurality of layers. As described herein, focusing on a given layer does not necessarily depend on the knowledge of another layer. Thus, focusing can begin at any layer in the medium without departing from the scope of the present teachings.

Figure 32:
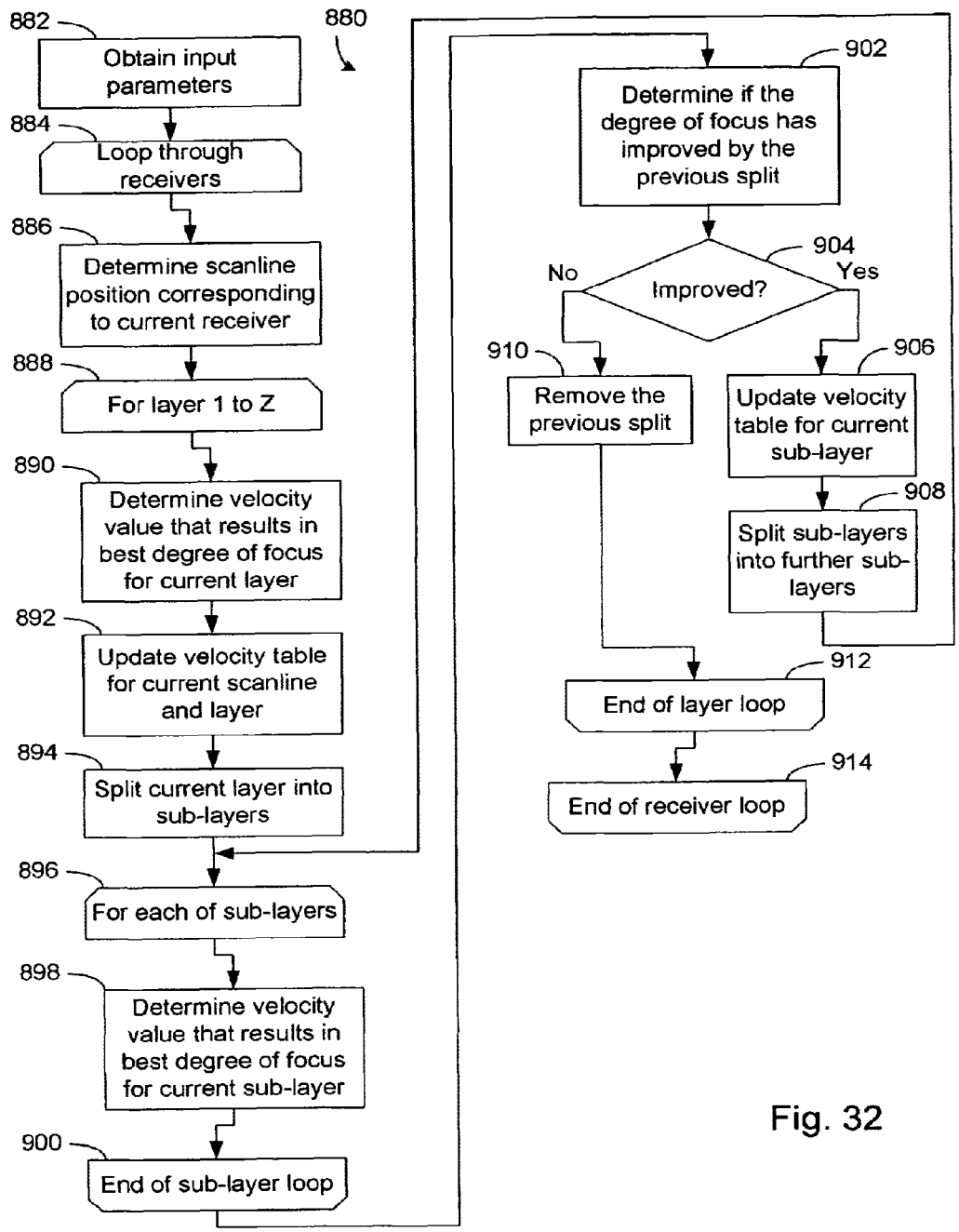
FIG. 32 shows a process for focusing a plurality of scanlines in a plurality of layers, such that a given layer can be split for finer focusing if advantageous to do so.
Figure 33:
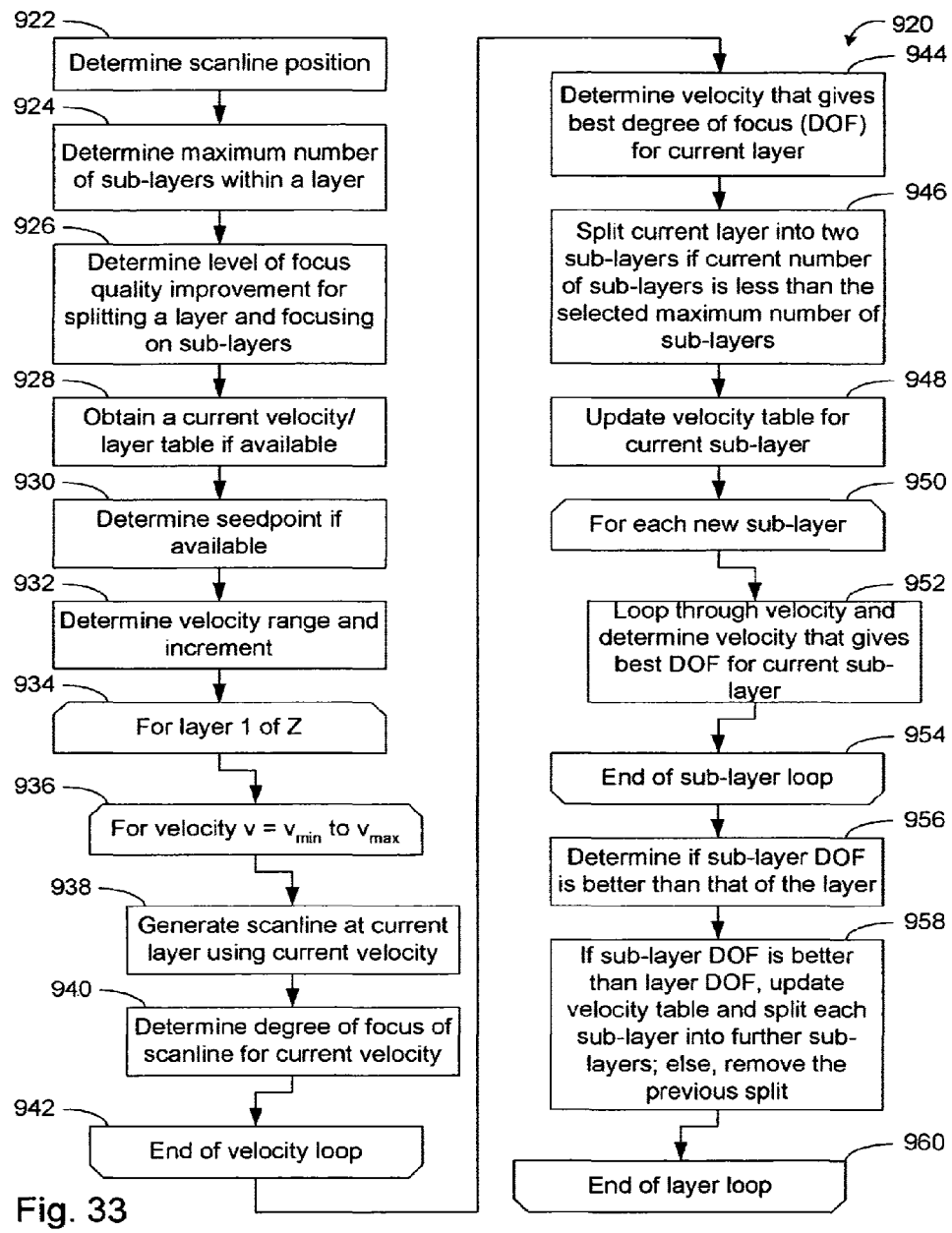
FIG. 33 shows a more specific example of the process of FIG. 32.

FIGS. 32-33 now show how a scanline can be focused at a given layer—that is, how signal traces from different receivers can be combined so as to optimally enhance perturbation features of interest. For the purpose of describing the focusing technique, "velocity" (generally inversely proportional to time) is used to characterize the propagation time within a given layer. It should be noted that in the focusing technique of FIG. 32-33, a prior knowledge of velocity is not necessary.

FIG. 32 shows a process 880 for determining focused scanlines for one or more receivers at different layers. In one embodiment, the process 880 further includes a finer-focusing capability that splits a given layer if that split provides an improved scanline focus quality. The process 880 in general includes a process block 882 where input parameters are obtained. Some of the input parameters are described in a more specific process in reference to FIG. 33.

The process 880 then loops through the receivers (end loop 914). In a process block 886, the process 880 determines the position of a scanline corresponding to the current receiver. For the current receiver, the process 880 loops through each of the Z layers (end loop 912). In one embodiment, the layers are successively looped through from layer one to layer Z, with layer one being the closest to the receiver.

For the current receiver and the current layer, the process 880 in a process block 890 determines a velocity value that results in the best degree of focus for the current scanline in the current layer. Various methods of determining the degree of focus selecting the "best" therefrom are described below in greater detail. As previously described, a prior knowledge of velocity value is not necessary. However, providing a likely range of velocity values may result in a more efficient combinatoric computation for combining and determining the degree of focus.

The process 880 in a process block 890 then updates the velocity data corresponding to the current scanline and the layer. Such data can be stored as a table, or any manner that allows retrieval for later use.

In one embodiment, the current layer is initially split into sub-layers in a process block 894, and focusing is performed in each of the newly created sub-layers in a sub-layer loop 896 (end loop 900). Each of these sub-layers may be further split, and each of those newly created layers may undergo similar loop. This successive splitting process may continue further. Thus, for the purpose of description, the sub-layer loop 896 is depicted as a module that can be accessed whenever a set of sub-layers are looped through.

Within the sub-layer loop 896, the process 880 in a process block 898 determines a velocity value that results in the best degree of focus for the current sub-layer. Whether that velocity value will replace the existing velocity value for the area overlapping the current sub-layer depends on whether the current sub-layer focus is an improvement. In one embodiment, such determination can be made on a sub-layer by sub-layer basis, or collectively for the set of sub-layers. As an example, an average of the degrees of focus for the sub-layers can be compared to the degree of focus for the parent layer. For the purpose of description, the process 880 is shown to determine if the degree of focus has improved collectively by the split in a process block 902.

Once such determination is made, the process 880 in a decision block 904 determines whether the focus has improved by the split. If the answer is "yes," then the process 880 in a process block 906 updates the velocity table for the sub-layers of the current layers. To see if the focus can be made even finer, thereby improving the resolution, each of the current sub-layers are further split in a process block 908, and focusing is performed on each of the newly created sub-layers by invoking the sub-layer loop 896. If the answer in the decision block 904 is "no," then the process 880 removes the previous split in a process block 910, since the finer "focus" did not yield a better result.

FIG. 33 now shows a more specific example process 920 of how the process 880 of FIG. 32 can be implemented. For the purpose of simplicity, the process 920 is described for one given receiver. But as shown in FIG. 32, such a process can be looped over a plurality of receivers.

The process 920 in a process block 922 determines the position of a scanline associated with the receiver being analyzed. In a process block 924, a maximum number of sub-layers within a given layer is obtained. In one embodiment, that maximum number places a limit on the extent of splitting for finer focusing. In a process block 926, the process 920 obtains a level of focus quality improvement to trigger additional splitting for finer focusing. In a process block 928, the process 920 obtains a current velocity table for the layers if available and/or desired. In a process block 930, a seedpoint (such as a value representative of a lowest expected velocity) is obtained if available and/or desired. In a process block 932, the process 920 obtains the range and increment of velocity for determining the velocity associated with the best degree of focus.

The process 920 then loops through layers one to Z in a loop 936 (end loop 960). For each current layer, the process 920 loops through the range of velocity values in a loop 936 (end loop 942). For the current velocity value, the process 920 generates a scanline at the current layer in a process block 938. The process 920 then determines a degree of focus of the scanline for the current velocity in the process block 940.

Once the process loop 936 is completed, the process 920 in a process block 944 determines a velocity that results in the best degree of focus for the current layer. In a process block 946, the process 920 splits the current layer into two sub-layers if the current number of sub-layers is less than the selected maximum number of sub-layers (obtained in the process block 924). In a process block 948, the velocity table is updated with the velocity value that gave the best degree of focus for the current layer.

The process 920 then loops through the newly created sub-layers (if any) in the process block 946 in a loop 950 (end loop 954). For each sub-layer, the process 920 in a process block 952 loops through the velocity range and determines a velocity value that results in the best degree of focus for that sub-layer in a manner similar to that of the loop 936. The process 920 then determines if degree of focus associated with the sub-layers is better than that of the parent layer in a process block 956. In one embodiment, the new degree of focus is considered to be better than that of parent layer if it exceeds the level of focus quality improvement obtained in the process block 926.

If the sub-layer degree of focus is better than the parent layer degree of focus, the process 920 in a process block 958 updates the velocity table and splits each of the current sub-layers into two sub-layers. Again, this splitting can be limited by the maximum number of sub-layer as determined in the process block 924. If the sub-layer degree of focus is not better than the parent degree of focus, the process 920 removes the previous split and retains the parent layer level of focus.

Figure 34A:
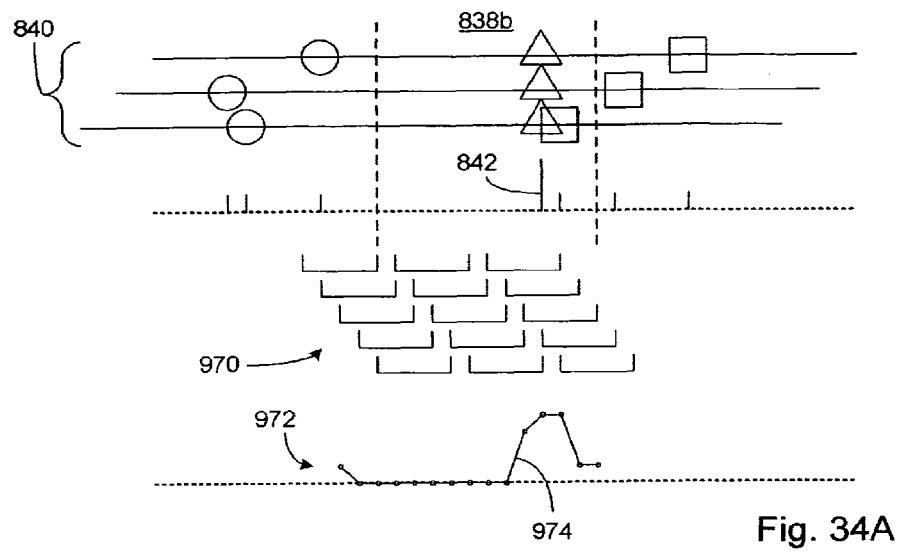
FIGS. 34A-B show some of the many possible ways of combining various signal traces to obtain a best in-focus scanline at a given layer.

In the description herein in respect to FIGS. 26-33, various references are made about focusing, degree of focus, and the like. FIGS. 34A and B now show by example how a focus can be achieved by determining a parameter representative of the best degree of focus. A "focus" associated with an array of signal values can be determined in a variety of ways. For example, some autofocus cameras compare relative contrasts of adjacent or nearby signal values—the reason being that a sharply focused image will have more of a sudden change in the contrast. A similar method can be applied for determining the degree of focus for a scanline of interest.

In one embodiment, the splitting of layers can provide a substantial advantage in how effectively a given volume can be imaged. As an example, suppose that a volume includes a relatively small group of features of interest localized in a relatively small region. The rest of the volume is substantially homogeneous for the purpose of propagating signals. Such homogeneous portions likely will not need to be split, since the velocity therein is substantially uniform. When the small inhomogeneous region is encountered, it can be split into smaller layers to allow characterization of sub-regions with different velocity values. Thus, one can see that the combining process does not need to waste time attempting to split the homogeneous portion. Moreover, the inhomogeneous region can be characterized better by the splitting method, thereby allowing improved characterization of the volume.

FIG. 34A shows the shifted data trace set 840 corresponding to "in focus" configuration as described above in reference to FIG. 28D. FIG. 34A further shows one of a number of possible ways of determining the degree of focus for the trace combination set 840. In one embodiment, a running average of the combined scanline is obtained for a selected window. In one embodiment, such a window may overlap the focus layer 838b and extend beyond. In one embodiment, the window may be defined as temporally substantially similar to the boundaries corresponding to the focus layer 838b.

In one embodiment, the running averages are formed by a plurality of partially overlapping averaging intervals 970. Average values 972 associated with the intervals 970 are depicted at the approximate centers of the intervals 970.

Figure 34B:
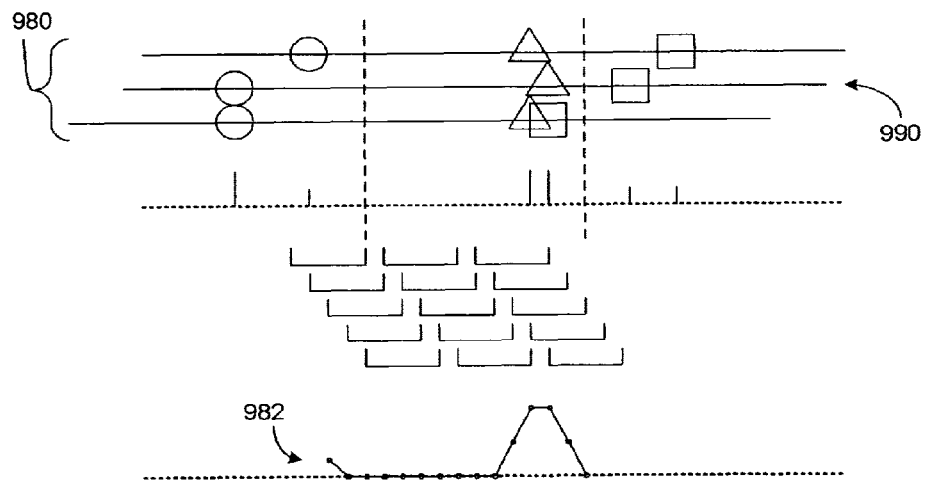

FIG. 34B show a shifted data trace set 980 corresponding to "almost in focus" configuration. In particular, the combination 980 has the second trace (990 in FIG. 34B) not shifted as much as that of FIG. 34A. Average values 982 associated with the running average intervals are also shown.

In one embodiment, a best degree of focus can be determined by looking for the greatest change in the running average value. Thus in the example scanlines shown in FIGS. 34A and B, a change in average denoted as 974 is has the greatest slope (i.e., the greatest "contrast") within the window. The data trace combination 840 corresponds to the greatest slope 974, and thus represents the "in focus" scanline having the best degree of focus value (in this example, the greatest slope).

In another embodiment, a best degree of focus can be determined by looking for the greatest sum of average values within the window. In FIGS. 34A and B, one can see that the average values 972 add up to a greater value than that of the average values 982. Thus, the data trace combination 840 can be said to be the "in focus" scanline having the best degree of focus value (in this example, the sum of average values).

One can see that there are many other ways of determining the best degree of focus. Thus, it will be understood that the two examples described above in reference to FIGS. 34A and B are not to be construed as limiting the scope of the present teachings. Furthermore, "quality value" can represent the various degrees of focus described herein, and "best quality value" can represent the corresponding "best degree of focus." It will be understood that the term "best" does not necessarily mean a value having the largest value. It can mean a value having the smallest value, or any value that represents a particular combination having the desired property for the purpose of assigning to a scanline.

Figure 35A:
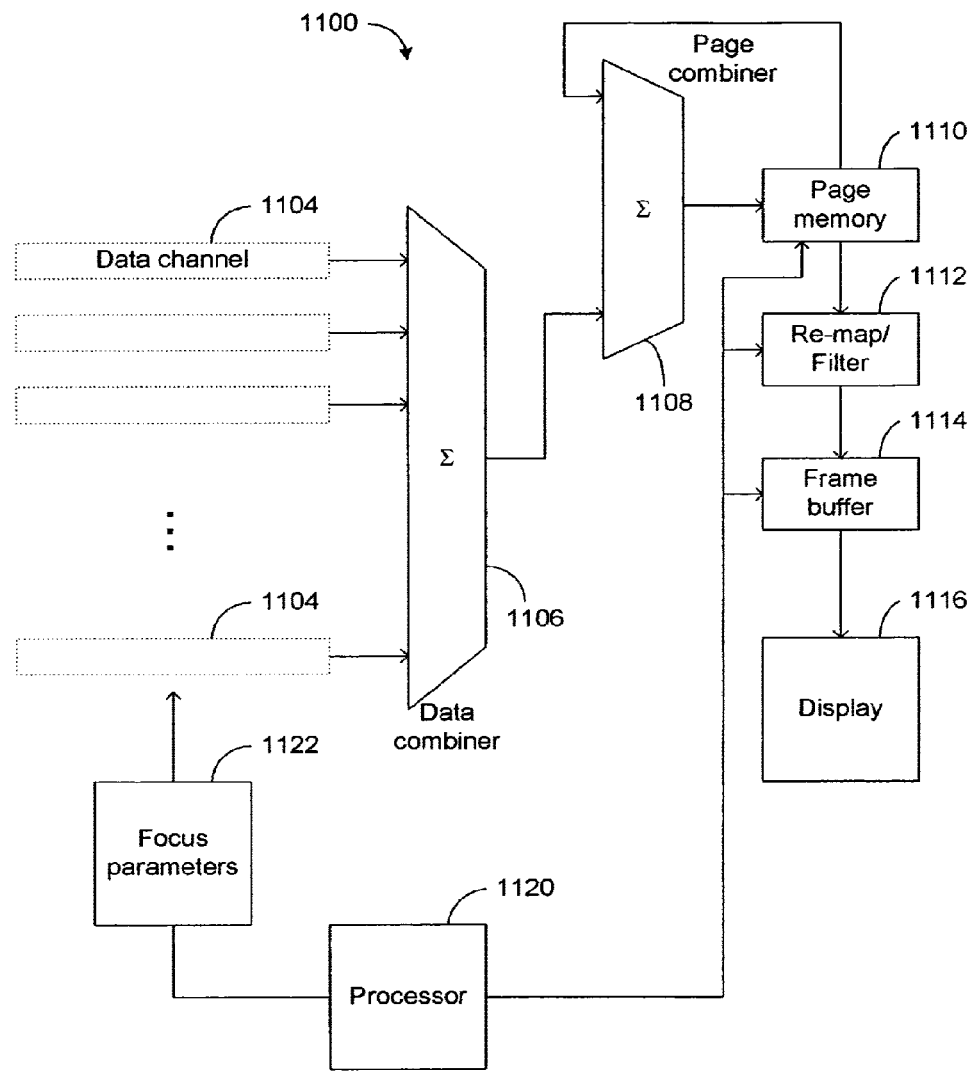
FIGS. 35A and B show by way of example one embodiment of a signal processing system that combines signals from the plurality of receivers.

FIGS. 35A and B now show block diagrams of one embodiment of a signal processing assembly 1100 that can perform various functions described herein (such as obtaining data traces from receivers, digitally sampling, and combining the digitally sampled data). As shown in FIG. 35A, one embodiment of the assembly 1100 includes a plurality of data channels 1104 that are input into a data combiner 1106. Each data channel 1104 forms a stream of digital data corresponding to data traces from one or more receivers in a manner described below in greater detail. Thus in one embodiment, such digital data represents digital echo signals having amplitudes and time information of samplings of the data traces.

As shown in FIG. 35A, such digital data from the data channels 1104 are combined by a data combiner 1106. In one embodiment, the data combiner 1106 combines the digital data according to the relative orientation of the receivers with respect to transmitters. For example, data corresponding to offset-one receivers can be combined as one set of data. In one embodiment, such combining of data is performed by parallel processing (as depicted in FIG. 35A) so as to allow timely processing of a relatively large amount of data.

In one embodiment, each stream of data in the channel 1104 is associated with a receiver and a transmitter. Thus, focus information can be associated with such receiver and/or transmitter can be provided to the channel 1104 by a focus parameter database 1122. For example, for pixel imaging, the focus information can include the transmitter and receiver alignment sets can be provided. For focusing on a layer along a scanline, the focus information can include a default velocity information for the receivers.

Thus in one embodiment, an output from the data combiner 1106 represents group(s) of data corresponding to different receiver-transmitter combinations. As shown in FIG. 35A, such combined data can form a "page" of data, and such pages of data can be further combined by a page combiner 1108. For example, pixel intensity as determined by selected groups of transmitter-receiver combinations (pages) can be further combined to enhance the real signal from that pixel, by using the transmitter-pixel and pixel-receiver geometries. In another example, pages of data can be combined with respect to a scanline for a receiver at a given layer, such that each combination yields a degree of focus or a quality value. As described above, a "best" degree of focus or quality value can be determined in a number of ways to select a "best" scanline for the receiver.

As shown in FIG. 35A, an output from the page combiner 1108 can be stored in a page memory 1110. Such stored page combinations can be refined further as shown. For example, the finer focusing by layer-splitting described above can be facilitated by such a feature.

In one embodiment, the page memory 1110 can include a plurality of "final" pages of data that can be used for imaging. As shown in FIG. 35A, such pages of data can be processed further to clean up the data and/or map to a display representation in a re-map/filter block 1112. Output from the block 1112 can be built into a frame of image in a frame buffer 1114, and be displayed via a display 1116.

Figure 35B:
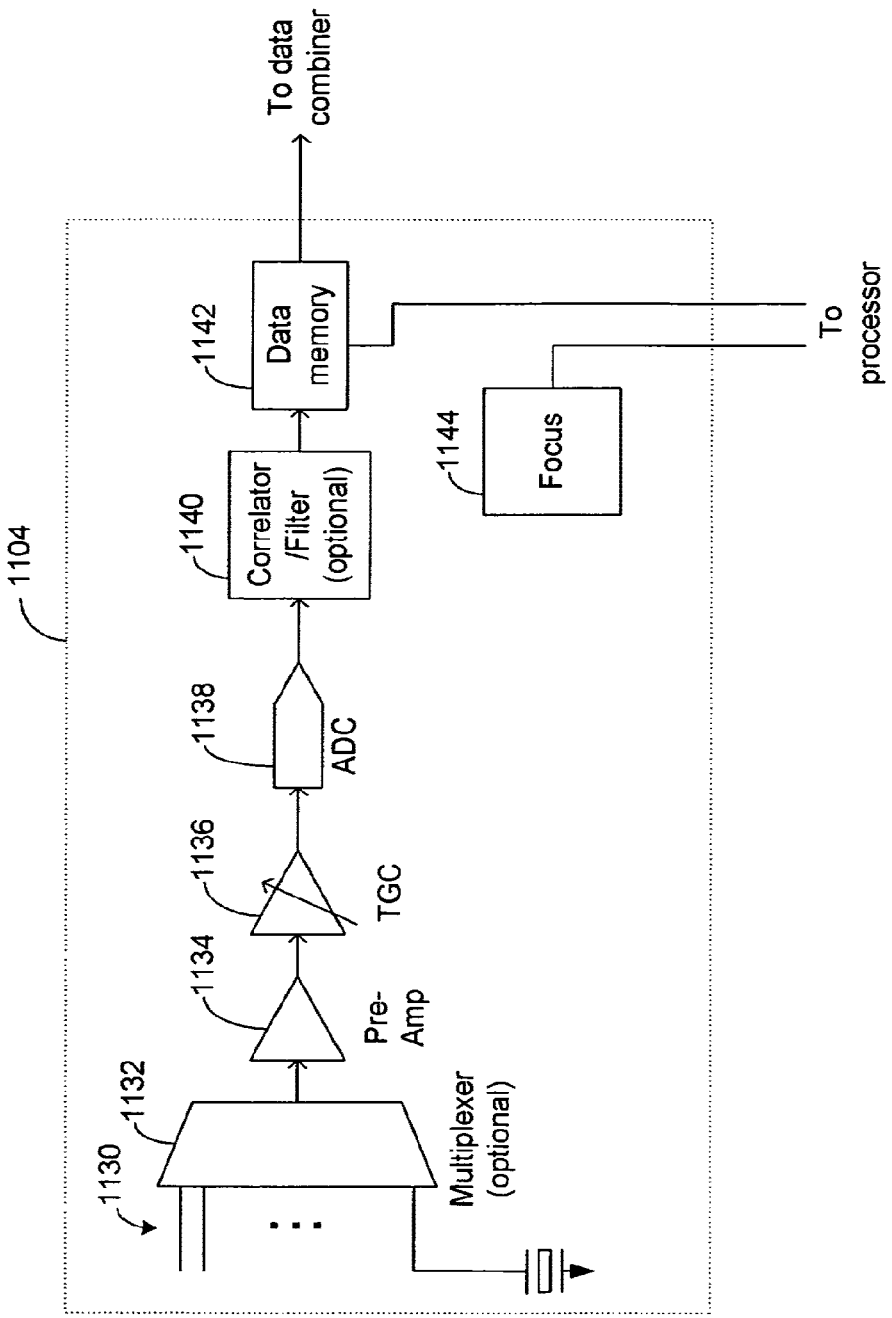

FIG. 35B now shows one embodiment of each of the data channel 1104 described above in reference to FIG. 35A. The data channel 1104 is shown to include an optional multiplexer 1132 that receives as inputs 1130 analog data traces from a plurality of receivers (not shown). In one embodiment, the multiplexer is not used, and data trace from one receiver is input into one data channel.

As shown in FIG. 35B, the multiplexer output (or signal from the receiver) can be amplified by a pre-amp 1134 and have its temporal gain corrected by a TGC 1136. The output from the TGC 1136 is shown to be digitally sampled by an ADC 1138 (analog-digital converter). In one embodiment, the ADC 1138 is a 12- or 16-bit amplitude ADC that samples the amplitude of the data trace at a sampling frequency.

As shown in FIG. 35B, the output from the ADC 1140 can be cleaned up and/or formatted for subsequent processing by an optional correlator/filter 1140. The output from the correlator/filter 1140 is input into a data memory 1142 for combining with the focus information from a focus database 1144 as described above in reference to FIG. 35A. The output from the data memory 1142 is then sent to the data combiner (1106 in FIG. 35A).

One can see that foregoing example signal and data processing, such as combining of different pages of data to determine the best scanline for a given receiver, can involve a substantially large amount of computation. Timely computation of such a task can be achieved, in one embodiment, by parallel processing.

One can also reduce the amount of computation in combining of data by limiting the combinations to a selected window in time. For example, suppose each digital echo data has N samples so as to represent a sampling duration of T. As described above, one way to form an image of a scanline is to focus onto a layer that intersects with the scanline. Such a layer with a given thickness is positioned from the receiver in a known manner. Thus one can estimate the approximate time values associated with the layer based on its relative position and its thickness by knowing the average propagation velocity of the echo signal in the medium. So to image the scanline for that layer, one can limit the digital echo data to a range that corresponds to the layer thickness.

Figure 36A:
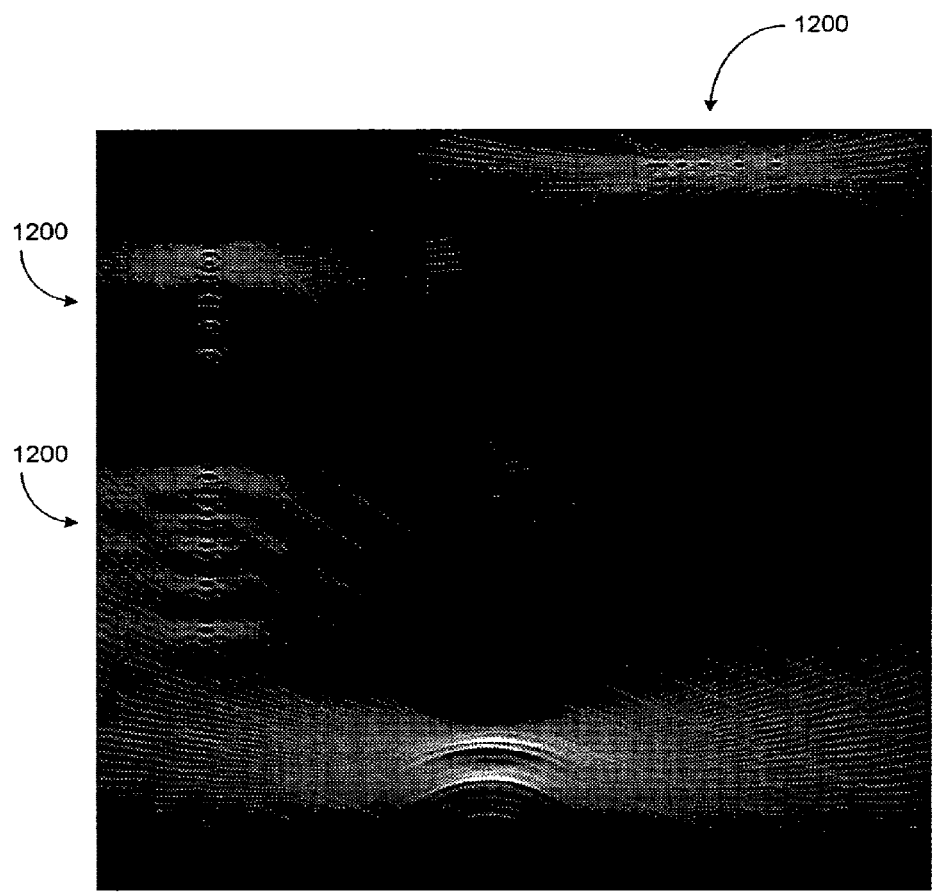
FIG. 36A shows a photograph of an example of an actual image obtained using multiple receivers and combining signals therefrom in a manner described herein.
Figure 36B:
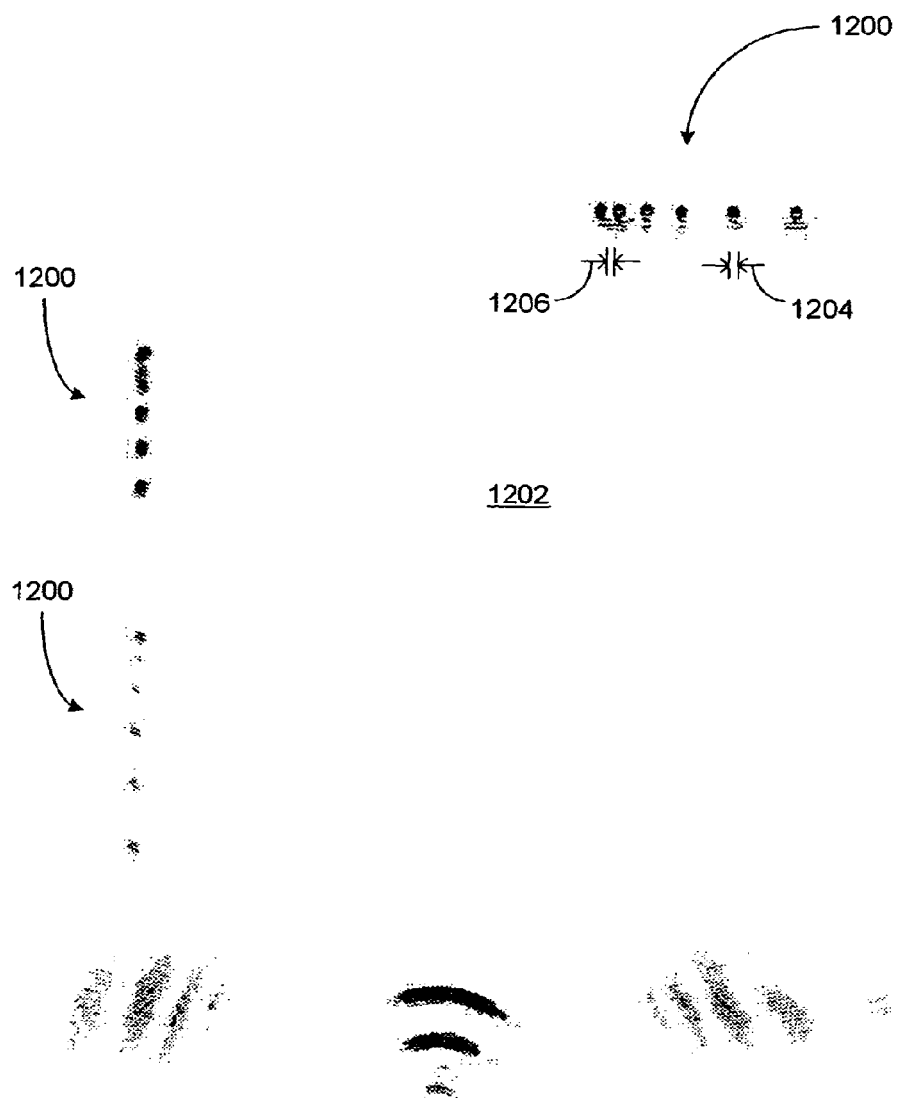
FIG. 36B shows a negative image of the photograph of FIG. 36A.

FIGS. 36A and B now show an example image obtained using some of the imaging methods described herein. FIG. 36A shows a black-and-white photograph of the image. FIG. 36B shows a negative image of the photograph of FIG. 36A. A sectional view of a plurality of wires 1200 is formed by imaging a slice through a medium 1202 where the wires are located. Each wire has a diameter (denoted as 1204) of approximately 100 micrometers, and a spacing (denoted as 1206) between (edge-to-edge) two closest adjacent wires is approximately 100 micrometers. The medium 1202 is water contained in a volume of approximately 350 cm$^3$, and the wires are located approximately 6.7 cm from an array of receivers (not shown).

To obtain such an image, 32 receivers were used to receive echo signals that resulted from sequenced transmission energy from 32 transmitters. The transmission energy was transmitted at approximately 3.5 MHz, and the echo signals detected by the receivers were sampled at a rate of approximately 20 MHz.

One can readily see from FIGS. 36A and B that the resulting high quality and contrast image displays a spatial resolution that appears to be better than 100 micrometers. For the example transmitted 3.5 MHz signal, a corresponding wavelength in water is approximately 440 micrometers (for an average velocity of 1540 m/s). Thus, one can see that resolving of a 100 micrometers feature at the transmitted energy frequency of 3.5 MHz is equivalent to a resolution being better than quarter of the operating wavelength.

In terms of Nyquist sampling criteria, the example 3.5 MHz signal would require sampling at a rate of approximately 7 MHz (twice the signal frequency) or higher for conventional devices. In a similar token, measurement of an example feature size of 100 micrometers would require a sampling rate of approximately 30.8 MHz (twice the frequency that can be assigned to a 100-micrometer feature size—i.e., 1540 [m/s]/100 [micrometers]=15.4 MHz) for conventional devices. Thus, one can see that sampling at multiple receivers and combining data therefrom can yield a high-quality result even if the sampling rate (example, 20 MHz) is less than the conventional Nyquist limit (example, 30.8 MHz).

From the description of the example image and the methods used herein, it is apparent that one can obtain a spatial resolution that is less than the wavelength associated with an operating transmission energy. Intrinsic resolution of a detector is often expressed in terms of $\lambda/D$, a ratio of the operating wavelength $\lambda$, and the effective aperture size D of the detector. A constant factor associated with such a ratio can vary depending on the configuration of a particular detector. For the purpose of description herein, it will be assumed that the intrinsic angular resolution is represented as $\theta=\lambda/D$.

One can reduce the value of $\theta$ (i.e., increase of "better" the resolution) by either reducing the wavelength and/or increasing the detector size D. The effective size D of the detector can be increased either by increasing the individual detector size, or by forming an array whose overall size can be substantially larger than that of each detector. Such methods have been used in some fields. In the field of ultrasound imaging, Applicant believes that currently, the image quality and resolution as disclosed herein has not been achieved using conventional systems and methods. For example, one embodiment of the imaging system and method yields an angular resolution that is equivalent to using a wavelength that is less than a quarter of the operating wavelength for a given detector size D. That is, the resolution is better than $\theta=(0.25)\lambda/D$ in one embodiment.

From the description herein it is also apparent that the sampling frequency can be less than the frequencies associated with perturbation features that "ride" on the "carrier-wave" echo of the transmission energy. One way to characterize such performance is by way of Nyquist criteria that essentially states that a signal needs to be sampled at a frequency F that is at least twice the frequency of the signal to obtain any useful information. Thus for example, if a signal has a frequency of 1 MHz, it needs to be sampled at 2 MHz or higher.

If the sampling frequency is less than twice the signal frequency, an effect known as "aliasing" occurs, where frequencies above the Nyquist frequency (F/2) "fold over" to behave like lower frequencies. As is known, aliased frequency f in the range F/2 to F becomes f that can be expressed as $|f-F|$.

From the description herein, it is apparent that in one embodiment (that produces the example image of FIGS. 36A and B, for example), the sampling frequency can be less than twice the frequency associated with the size feature of interest. For example, the feature size of the wires in FIGS. 36A and B is approximately 100 micrometers, and its corresponding "frequency" can be represented as approximately (1540 m/s)/(100 micrometers)=15.4 MHz. From the results obtained by sampling at approximately 20 MHz (which is less than twice the frequency corresponding to the feature size), one can see that such relatively small perturbation features can be imaged with excellent quality and resolution.

It should be noted that for the purpose of description, the term "frequency" means the frequency associated with the central peak associated with the signal. Thus, if the signal is a sinusoidal wave, its frequency corresponds to the standard meaning. If the signal is a pulse (e.g., Gaussian shaped), then the frequency corresponds to the central peak of the pulse. If the signal is a perturbation feature having a peak structure, then the frequency corresponds to that peak.

With such example definition of frequency, one can characterize the performance of the present teachings as being able to image an echo signal in terms of spectral frequency components. If a given echo signal has a maximum intensity value, then the resolvable spectral frequency components above the Nyquist frequency of F/2 can include higher frequency components having intensities that are above a predetermined value. Such a predetermined value can be set at different values, such as 50 dB, 40 dB, 30 dB, 20 dB, 10 dB, or 10 dB less than the maximum intensity value the echo signals.

FIGS. 37-42 show an example of an operating principle that could explain why the various techniques of the present disclosure can yield relatively high resolution images (for example, images shown in FIGS. 36A and 36B). FIG. 37 shows an example detectable analog signal 1302 having various fine features. Some of the fine features are noise, and some may be signal(s) of interest that result from interaction of the acoustic energy with one or more objects in the medium. In general, whether a given feature is noise or signal of interest is not known in advance. For the purpose of description, however, a feature 1306 will be assumed to be a signal feature of interest, and the rest of the features on the example signal 1302 will be assumed to be noise. Also, for the purpose of providing a visual reference, an example carrier signal 1304 is superimposed with the signal 1302. Essentially, the signal 1302 includes the carrier signal combined with the various signal features, including the noise and the example signal feature of interest 1306.

As further shown in FIG. 37, the analog signal 1302 is shown to be sampled periodically at example times t1 to t8. Solid dots at the intersections of the analog signal 1302 and the sampling times indicate the signal values at the sampling times.

FIG. 38 shows an example table of data 1310 that can be obtained from sampling of the analog signal at times t1 to t8. The first column represents the sampling time; the second column represents the signal value S; and the third column represents the digitized value D or the signal value S. Thus, for example, S5 represents the value of the signal 1302 at time t5, and D5 represents the digitized value obtained from sampling of the signal value S5.

In many applications, the signal values (for example, analog measurement values) are not obtained. Instead, the analog signal 1302 is digitally sampled at the sampling times.

FIG. 39 shows a plot 1320 of the example digitally sampled values (D1 to D8) at the sampling times t1 to t8. As one can see, it can be a challenge to be able to reconstruct the original detectable analog signal 1302 from the sample set 1302 of digitally sampled data. In fact, there can be introduction of ambiguities that may or may not be resolved.

Such challenges are faced routinely in the known field of digital signal processing. In general, a signal having a frequency $f_o$ is not reconstructable, without ambiguity, from digitally sampled data if the sampling frequency f is less than twice the signal frequency $f_o$. If a signal contains various frequency components in a bandwidth B, then that signal is considered to be not reconstructable, without ambiguity, from digitally sampled data is the sampling frequency $f_s$ is less than twice the bandwidth B. Such a constraint generally imposes a minimum sampling frequency of $2f_o$ (or 2B) commonly referred to as a Nyquist frequency. An ambiguity that results from sampling at a frequency below the Nyquist frequency is generally referred to as "aliasing."

It is, however, possible to obtain a useful result even when the sampling frequency is less than the Nyquist frequency. In digital signal processing, sampling of bandpass signals is one example known situation where a sub-Nyquist sampling frequency can yield useful results. For example, aliasing can be avoided when the sampling frequency $f_s$ is in the range defined by $$\frac{2f_cB}{m} \geq f_s \geq \frac{2f_cB}{m+}$$

where m is a positive integer, $f_c$ is the center frequency of the signal, $f_s$ is the sampling frequency, and B is the bandwidth of the bandpass signal. In one example where $f_c$=20 MHz, and B=5 MHz, the above aliasing-avoidance condition can be satisfied if $f_s$=22.5, 17.5, or 11.25 MHz for m=1, 2, or 3. These example sampling frequencies are below the commonly-known "Nyquist frequency" of $2f_c$ (=40 MHz in this example); however, they are all above the Nyquist frequency defined in terms of the bandwidth (2B=10 MHz). Additional details about sub-Nyquist sampling and related topics can be found in commonly available textbooks such as "Understanding Digital Signal Processing," Richard G. Lyons, Prentice Hall PTR Publication.

However one defines what sub-Nyquist frequency is, resulting frequency spectrums of the sampling that avoided aliasing (for example, by sampling bandpass signals under certain conditions) have various gaps where frequency components do not exist. Such gaps can be on either or both sides of the frequency $f_s/2$ (that is, half of the sampling frequency) in the frequency space distribution. In some applications, such gaps, and even the use of bandpass signals to avoid aliasing, may be undesirable for various reasons.

As described herein, one or more embodiments of the present disclosure do not necessarily suffer from the constraints associated with techniques such as a bandpass filtering technique. As described above in reference to FIGS. 37-39, the sampled data, whether in the raw form S or the digitized form D, represent the values of the signal 1302 at the sampling times. There is, in general, no ambiguity with respect to the validity of such sampled data. It is known that an i-th data $D_i$ represents the value of the signal 1302 at time $t_i$. Given the data $D_i$, it is possible to reconstruct the portion of the signal 1302 at time $t_i$. As described above, ambiguities can arise when one attempts to reconstruct the entire signal 1302 from a group of such discrete data (for example, the digital data set 1320 of FIG. 39).

It should be understood that the example signal 1302 and the resulting example discrete data set 1320 are associated with a given detector. Thus, if a given system only has one detector, then the signal reconstructing capability is essentially constrained by the sampling frequency and other conventional digital signal processing parameters.

Figure 40:
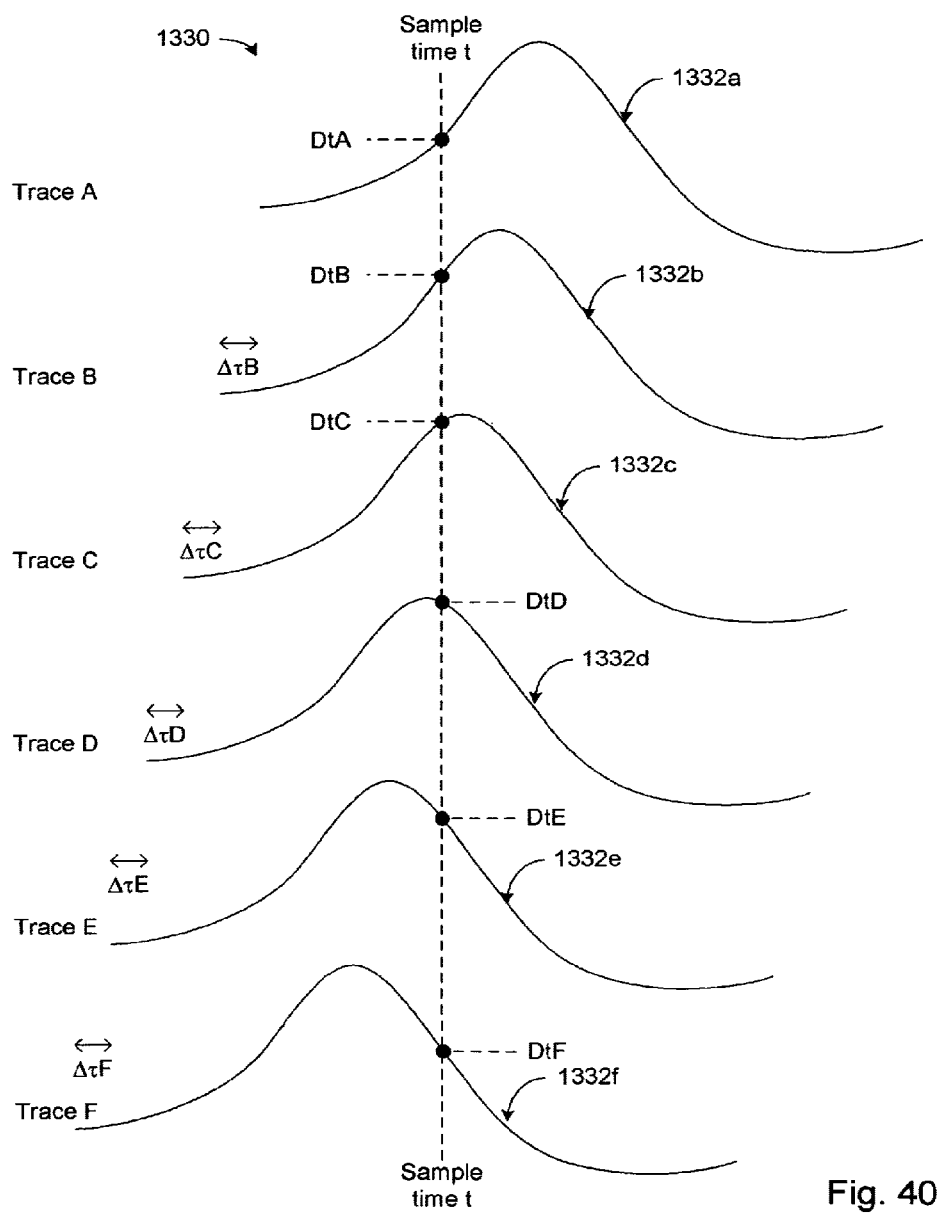
FIG. 40 shows an example relatively fine feature of the analog signal of FIG. 37 being sampled at different phases via various example detectors.

In one or more embodiments of the present disclosure, however, use of a plurality of detectors can allow improved characterization of a signal feature of interest without being constrained by aliasing concerns. FIG. 40 shows an example of a plurality of signal traces 1330 that can be obtained by use of a plurality of detectors. For the purpose of description, it will be understood that trace A is from detector A, and so on. Also for the purpose of description, only the signal feature of interest 1332 is depicted. In general, the signal feature of interest 1332 may vary when detected at different detectors. For example, the amplitude may decrease if the propagation distance increases. Also, the medium may vary for propagation paths to different detectors.

As further shown in FIG. 40, each of the example detectors A to F are shown to be sampled at time t. Thus, trace A from detector A yields a sampled value of DtA, trace B from detector B yields a sampled value of DtB, and so on.

As further shown in FIG. 40, the signals 1332 are shown to arrive at the detectors in succession. For example, the signal 1332b is shown to arrive at detector B after a delay of $\Delta\tau B$ from the arrival time of the signal 1332a at detector A. The signal 1332c is shown to arrive at detector C after a delay of $\Delta\tau C$ from the arrival time of the signal 1332b at detector B, and so on. Such delays in arrival times may result from the geometry of the arrangement of the detectors.

As described herein, there is in general no ambiguity in the sampled data themselves. Thus, the sampled data DtA unambiguously represents the signal 1332a at time t. Similarly, the sampled data DtB unambiguously represents the signal 1332b at time t, and so on. One can thus see that the independently obtained data via different detectors unambiguously represent the signal 1332 at different phases of that signal 1332. If such signals are phase shifted and combined properly, the resulting sampled data representing the different phases can be essentially equivalent to sampling the signal at a higher frequency.

One or more embodiments of the present disclosure relate to combining a plurality of signal traces from a plurality of detectors so as to allow imaging of relatively fine features in a medium. For example, one embodiment of a method for combining digitally sampled data has been described above in reference to FIGS. 22 to 30.

Figure 41:
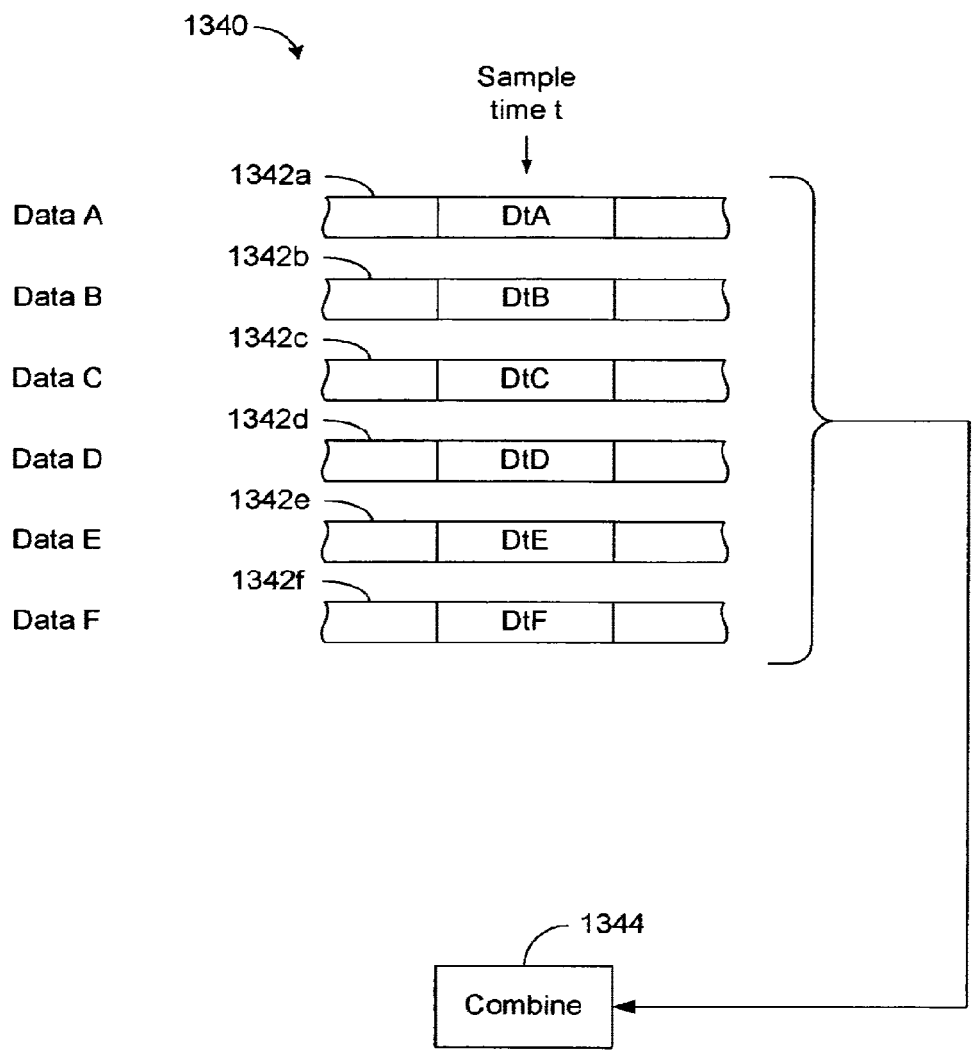
FIG. 41 shows an example of digitally sampled data corresponding to the example samplings via the example detectors.

In one embodiment, a similar combining technique 1340 may be applied to the example sampled data associated with the example traces A to F of FIG. 40. Thus, as shown in FIG. 41, a plurality of digital data sets A to F containing portions (DtA, DtB, etc.) are shown to be combined in a similar manner via a component 1344. As describe above, such combining can yield an enhancement of the signal of interest while the noise components cancel substantially.

Figure 42:
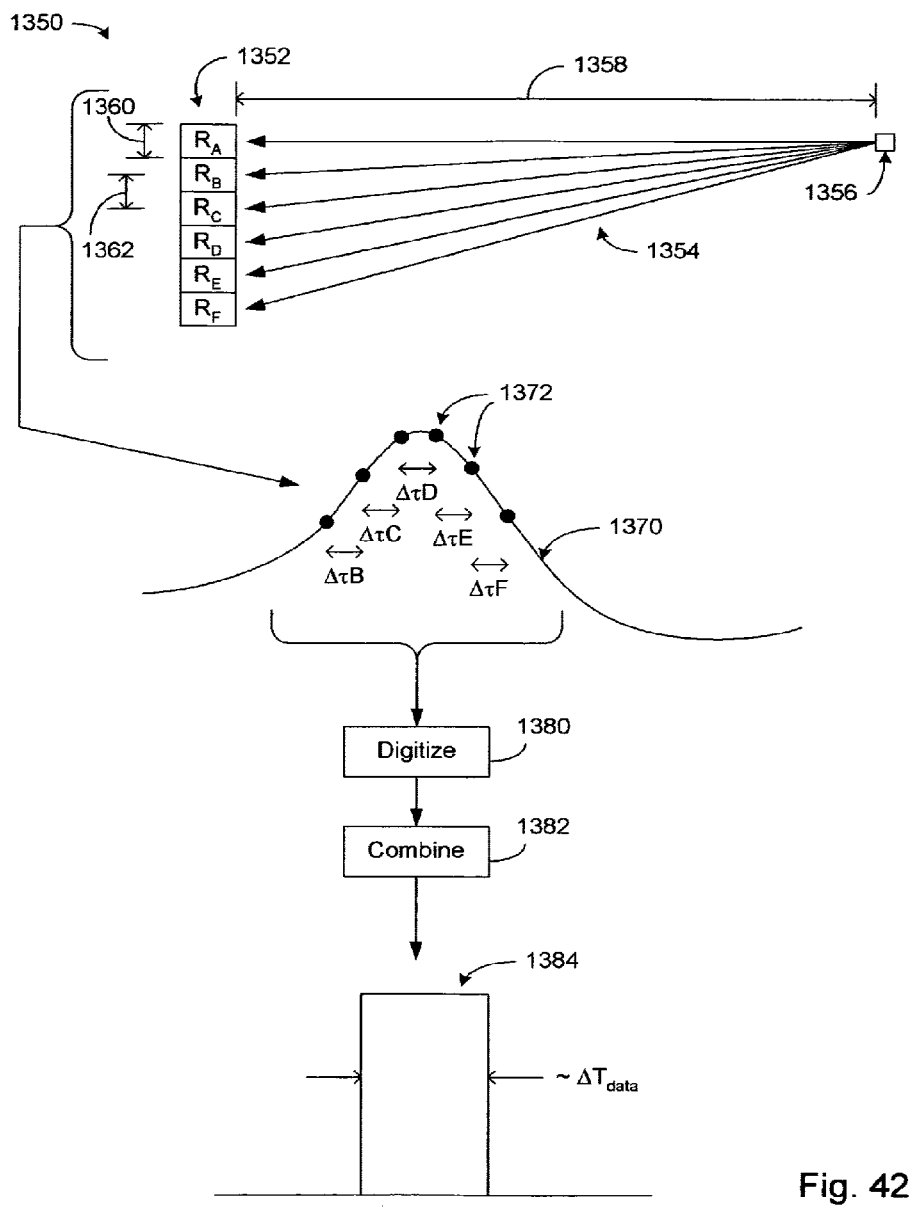
FIG. 42 shows how various parameters related to detection configuration and sampling configuration can determine an effective sampling frequency facilitated by phase-shifted samplings via a plurality of detectors.

FIG. 42 now shows an overview 1350 of the example process described above in reference to FIGS. 40 and 41. In one embodiment, the above-described delays in arrivals of signals 1354 can be facilitated by an orientation of an array of detectors 1352 with respect to a reflecting object 1356. In the example shown, the array 1352 is oriented so a line between the object 1356 and detector A is generally perpendicular to the array 1352. Thus, detector A is closest to the object 1356 in the example of FIG. 42. Distances from the object 1356 to detectors B to F are successively greater.

As further shown in FIG. 42, the differences in pathlengths to the different detectors can depend on factors such as distance 1358 from the array 1352 to the object 1356 and detector spacing 1362. The detector spacing can depend on the detector dimension (for example, when the detectors are closely packed).

As further shown in FIG. 42, the sampling of offset signal traces can yield a plurality of sampled values 1372 that can be equivalent to sampling of a signal 1370 at intervals determined by the arrival offsets (for example, due to pathlength differences). As described herein, one generally does not know that the sampled values belong to the same signal 1370. As also described herein, the sampled data 1372 can be digitized in a component 1380, and the digitized data can be combined in a component 1382 so as to yield a combined data 1384.

As further shown in FIG. 42, such combination of the digitized data can match data "packets" that correspond a given feature of interest. In one embodiment, a given data packet for a given signal trace can represent a sampling period. Thus, combining a plurality of such data packets can yield a combined packet representative of an average sampling period (that is, inverse of the sampling frequency) $\Delta T_{data}$.

Based on the foregoing, one can see that the resolution associated with the combined digital data can have a time resolution that depends on the sampling period. One can also see that the number of sampled data that can be combined into a given sampling period can depend on how phase separated the signal traces are at the detectors. As described above in reference to FIG. 42, phase separations can be affected by factors such as differences in the pathlengths to different detectors. One can also see that the quality and/or efficiency of the combined digital data can be affected by the number of detectors and/or the actual sampling interval. While a larger number of detectors and a smaller actual sampling interval may be desirable, one may need to balance such benefit with detector-imposed geometries and/or computing requirements.

As described herein, introduction of phase differences to a plurality of independent detectors, and independently sampling at those different phases can be generally equivalent to sampling a single signal at an effective sampling interval corresponding to the phase differences. The effective sampling interval can be affected (and sometimes selected) by factors such a detector geometry with respect to a given reflecting object, medium, and/or the actual sampling frequency. These factors are introduced by independent sampling by a plurality of detectors, and are generally not constrained by the aliasing effect associated with sampling of a single signal.

Furthermore, the overall sampling resolution of the combined digital data can be selected based on the effective sampling interval and the number of detectors to combine, both of which can affect how many sampled digital data get combined into a given combined packet.

When one considers the foregoing, it is apparent that the overall sampling resolution and the corresponding spatial resolution depend on factors that are generally not affected by aliasing. Consequently, it is believed that the present disclosure allows sampling of analog echo signals having substantial frequency components (for example, noise and/or features of interest) in essentially any range. In one embodiment, such a range includes frequency components from (and including) zero to F/2, where F is the actual sampling frequency for sampling of the analog echo signal; and from (and including) F/2 and higher. Such sampling can produce corresponding digital echo signals, and such digital signals can be combined so as to yield an image having a relatively high resolution.

In one embodiment, the foregoing examples of combining sampled analog echo signals can be considered as substantially negating the effects of aliasing within at least the sampled analog echo signals. That is, without such combining of the sampled analog echo signals, reconstruction of analog signals would be subject to aliasing effects, and thus be subject to constraints of certain range(s) of sampling frequency(ies).

Figure 43:
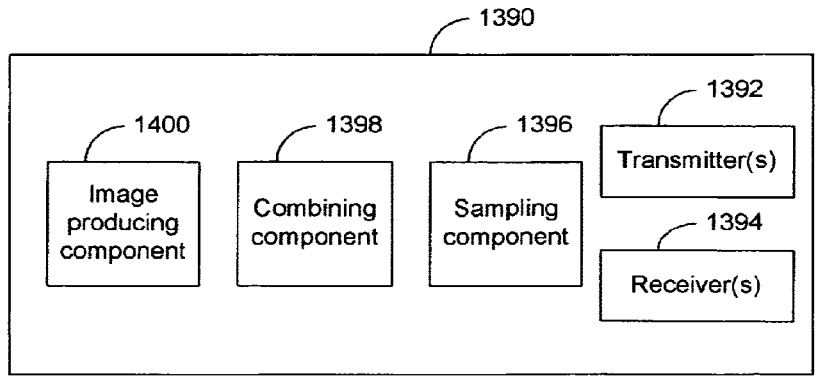
FIG. 43 shows a block diagram of one embodiment of an apparatus having a sampling component and a combining component that allows detection and imaging of analog echo signals resulting from relatively fine features in a medium.

FIG. 43 shows that in one embodiment, various techniques that facilitate production of relatively high resolution images can be implemented in a system 1390 having different components or modules. For example, the system 1390 can have a transmitter component 1392, a receiver component 1394, a sampling component 1396, a combining component 1398, and/or an image producing component 1400. Each, some, or all of these example components or modules may represent a physical device, a process, or any combination thereof. Moreover, a given component or a module can represent one or more devices, one or more processes, or any combination thereof, such that the given component achieves or facilitates a given functionality of the system 1390.

For example, the sampling component or module 1396 can include one or more devices, one or more processes, or any combination thereof, such that the component 1396 facilitates digital sampling of one or more analog echo signals. In one embodiment, the sampling component 1396 includes an analog-to-digital converter (ADC). In one embodiment, a plurality of ADCs can be associated with respective plurality of analog echo signals from a plurality of receivers. In one embodiment, the sampling component or module 1396 may provide a functionality of digital sampling of a plurality of analog echo signals. In one embodiment, the sampling component 1396 includes a processor. In some embodiments, the sampling component 1396 can include devices or components such as, but not limited to, one or more computers, one or more of various types of filters that facilitate processing of signals, one or more ADCs, and/or one or more devices such as sigma-delta converters.

Similarly, the combining component or module 1398 can include one or more devices, one or more processes, or any combination thereof, such that the component 1398 facilitates combining of a plurality of digital echo signals. In one embodiment, the combining component 1398 includes processor.

Figure 44A:
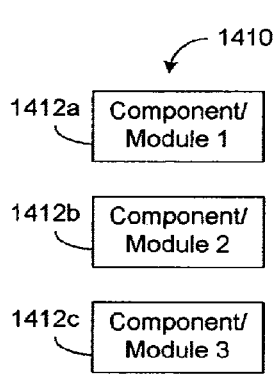
FIGS. 44A-44C show by examples various ways modules or components can be configured in various embodiments of the present teachings.
Figure 44B:
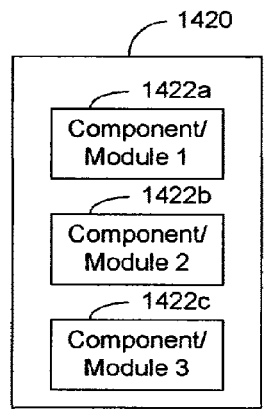
Figure 44C:
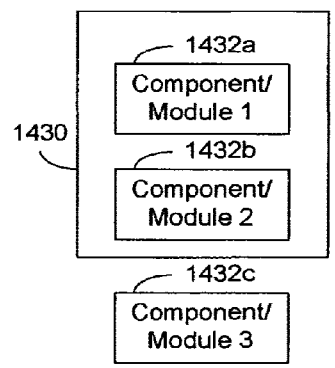

In general, as shown in FIGS. 44A-44C, modules or components described herein can be separate units and/or processes, be part of a same unit and/or process, or any combination thereof. For example, as shown in FIG. 44A, example modules 1410 are depicted as including separate modules 1412a-c, where each module can be configured to perform certain function(s) so as to achieve a desired functionality overall. As shown in FIG. 44B, an example modules 1422a-c are depicted as being parts of a unit or process 1420, such that the unit or process 1420 can be configured to perform different functions via the example modules 1422a-c so as to achieve a desired functionality overall. As shown in FIG. 44C, an example modules 1432a and b are depicted as being parts of a unit or process 1430, such that the unit or process 1430 can be configured to perform different functions via the example modules 1332a and b. The functionality of the unit or process 1430 can be combined with a functionality of a separate example module 1432c, so as to achieve a desired functionality overall.

Figure 45A:
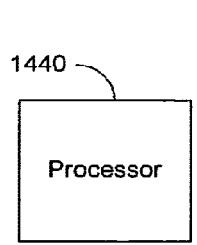
FIGS. 45A and 45B show by examples various ways a processor can be configured in various embodiments of the present teachings.
Figure 45B:
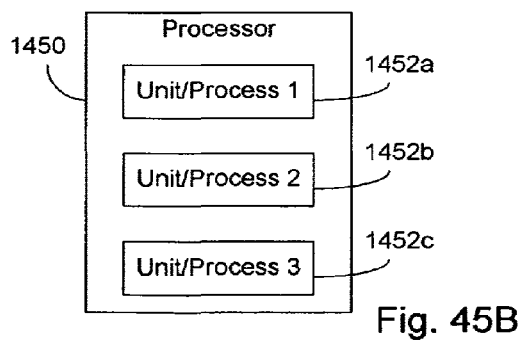

FIGS. 45A and 45B show how such different example configurations can be applied to processors that are configured to facilitate various processes as described herein. In some embodiments, as shown in FIG. 45A, a processor 1440 can be configured to perform or facilitate performance of one or more processes. In one embodiment, the example processor 1440 can be incorporated into a single unit.

In some embodiments, as shown in FIG. 45B, a processor 1450 may include a plurality of units 1452 that are configured to provide certain functionalities, such that some combination of such individual functionalities provides one or more functionalities of the processor 1450. In one embodiment, the example processor 1450 includes a plurality of separate units.

In some embodiments, the example configurations of FIGS. 45A and 45B can be combined in any manner. For example, a processor functionality may be provided by one or more first processors that are similar to that described above in reference to FIG. 45A, and one or more second processors that are similar to that described above in reference to FIG. 45B.

Any of the foregoing techniques, either individually or in any combination, may be used for medical or non-medical purpose. Moreover, in some embodiments, various means for providing various functionalities described herein can be achieved by various modules or components also described herein. For example, FIGS. 43-45 show various examples of modules or components that can be configured to perform various techniques of the present disclosure.

Figure 46:
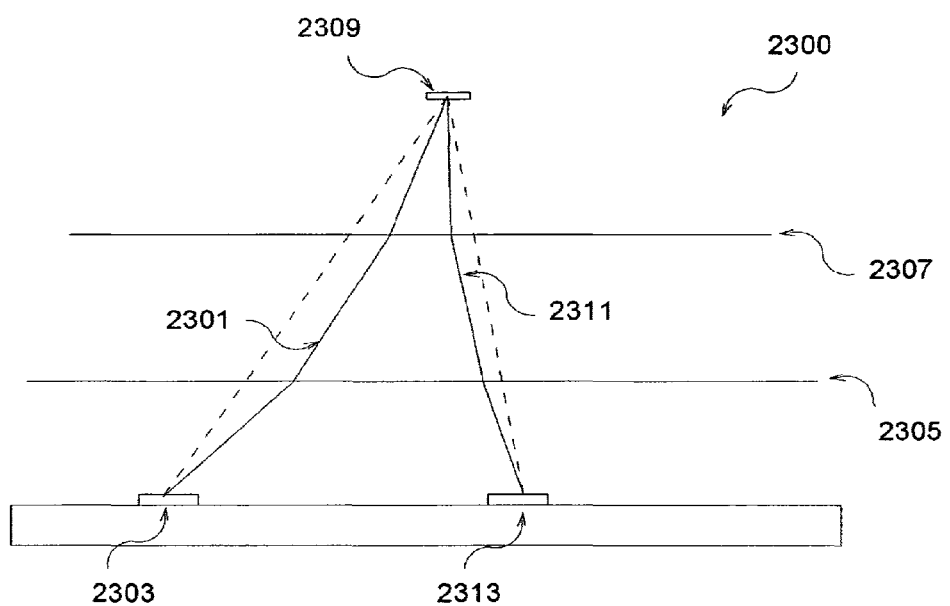
FIGS. 46 and 47 show examples of how focus of an object in a tissue can be achieved by adjusting various parameters that affect travel times of acoustic energy.
Figure 47:
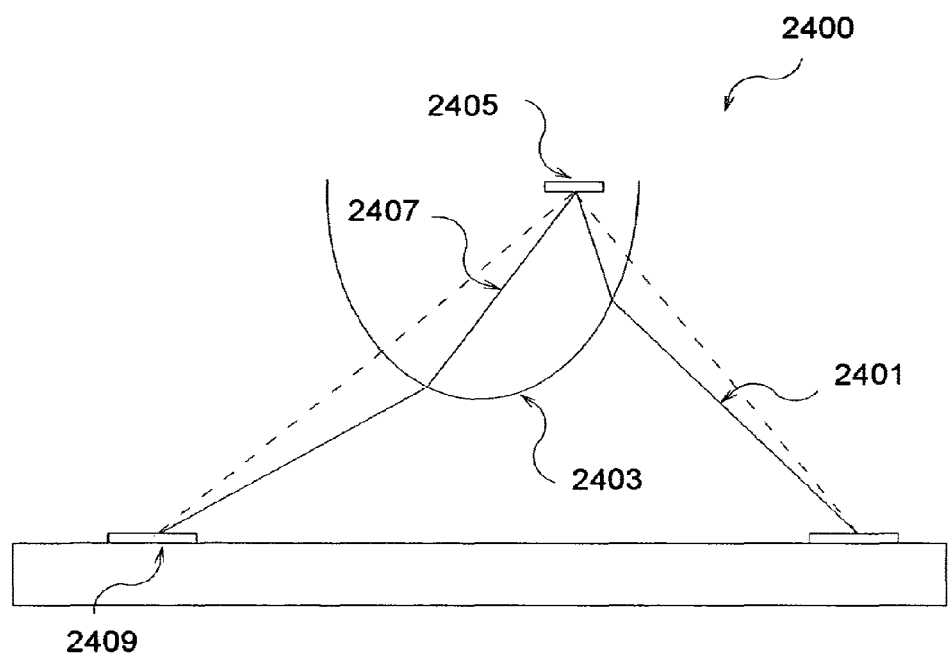

Some embodiments of the present disclosure relate to combinations and/or variations of some of the features described above in reference to FIGS. 1-45. FIG. 46 shows an example imaging situation where an acoustic energy traverses a plurality of layer interfaces between a given transmitter and a voxel and/or between the voxel and a given receiver. In some situations, one of such layers can be a coupling medium between the transmitter/receiver array and the skin of a tissue being imaged. The tissue can have one or more layers (between the skin and the voxel) where acoustic energy propagates at different speeds. It will be understood that a "layer" is not limited to a planar volume as depicted in FIG. 46, and can include any volume having an interface. FIG. 47 shows an example imaging situation where a tissue volume has a curvature. Human breast is a non-limiting example of such a tissue volume.

In one embodiment, the calculation of propagation time described above may be made by assuming a physical arrangement of tissues and speeds of sound and then calculating wave travel times along the straight line paths between the transducer elements and the voxel of interest. In another embodiment, refraction may be taken into account. For an assumed physical arrangement of tissues with substantially clear boundaries between substantially homogeneous media with different but constant speeds of sound, it is possible to establish a ray from each transducer element to each voxel, where the ray bends at each interface between two media according to the well known Snell's law as the sound traverses it. While the sound wave front from any transmitter, or reflected from any scatterer, propagates outward as a spheroidal wave front, the sound traveling on a path between any two points may be thought of as a ray. These envisioned sound rays will propagate through each of these layers on their way from each transmitter to the point of interest, and the sound rays will further propagate through the successive layers on their way to any specified receiver. More specifically, the bending of the ray at the interface can be calculated by making the quantity (n)sin(theta) invariant across a boundary where n is refractive index indicative of the speed of sound and theta is the direction of the ray relative to a normal vector through the surface. Once the correct ray and the velocities of the media have been determined the travel time index for that ray may be calculated.

Refraction can be particularly important in this type of ultrasound imaging. In conventional ultrasound every point in the tissue is insonified with a relatively closely spaced group of transducer elements and thus the difference in angle of the incident rays relative to any given interface is relatively small.

If significant refraction takes place an object of interest behind the interface will be displaced but only slightly defocused. In one embodiment of the present disclosure, some parts of the tissue of interest are insonified by every transducer in an array with incident rays over a much larger range of angles. Differences in refraction in the rays relative to each other are thus much more significant. Compensating for this refraction in the display can substantially improve the focus and contrast of the image.

An assumed geometry need not be limited to homogeneous media but may in fact have speed of sound gradients. The bending of the sound rays in a gradient medium can still be estimated by Snell's law.

This method of calculating bent rays can be applied satisfactorily in a two dimensional image plane. A more general case of three dimensions can also be used in which the rays can bend in space. In this case the pixels are more properly considered as 3-dimensional voxels'.

In one embodiment where improved image quality desired, it is possible to use a priori knowledge of anatomy to specify an algorithm for picking the preferred travel time index.

The various parameters in the assumed configuration (such as layer thicknesses and speeds of sound) may be varied and optimized under operator and/or algorithmic control to improve the focus. Various measures of success could be used to assess the relative improvement of one set of parameters relative to another. One measure of success might be contrast for example. Higher contrast in intensity over a given range of pixels implies better focus. A measure of this higher contrast might, for example, be a calculated standard deviation of the brightness of a selected region containing a bright area or areas and dark area or areas. An increase in standard deviation implies improved focus. Another method might be to maximize the intensity relative to the dimensional extent of a brightness peak associated with a point reflector or a boundary. Other methods of greater or lesser sophistication may also be used to judge the quality of the focus and to provide feedback to the optimization process.

FIG. 46 shows an example configuration 2300 having three parallel layers of matter of different assumed sound speeds. In this example a transmitter 2303 sends an essentially spherical wave front of sound waves. A particular portion of this wave front, depicted as a ray 2301, departs the transmitter 2303 and is bent at interfaces 2305 and 2307 on its way to a pixel 2309. A reflecting or scattering object located at pixel position 2309 may reflect this ray specularly, or it may break it up into another spherical wave front of backscattered sound waves. In either case, a specific ray 2311 being considered as leaving the pixel 2309 is bent similarly by interfaces 2307 and 2305 on its way to a receiver 2313.

In order to improve the focus of the pixel 2309, adjustments may be made in a number of ways. In one method, the focus of the first layer boundary (2305 in FIG. 46) may be improved by adjusting the speed of sound in the first layer encountered until the layer's focus is optimised. The next layer boundary (2307 in FIG. 46) can be focused similarly, using the above-obtained speed value for the first layer. Subsequent layer boundary(ies) (if any) can also be focused similarly in a successive manner.

For a specific example of such layering, when using the described ultrasound system to observe the human liver, there are distinct sequential layers of fat, muscle and other known tissue, of known sound speed, and of roughly known thicknesses and orientation to exist in a typical human body. By proposing such a layered configuration, the variable parameters of, for example, fat thickness may be varied to improve the focus. The resulting improved sound speed times for different paths may be stored in, for example, the time index table to be used in assembling the display.

The liver is a good example of where an a priori model of layers can be used. In this case the fat layer is well known as a source of focusing errors in ultrasound, resulting in a large proportion of patients to be unsatisfactorily imaged. Since the tissues and their order are known only the thicknesses need to be determined through a series of steps. In a simplified case where only a layer of fat and a layer of liver are considered, the thickness of the fat layer may be determined by reconstructing the image while using a speed of sound (in fat) assumption. Once the surface of the liver has been found then a new speed for liver may be used beyond this interface and refractions may be calculated in order to obtain improved travel time indices for pixels within the liver.

There is no need for the layers to be flat as long as there is enough information on the interface configuration in order to allow refraction to be calculated.

If there are layers present then the layer thicknesses and speeds may be determined in a sequence starting with the closest layer to the transducer using the focus criteria described above. The standard deviation of the intensities within the layer may be maximized for example. Or the contrast in the region of the furthest interface may be maximized. More specifically a first interface may be found which defines the posterior surface of a first layer. The speed of sound in this layer may then be varied in order to optimize the focus of the posterior surface interface for example, or to optimize the focus of point scatterers within the layer. Once the first layer is determined then a speed of sound may be postulated for the next layer and refracted rays can be calculated. This process may be repeated as required.

By way of a further non-limiting example, the geometrical configuration proposed may be of curved shape, such as an ellipsoid shape, which may contain matter of different sound speed from the surrounding media. This ellipsoid may further have other structures within it. It will again be seen that via calculations and/or estimations that may be undertaken, the deviations of sound rays due to the intersection of the rays with such ellipsoid surfaces may be calculated for various assumptions of size, location and speed composition of said ellipsoid.

FIG. 47 shows such an configuration 2400 in greater detail. A refracted ray 2401 is bent by a sound speed interface 2403 on its way to a chosen pixel 2405, and a backscatter ray 2407 is in turn bent by a similar discontinuity on its way to a receiver 2409.

As an example, a human breast suspending in coupling medium may take on the appearance of an ellipsoid. In order to improve the focus of a breast ultrasound image it is possible to image the breast using a constant speed of sound corresponding to the coupling medium. The surface of the breast will be represented properly since the sound waves scattered by it have traveled only through the medium. The tissue within the breast will be somewhat defocused in this image due to the lack of refraction compensation. Using this first image the breast surface can be found either automatically by one or more known techniques, or by using some operator feedback. Once the surface of the breast has been found then the travel time indices can be calculated using refractive bending according to Snell's law. Then the image can be recalculated with more accuracy.

In another method, features may be extracted from an image formed using a constant speed assumption. These features such as interfaces may then be used to approximate geometry which can then in turn be used to generate presumed refractive indices for better imaging of the objects behind the interfaces with respect to the transducers.

For a specific example, when using the described ultrasound system to observe a human breast, it may be advantageous or necessary to suspend the breast in a vessel of water at a known temperature, thus providing a set-back view, and allowing a greater volume of the breast to be insonified during a single acquisition. In this illustrative example, the coupling medium, possibly water, in the vessel will have a known speed of sound. This speed of sound may be measured or taken from a published reference. An accurately placed image of the breast surface may then be formed in three dimensions using this single, known speed of sound. Using this accurately placed surface and an initial, assumed, speed of sound in the breast, rays from each voxel located within the breast may then be traced to each transmitter and each receiver in an ultrasound transducer array taking account of refraction through Snell's Law at the accurately known, curved surface. In one embodiment, tables of indices may then be created using these calculated values. An image of the breast and its constituent tissues may then be reconstructed using these tables of indices that provide information about corresponding propagation times. The focus of this image may then be improved by varying the speed of sound for the breast until an optimal focus is achieved. This limited example which treats the breast as a medium with a single, homogeneous speed of sound may be extended and further improved by the identification of other regions within the breast where the speed of sound may be varied.

In addition to finding layers, a similar but more general approach is possible in which regions of interest are detected by their boundaries. Examples include fat lobules or cysts within a breast. The boundary closest to the transducer may be generally imaged well while the far boundary is generally distorted by the refraction and sound speed change within the region of interest. By optimizing the focus within the region of interest (for example, by varying speed of sound) it is possible to correct the distortions and gain a better image of the region of interest as well as the posterior boundary and one or more regions behind it.

The optimization of the speed of sound may be achieved using many approaches. For example, a fixed set of values may be tried and the value giving the best focus selected. As another example, the value for speed of sound may be adjusted progressively until a peak in quality of focus is passed or until the quality of focus is within an acceptable tolerance.

It will be seen that it is possible to simplify the solution for the three dimensional problem to a two dimensional slice through the three dimensional data. This may be done to conserve computational resources. It is understood that using a two dimensional approximation for a three dimensional image (when captured with a two dimensional transducer) may be less accurate than the full three dimensional model since an incident ray within the 2D viewing plane may in fact be refracted out of the plane. Consequently, while there will be a useful improvement of focus following the above technique when limited to the two dimensional case, there will be situations in which the focus improvement will not be as good as for the three dimensional analysis.

For multiple layers, the progression of analysis can be performed using the same or similar approach as described elsewhere in this disclosure. Curved layers will be a generalized case of straight layers. For amorphous regions of differing sound speed, some insight into the location of the edges of those regions can be imaged in the same or similar approach as described above. Once these edges have been located, optimizations for refraction can be made using, for example, Snell's Law. In some cases, regions of different sound speed will be small enough that the difference in path can be ignored for the purposes of creating a sufficient image. In other cases, the difference in speed of sound and shape of the region will be sufficient to create significant ray bending that should be allowed for in the optimization.

As is generally known in the field, it is possible to simulate the emission of a single transducer element while increasing the sound pressure amplitude of the emitted wave. This can be accomplished by firing a sequence of transducer elements at controlled times such that the leading edges of their emission waves form a portion of a sphere with its center at the virtual point source. This technique is known as virtual point source. Thus, for the purpose of description herein, an emission by a single transducer element can mean an emission from a physical transducer element, or a virtual point source emission generated by a plurality of transducer elements.

Methods and apparatus as described herein may be applied in various contexts and in combination with other ultrasound methods and apparatus. The following sections describe a number of example ways in which the ultrasound technology as described herein may be applied.

Extended Applications of Spatial Offsets

Figure 48:
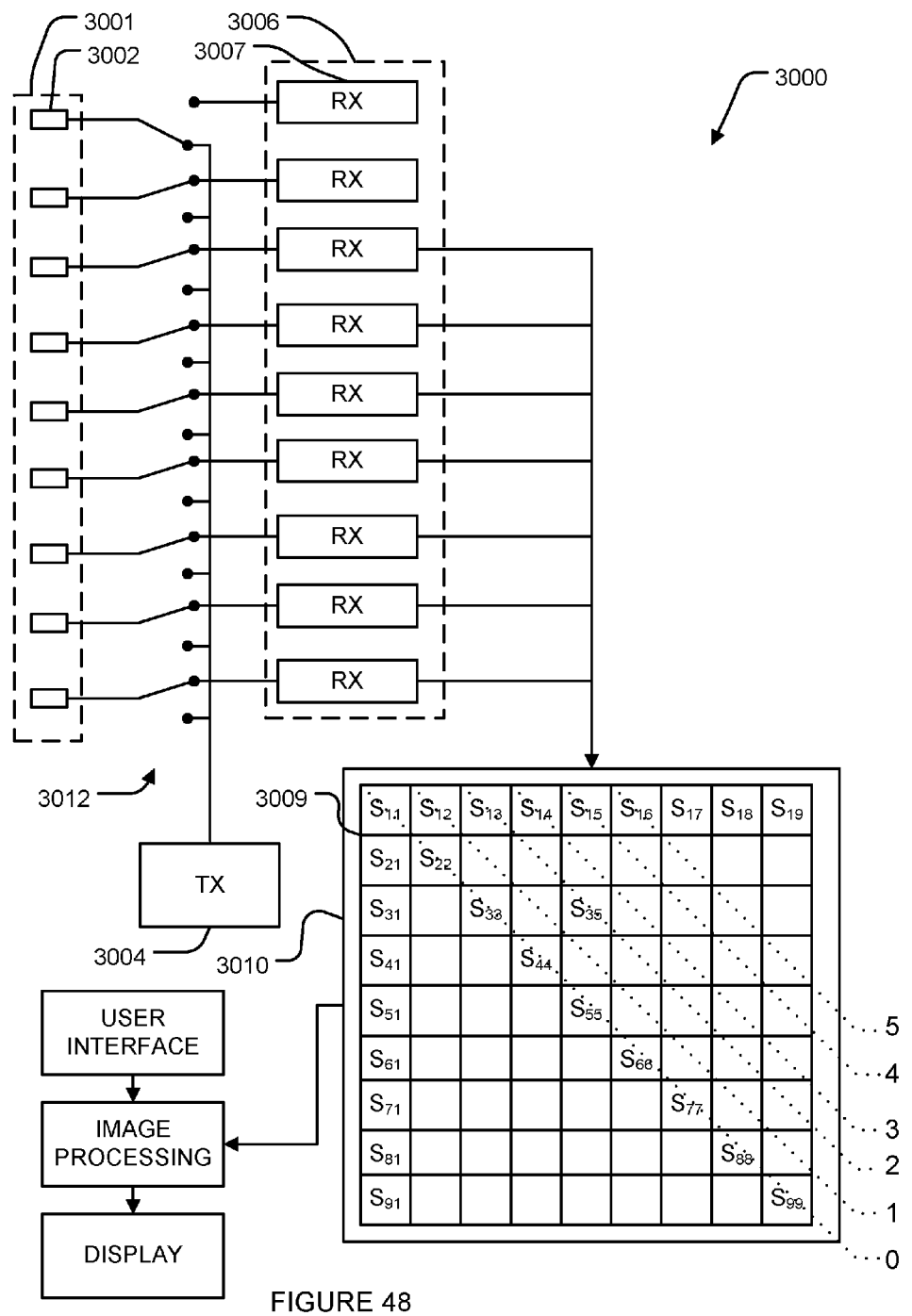
FIGS. 48 and 48A show schematic diagrams of different example embodiment ultrasound apparatus.
Figure 48A:
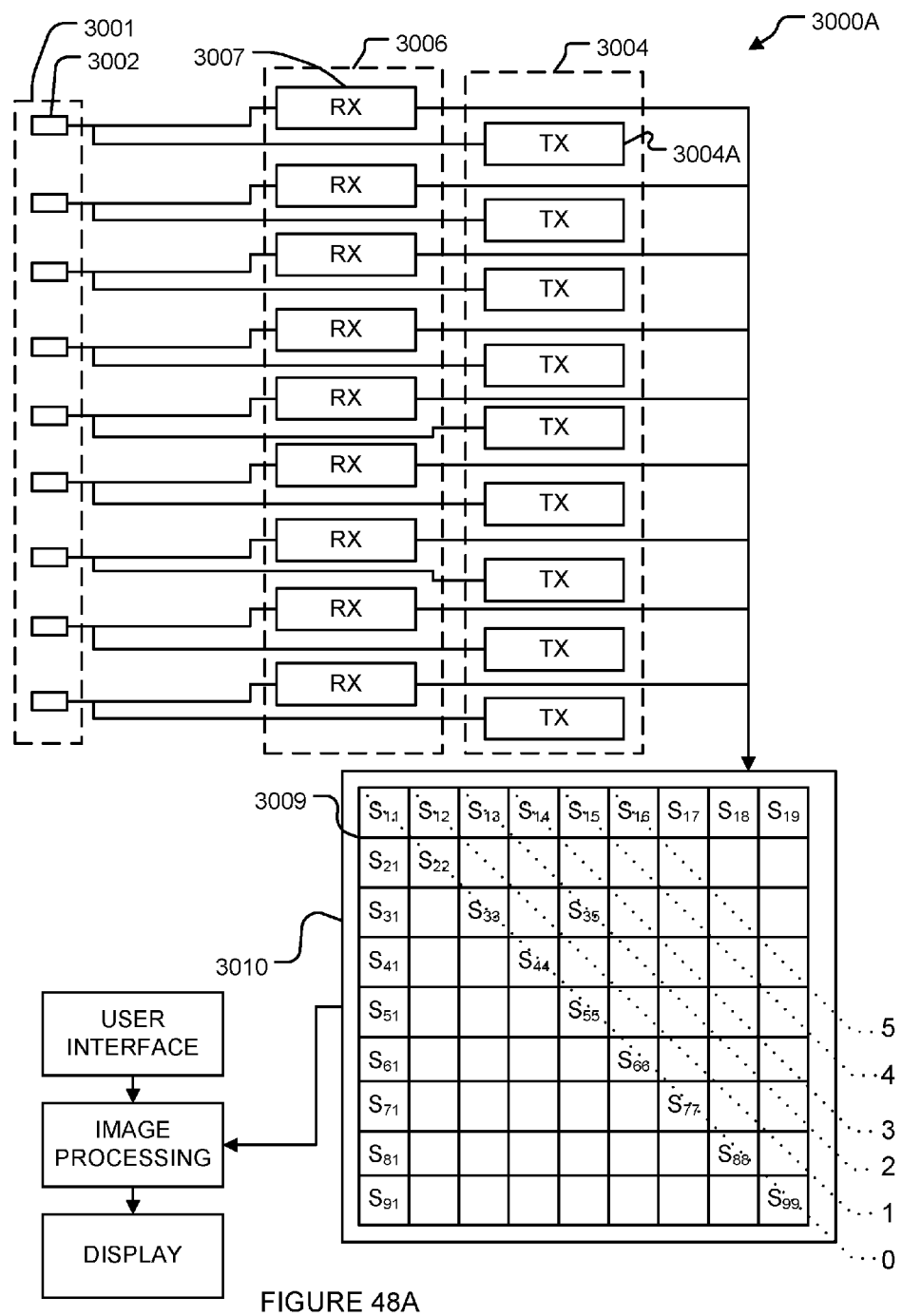

As described above, ultrasound data may be obtained by transmitting ultrasound from a transmitter and detecting the ultrasound at a plurality of different receivers. This may be repeated for different transmitters. The result is a collection of sets of received data. Each set of received data corresponds to a particular transmitter-receiver pair. Each set of received data may comprise, for example, a sequence of samples of a signal received at a receiver detecting ultrasound In the following discussion it is convenient to consider the case where all of the data is acquired and stored and then the stored data is processed to obtain images or other desired information about the tissue or other medium being studied. This is illustrated in FIGS. 48 and 48A. FIG. 48 shows ultrasound apparatus 3000 comprising a transducer 3001 comprising an array of elements 3002. Each element 3002 can function as a transmitter when driven by transmitter circuitry 3004 or as a receiver when connected to receive circuitry 3006.

In the illustrated embodiments, receive circuitry 3006 comprises a separate receiver 3007 for each element 3002 and each receiver 3007 provides a digital output that is stored in a data structure 3009 in a memory 3010. In the FIG. 48 embodiment, a switching network 3012 allows any one of elements 3002 to be connected to be driven by transmitter circuitry 3004 while the remaining elements 3002 are connected to the corresponding receiver 3007. Data characterizing a tissue or other medium may be acquired by selecting each element 3002 in turn to be used as a transmitter and, in each turn, receiving digitizing and storing the signals received by each of the other elements.

FIG. 48A shows ultrasound apparatus 3000A which is similar to ultrasound apparatus 3000 except that apparatus 3000A has a transmitter 3004 which includes transmitter circuitry 3004A dedicated for each transducer element 3002 and apparatus 3000A does not have a switching network 3012. Apparatus 3000A may be operated to acquire data by transmitting from one or elements 3002 using the corresponding transmitter circuitry 3004A, and receiving and storing the resulting signals at elements 3002 as described above for apparatus 3000.

It is not mandatory to obtain data from every available transmit-receive pair. Transmission of ultrasound may be performed using a selected subset of the elements. Selected subsets of the elements may be applied to receive signals resulting from transmission from each of the transmit elements. In some embodiments an element may be used as both a transmit element and a receive element in the same turn.

In some embodiments, ultrasound is transmitted into a medium by simultaneously operating two or more transmit elements 3002. For example, a group of elements 3002 may be operated in a coordinated fashion to emit ultrasound having the characteristics of a point source. Operating a plurality of transmit elements as a virtual point source is known in the art and described, for example, in Lokke et al. *Multielement Synthetic Transmit Aperture Imaging Using Temporal Encoding*, IEEE Transactions on Medical Imaging, Vol. 22, No. 4, April 2003, p. 552. The location of the virtual point source may be changed by driving the plurality of transmit elements using different driving signals and/or by changing the members of the group of elements used to transmit ultrasound as a virtual point source.

In some embodiments, signals are received by groups of elements 3002. For example, as described above in relation to FIG. 16, signals from a group of elements may be combined so as to increase an effective sampling rate of ultrasound echo signals.

FIGS. 48 and 48A show digitized data arranged in a matrix in which columns correspond to the element 3002 used to transmit ultrasound into the medium and rows correspond to the elements at which signals are received. For example, the location at row 3, column 5 contains a sequence $S_{35}$ of digital samples obtained by sampling the $5^{th}$ element for signals received in response to ultrasound transmitted using the $3^{rd}$ element of the transducer. In an embodiment where ultrasound signals are transmitted by a group of elements operating as a virtual point source the columns may correspond to different locations of the virtual point source instead of different individual transmitting elements.

Different transmitter-receiver pairs are separated by different distances. For example, where the transmitters and receivers are elements of a linear transducer array in which the elements are equally spaced apart along the array, some transmitter-receiver pairs may be spaced apart by one unit of array spacing and other transmitter-receiver pairs may be spaced apart by multiple units of the array spacing. The different separation distances between a transmitting element and a receiving element (or between the location of a virtual point source and a receiving element) are called 'offsets' above (for example, see FIGS. 20 to 24 and the accompanying discussion). It is convenient but not mandatory that the elements of the transducer array are equally spaced apart.

Ultrasound data originating from transmitter-receiver pairs that are separated by different distances (i.e. data corresponding to different offsets) may contain different information regarding the nature of the medium. For example, different offsets (i.e. different angles subtended by the transmitter and receiver at a point in the medium) interrogate different spatial frequencies in the medium. This effect can be exploited to allow the formation of images with different spatial frequency balances. For example, one image may be formed by selecting image data corresponding to a first offset (or offsets in a first range) while another image is formed by selecting image data corresponding to a second offset (or a second range of offsets). The first image may be enriched in lower spatial frequencies relative to the second image while the second image is enriched in higher spatial frequencies relative to the first image or vice versa, for example.

The diagonal lines overlaid on data structure 3009 in FIG. 48 each cross locations containing data characterized by the same offset. These lines assume that the transducer elements are equally spaced apart along a line and are identified by an index such that the element at one end of the transducer array has the index "1", the next element has the index "2" and so on.

Images may be generated from the raw data in memory 3010. Each image may be generated based on less than all of the raw data in memory 3010 For example, the images may be generated by one or more of:

selecting ultrasound data corresponding to a first offset (or to a first set of selected offsets e.g. offsets in a first range) and performing image processing operations on the selected image data;

selecting a plurality of sets of ultrasound data corresponding to a plurality of different offsets or sets of selected offsets and preparing an image by performing image processing operations on the different sets of ultrasound data and combining the results of the image processing operations. Different image processing operations may be applied to the different sets of ultrasound data.

In one example embodiment, a first image that is relatively enriched in low spatial frequencies is generated from ultrasound data selected from transmitter-receiver pairs having a first offset or range of offsets (e.g. transmitter-receiver pairs where the transmitter and receivers are separated by smaller distances). A second image that is enriched in higher spatial frequencies relative to the first image is generated from ultrasound data selected from transmitter-receiver pairs having a second offset or range of offsets (e.g. transmitter-receiver pairs where the transmitter and receivers are separated by relatively larger distances). The first image may be processed by low-pass spatial filtering. This can help to make continuous anatomical borders appear continuous in the image. The resulting low-pass spatial filtered image can then be combined with the second image to yield an image for display. The images may optionally be weighted before being combined. In some embodiments, the second image may comprise a B-mode image. The B-mode image may be obtained using methods and apparatus as described herein or using other B-mode imaging methods and apparatus. Combining the first and second image may comprise determining a sum or weighted sum of the first and second images for example.

Figure 49:
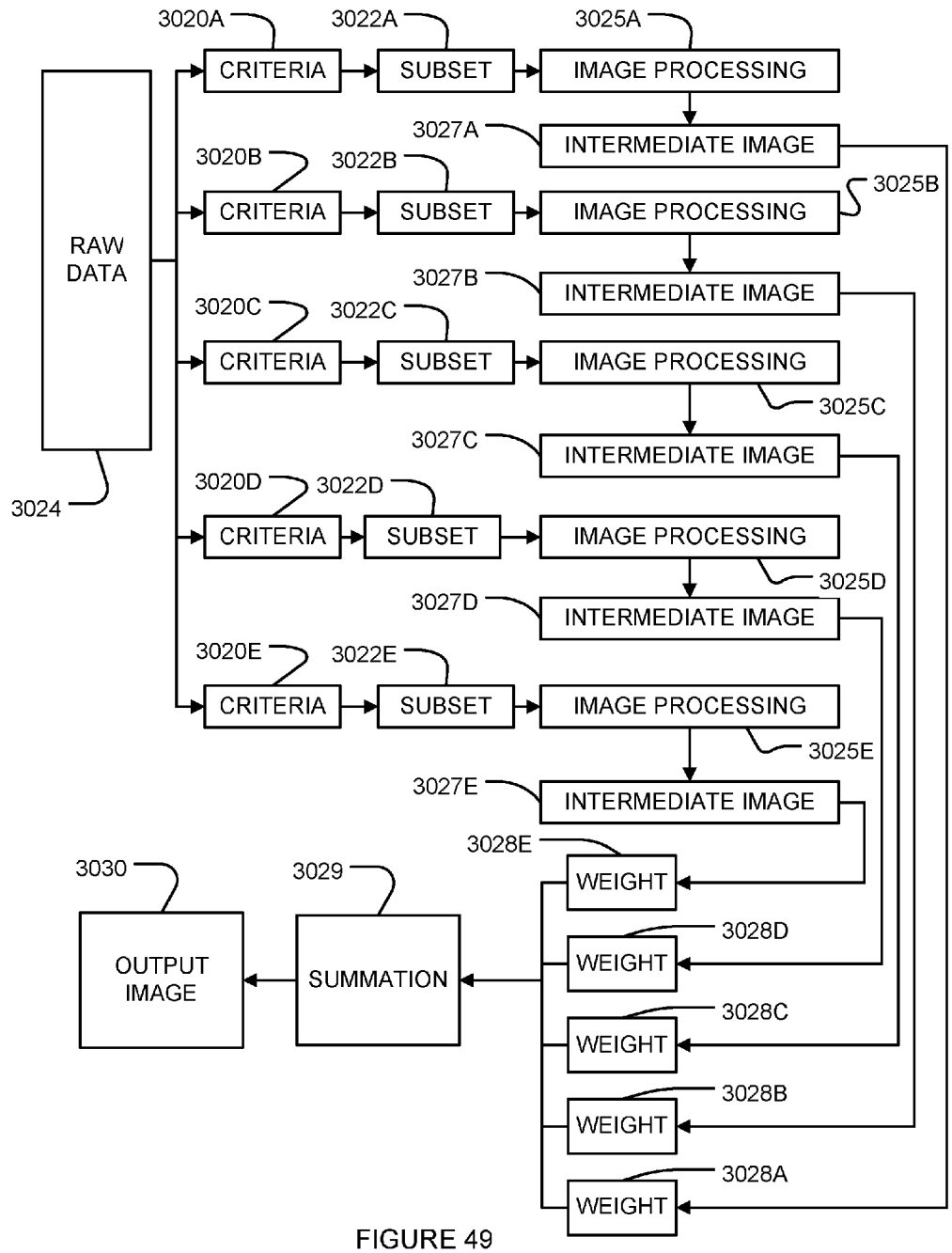
FIG. 49 show a schematic of different steps used to process raw date into an output image.

In other embodiments, more than two images are combined to yield a final image. FIG. 49 schematically illustrates a case in which N offset criteria are applied to select N subsets of the raw data. The offset criteria may, for example comprise one or more of criteria which require that to be selected, the data must have:

a specific offset value;

an offset value that is a member of a specific set of offset values;

an offset value above a threshold;

an offset value below a specified threshold;

an offset value in a specified range;

or the like.

Selection criteria may include other factors as well as offsets. For example, selection criteria may include a criterion which selects for signals received at a receive element lying within a specified aperture.

In FIG. 49, criteria 3020A through 3020E (collectively criteria 3020) are respectively applied to select subsets 3022A through 3022E from raw data 3024. The data subsets are respectively processed by image processing steps 3025A through 3025E (collectively image processing steps 3025) to yield intermediate images 3027A through 3027E. Images 3027A through 3027E are weighted according to corresponding weights 3028A through 3028E (collectively weights 3028) before they are combined by image summation stage 3029 to yield a final image 3030.

Image processing steps 3025 may, for example, include one or more of:
- low pass filtering;
- high pass filtering;
- bandpass filtering;
- texture analysis;
- edge detection;
- edge enhancement;
- contrast adjustment;
- coloration; and
- pass through (no image processing).

In some embodiments some or all of criteria 3020, image processing steps 3025 and weights 3028 are set according to user input. This can permit a user to adjust these parameters to obtain a final image 3030 of a desired quality. Since raw data 3024 is stored, the user can experiment with a wide range of settings to observe the resulting final images 3030 all based on the same raw data 3024. In some embodiments, apparatus 3000 or 3000A provides a mechanism for storing user-selected parameters such as weights and/or other image processing parameters such that future images may be processed using the same user-selected parameters. Some embodiments provide a data store containing one or more preset sets of parameters. Such embodiments may optionally permit users to alter the parameters either arbitrarily or, in some cases, only within a predetermined limited range of manipulation.

In some embodiments, information from different intermediate images (either alone or in combination with other information) is used to make decisions about the display of the final image. For example:
- A spatial frequency image having a relatively enhanced low spatial frequency content (e.g. an image acquired from data from transmit-receive pairs separated by smaller distances) may be used for detecting borders and anatomical edges. In the final image, the borders may be superimposed onto a B-mode ultrasound image.
- The energy content of an image may be measured (either for the image as a whole or for one or more selected spatial frequency bands in the image). A measure of energy may be obtained, for example, by summing pixel values (or a function of the pixel values such as the square of the pixel values) over the image. If the energy of one intermediate image exceeds a threshold then one or more other intermediate images may be not included in the final images or may be weighted less in the final image.
- If the energy content of an intermediate image having a lower spatial frequency content (or in a lower-spatial frequency band within an intermediate image) exceeds a threshold then a low-pass filter may be applied to the final image so as to emphasize the lower spatial frequency data.
- If the energy content of an intermediate image having a higher spatial frequency content exceeds a threshold then a high-pass filter may be applied to the final image.

Thus, the characteristics of one or more intermediate images may be measured and used in an automated process to determine the selection of which intermediate images are to be included in the final image; determine weights used in combining the intermediate images into the final image and/or control properties of or determine whether or not a filtering operation will be performed on the final image or on one or more of the intermediate images.

It is not mandatory that the transmit and receive elements be arranged in a linear array (or even that they be arranged in a regular array). In some embodiments the transmit and receive elements are arranged in a two-dimensional array. This facilitates use of data 3024 for volumetric imaging. In the case of volumetric imaging, offsets (or equivalently separation distances) can be determined for transmit-receive pairs that are not on the same line. By selecting appropriate transmit-receive pairs (i.e. transmit-receive pairs in which transmitting and receiving elements have separations that match selection criteria), volumetric images having different spatial frequency contents may be obtained. Standard processing can be applied to obtain 2D images for any plane within the volumetric region of the medium being studied. For example, from the volumetric image one can obtain images lying in any of the planes in which a central axis of the transducer lies (the central axis is normal to the transducer and passes through the center of the transducer).

As in the case of the images described above, different volumetric images may be derived from data from transmit-receive pairs for which the offsets satisfy different selection criteria. These different volumetric images may be subjected to different image processing steps and then optionally combined to yield a final image. The methods described above can be directly extended to the volumetric case.

Spatial Compounding

Figure 50:
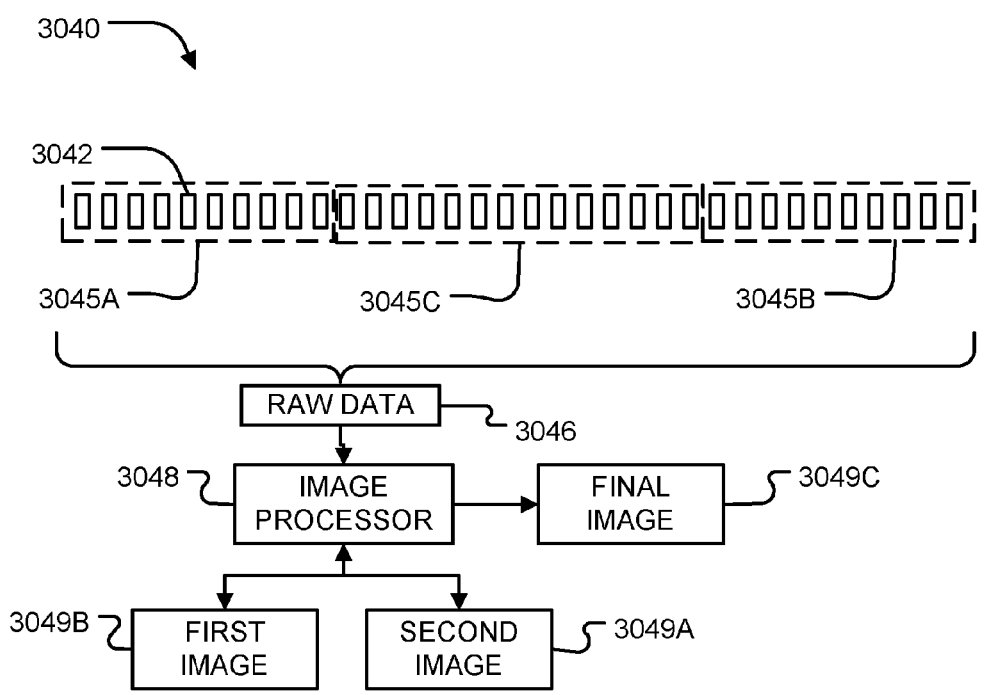
FIG. 50 shows a schematic of a system for obtaining different types of images from raw data.

As discussed above, a plurality of different images may be obtained from raw data 3024 by selecting data based at least in part on the offset for transmit-receive pairs. As illustrated in FIG. 50, a system as described herein may be applied to obtain different types of images from raw data. For example, ultrasound may be transmitted into a medium using elements belonging to a subset of the elements of a transducer. After each transmission, elements of the transducer array are monitored to acquire signals resulting from the interaction of the ultrasound with the medium. Therefore, each transmission may result in a number of received signals (up to one received signal for every transducer element). These received signals may be stored in a suitable data structure as described above, for example.

A plurality of different images may be created from different subsets of the received signals. In a particularly useful embodiment, at least first and second images are generated. The first image is based on data received at transducer elements lying within a first aperture and the second image is based on data received at transducer elements lying within a second aperture. The first and second apertures are preferably non-overlapping. In some embodiments the set of elements used to transmit the ultrasound lies between the first and second apertures. This is illustrated in FIG. 50 which shows a transducer 3040 having elements 3042. A first group of the elements lies within a first aperture 3045A. A second group of the elements lies within a second aperture 3045B. A third group of the elements lies within a third aperture 3045C. In the illustrated embodiment, aperture 3045C lies between apertures 3045A and 3045B.

A method of use transmits ultrasound from elements of one aperture (e.g. aperture 3025C) and receives signals at elements of the other apertures. In some embodiments a plurality of elements within aperture 3025C are operated in concert as a virtual point source. This facilitates transmission of higher power ultrasound pulses.

Separate images may be formed from data received by elements within each of the other apertures. For example, separate images may be created from the data received at elements within apertures 3045A and 3045B.

Advantageously, images formed from signals received at elements in different apertures tend to have different speckle patterns. Thus, speckle patterns may be de-emphasized or eliminated by combining images formed from signals received at elements in different apertures. It is most convenient for the receive apertures to be equal in size such that the images to be combined are equivalent. In embodiments where the different apertures have different sizes then the pixel dimensions of the images may be matched by upsampling and/or downsampling before the images are combined. The combining may comprise, for example, summing the images.

In some embodiments, the images to be combined are each constructed from intermediate images as described above with reference to FIG. 49.

In the illustrated embodiment, data from all receive elements (i.e. N sets of data where N is the number of elements in transducer 3040) is accumulated in a data structure 3046. An image processor 3048 is configured to select subsets of the data corresponding to at least first and second apertures and to process each selected subset of the data to yield corresponding images 3049A, 3049B and to combine images 3049A and 3049B to yield a final image 3049C.

Image processing may comprise, for example, performing detection by rectifying and low-pass filtering the image data. Log compression and/or other image processing steps may optionally be performed. The images may be subsequently combined, for example by addition. With this type of processing, spatial compounding may be achieved with one firing.

Other allocations of transducer elements to transmit and/or receive apertures are possible. For example the apertures may overlap. Where receive data is available for all transducer elements, images may be subsequently generated for any apertures. It is desirable but not mandatory that the apertures be the same size. In general, data from smaller apertures provides images having poorer spatial resolution than data from larger apertures. However, speckle patterns in images from smaller apertures are more independent than those in images obtained from data from larger apertures.

In some embodiments, images are generated automatically for a plurality of different aperture sizes and/or separations between the transmitting and receiving apertures. In some such embodiments, a method comprises, constructing images for apertures of a first size and comparing the constructed images. The comparison may be performed for example, by computing a correlation or other similarity measure between the images. If the comparison indicates that the images are significantly different (e.g. a correlation value is less than some threshold) then the images are combined. Otherwise, images are constructed for apertures of a second size smaller than the first size and the resulting images are compared. The process is iterated for smaller and smaller apertures until either the comparison indicates that the images are significantly different or predetermined maximum number of iterations has been completed.

Retrospective Processing

In embodiments in which raw data is acquired and remains available, it is possible to process the same raw data in different ways in an attempt to obtain images of optimal quality. For different applications the meaning of 'optimal' may differ. The different processing may comprise one or more of:
- selecting different subsets of the raw image data from which to generate images (selecting data corresponding to transmit-receive pairs having different offsets is one example of this);
- changing a parameter used in generating images (one example of this is changing the assumed speed of sound in the medium being investigated);
- changing a parameter which alters the way in which images are generated (for example a parameter that determines the thickness or maximum number of sub-layers in the method illustrated in FIG. 33, a parameter that controls the degree of focusing, or the like);
- changing the nature of image processing applied to generated images and/or changing parameters that affect the image processing (examples are determining whether or not a particular image will be filtered, what type of filter will be applied to an image, changing parameters that affect the operation of a filter, changing a function used for apodization etc.)

Changes to these parameters may be performed under the control of a user operating a suitable user interface or performed automatically or semi-automatically. For example, in some embodiments a user can identify a parameter to be varied and the system is configured to generate images for a plurality of different values of the parameter. Evaluation of the images may be done by a user or automatically based on suitable criteria.

In an example application, receive apodization may be modified. An apodization function weights the contribution of signals to an image such that signals from elements near the center of an aperture are weighted more heavily while signals from elements near edges of the aperture are weighted less heavily. The apodization function may comprise a series of values that correspond to positions of the receiving elements in the array.

As is well known, uniform apodization (all signals weighted equally) produces maximum main lobe resolution but also produces high levels of side lobes. A Hamming or Hanning apodization function reduces main lobe resolution but beneficially decreases the levels of side lobes. Other apodization functions include Bartlett, Blackman, cosine, and Gaussian apodization functions.

In a system as described herein, different images may be created using different apodization functions and compared to identify the best image for the current application. For example, in a method according to one embodiment, a plurality of images are automatically created. A different apodization function is applied to processing the raw data for each of the plurality of images. The plurality of images are then compared to one another to identify a best one. In some embodiments, comparison is done by a human observer. All of the images are presented and the observer can select what he or she considers to be the best one. In some embodiments, a plurality of the images are presented simultaneously on one or more displays so that the user can compare them directly.

An automatic selection mechanism may be implemented to select the 'best' choice or choices of apodization function according to a predetermined criterion. There are several ways to pick the best apodization function automatically.

It is not necessary that the same apodization function be used throughout each image. Different apodization functions may be applied for different locations or areas within an image. Different apodization functions may even be applied to different pixels or voxels in an image. For example, in some embodiments, an apparatus is configured to analyze image data for borders or edges. This may be achieved through the application of standard image analysis algorithms, for example, or through generating an image in which lower spatial frequency content is emphasized as described above. In the vicinity of borders or edges, better image quality may be obtained by applying a non-uniform apodization function (such as a Hamming or Hanning function) whereas in image regions away from borders and edges a uniform apodization function (all signals weighted the same) or an apodization function that is closer to a uniform apodization function may provide better results.

In some embodiments, a preliminary image is prepared and image analysis is performed on the preliminary image to identify areas for which different image processing may be desired. For example, the image analysis may perform a routine for identifying pixels that are in the vicinity of borders or edges. In some such embodiments, generating the preliminary image is performed using a first number of the stored sampled signals and generating a further image in which apodization functions are selected based on one or more features identified in the preliminary image (e.g. borders or edges) is performed using a second number of the stored sampled signals greater than the first number. Thus, the identification of borders and edges may be performed with a relatively low expenditure of computational resources.

Some embodiments implement image processing methods which comprise: generating a first image from raw data as described herein; identifying in the first image first image regions that include borders or edges and second image regions that do not include borders or edges (or have a reduced content of borders and edges); applying a first apodization function to the raw data to obtain pixel values for pixels in the first region; applying a second apodization function to the raw data to obtain pixel values for pixels in the second region; and assembling a second image from the pixel values for the first and second regions. In some embodiments, the first image is obtained using one of the first and second apodization functions and so the second image may be assembled from pixel values from the first image in one of the first and second regions and pixel values obtained from the raw data using the other one of the first and second apodization functions in the other one of the first and second regions.

As another example, in areas approaching pure speckle, uniform apodization may provide the best results. Such areas may be identified by statistical analysis. For example one may compute a ratio of a mean pixel value for the region to a variance of the pixel values in the region. This ratio tends to approach a value of 1.9 in regions approaching pure speckle. One can select an apodization function to use in a region based on this ratio. For example, uniform apodization may be selected when the ratio exceeds a threshold for a region or the deviation of an apodization function from uniform may be increased as the value of the ratio becomes more different from 1.9.

In an example embodiment, a first image is obtained by processing raw data as described herein. A statistical measure of speckle (e.g. mean/variance) is determined for each of a plurality of different regions in the first image. An apodization function is selected for each of the plurality of regions based on the corresponding statistical measure. Pixel values are then determined for each of the regions by processing the raw data using the corresponding apodization function. A second image is assembled by combining the pixel values for the plurality of regions.

In some embodiments, apodization is optimized individually for a number of different imaging regions. Apodization may be optimized on a image pixel by image pixel basis. Optimizing receive apodization as described herein may be applied to volumetric imaging as well as to 2D imaging.

It will be understood that while the present disclosure is often described in the context of medical ultrasound applications, various techniques and principles disclosed herein can apply equally well to other fields where ultrasound is used (for example, non destructive testing).

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

What is claimed is:

1. An ultrasound imaging method comprising:
   (a) transmitting an ultrasound signal into a subject by operating a plurality of transducer elements of an ultrasound transducer;
   (b) receiving an ultrasound echo signal corresponding to the transmitted ultrasound signal at transducer elements of the ultrasound transducer; and
   (c) for each of a plurality of apertures, each of the apertures comprising a plurality of the transducer elements of the ultrasound transducer, processing the ultrasound echo signals received at the transducer elements of the aperture to yield an image
   wherein operating the plurality of transducer elements comprises operating the plurality of transducer elements in concert to provide a virtual ultrasound point source.

2. A method according to claim 1 comprising combining a plurality of images corresponding to a plurality of the apertures to yield a combined image wherein the combined image has reduced speckle as compared to the plurality of images.

3. A method according to claim 1 wherein transmitting the ultrasound signal comprises operating one or more of the transducer elements located between a first one of the plurality of apertures and a second one of the plurality of apertures.

4. A method according to claim 1 wherein transmitting the ultrasound signal comprises, at one time interval operating the transducer elements associated with a first one of the apertures and receiving the echo signals at the transducer elements associated with a second one of the apertures and at another time interval operating the transducer elements associated with the second one of the apertures and receiving the echo signals at the transducer elements associated with the first one of the apertures.

5. A method according to claim 1 wherein the apertures are each associated with an equal number of the transducer elements.

6. A method according to claim 1 wherein the apertures are non-overlapping.

7. A method according to claim 1 comprising automatically generating images from the ultrasound echo signals received at the transducer elements wherein the images are generated for a plurality of different aperture sizes.

8. A method according to claim 1 comprising automatically generating images from the ultrasound echo signals received at the transducer elements wherein the images are generated for a plurality of different separations between the apertures.

9. An ultrasound imaging method comprising:
   (a) transmitting an ultrasound signal into a subject;
   (b) receiving an ultrasound echo signal corresponding to the transmitted ultrasound signal at transducer elements of an ultrasound transducer; and
   (c) for each of a plurality of apertures, each of the apertures comprising a plurality of the transducer elements of the ultrasound transducer, processing the ultrasound echo signals received at the transducer elements of the aperture to yield an image;
   the method further comprising constructing images for apertures of a first size, comparing the constructed images, combining the images if the comparison indicates that the images are significantly different and, if the comparison indicates that the images are not significantly different, constructing images for apertures of a second size smaller than the first size.

10. A method according to claim 9 wherein performing the comparison comprises computing a correlation or other similarity measure between the images.

11. A method according to claim 10 further comprising iterating the method for smaller and smaller apertures until a termination condition is satisfied.

12. A method according to claim 11 wherein the termination condition is satisfies where the comparison indicates that the images are significantly different or a predetermined maximum number of iterations has been completed.

13. A method according to claim 9 wherein transmitting the ultrasound signal into a subject comprises operating a plurality of transducer elements of the ultrasound transducer to provide a virtual ultrasound point source.

* * * * *